US010086088B2

(12) United States Patent
Head et al.

(10) Patent No.: US 10,086,088 B2
(45) Date of Patent: Oct. 2, 2018

(54) NEURONAL SPECIFIC TARGETING OF CAVEOLIN EXPRESSION TO RESTORE SYNAPTIC SIGNALING AND IMPROVE COGNITIVE FUNCTION IN THE NEURODEGENERATIVE BRAIN AND MOTOR FUNCTION IN SPINAL CORD

(71) Applicant: The Regents of the University of California, Oakland, CA (US)

(72) Inventors: Brian P. Head, Lakeside, CA (US); Piyush M. Patel, La Jolla, CA (US); Hemal Patel, La Jolla, CA (US); David M. Roth, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/608,153

(22) Filed: Jan. 28, 2015

(65) Prior Publication Data

US 2018/0055950 A1    Mar. 1, 2018

Related U.S. Application Data

(62) Division of application No. 13/883,503, filed as application No. PCT/US2011/059635 on Nov. 7, 2011, now Pat. No. 8,969,077.

(60) Provisional application No. 61/456,425, filed on Nov. 5, 2010.

(51) Int. Cl.
| | |
|---|---|
| *A61K 48/00* | (2006.01) |
| *A61K 31/7088* | (2006.01) |
| *A61K 38/17* | (2006.01) |
| *C12N 15/86* | (2006.01) |

(52) U.S. Cl.
CPC .......... *A61K 48/00* (2013.01); *A61K 31/7088* (2013.01); *A61K 38/17* (2013.01); *A61K 48/0058* (2013.01); *C12N 15/86* (2013.01); *A61K 38/177* (2013.01); *C12N 2740/16043* (2013.01); *C12N 2830/002* (2013.01); *C12N 2830/48* (2013.01); *C12N 2840/00* (2013.01)

(58) Field of Classification Search
None
See application file for complete search history.

(56) References Cited

U.S. PATENT DOCUMENTS

| | | |
|---|---|---|
| 5,033,252 A | 7/1991 | Carter |
| 5,052,558 A | 10/1991 | Carter |
| 5,323,907 A | 6/1994 | Kalvelage |

FOREIGN PATENT DOCUMENTS

| | | |
|---|---|---|
| WO | 02/20768 | 3/2002 |

OTHER PUBLICATIONS

Jasmin, et al. (2006) "Short-Term Administration of a Cell-Permeable Caveolin-1 Peptide Prevents the Development of Monocrotaline-Induced Pulmonary Hypertension and Right Ventricular Hypertrophy", Circulation, 114(9): 912-20.*
Liu, et al. (2002) "Multiple Functions of Caveolin-1", Journal of Biological Chemistry, 377: 41295-98.*
Fang, et al. (2007) "Overexpression of Caveolin-1 Inhibits Endothelial Cell Proliferation by Arresting the Cell Cycle at G0/G1 Phase", Cell Cycle, 6(2): 199-204.*
Stern (2010) "Caveolin regulation of neuronal intracellular signaling", Cellular and Molecular Life Sciences, 67(22): 3785-95.*
Sohur, et al. (2006) "Adult neurogenesis and cellular brain repair with neural progenitors, precursors and stem cells", Philosophical Transactions of the Royal Society of London B, Biological Sciences, 361(1473) 1477-97.*
Honorio Junior, et cal. (2012) "Monocrotaline: Histological Damage and Oxidant Activity in Brain Areas of Mice", Oxidative Medicine and Cellular Longevity, Article 697541: 10 pages long.*
Yankner, Bruce A. et al., "The Aging Brain," *Annu. Rev. Pathol. Mech. Dis.*, 2008, 3:41-66 (Exhibit 162).
Yee, Jiing-Kuan et al., "A general method for the generation of high-titer, pantropic retroviral vectors: Highly efficient infection of primary hepatocytes," *Proc. Natl. Acad. Sci. USA*, 1994, 91:9564-8 (Exhibit 163).
Yoon, Il-Sang et al., "Low-density lipoprotein receptor-related protein promotes amyloid precursor protein trafficking to lipid rafts in the endocytic pathway," *The FASEB Journal*, 2007, 21:2742-52 (Exhibit 164).
Zennou, Véronique et al., "HIV-1 Genome Nuclear Import Is Mediated by a Central DNA Flap," *Cell*, 2000, 101:173-85 (Exhibit 165).
Zhao, Hui et al., "Neurite Outgrowth is Dependent on the Association of c-Src and Lipid Rafts," *Neurochem Res*, 2009, 34:2197-205 (Exhibit 166).
Zhou, X. et al., "Optimization of the Tet-On system for regulated gene expression through viral evolution," *Gene Therapy*, 2006, 13:1382-90 (Exhibit 167).
Zhu, Manjie et al., "Increased oxidative stress and astrogliosis responses in conditional double-knockout mice of Alzheimer-like presenilin-1 and presenilin-2," *Free Radical Biology & Medicine*, 2008, 45:1493-9 (Exhibit 168).
Zinchuk, Olga et al., "Dynamics of PAF-induced conjunctivitis reveals differential expression of PAF receptor by macrophages and eosinophils in the rat," *Cell Tissue Res*, 2004, 317:265-77 (Exhibit 169).
Zufferey, Romain et al., "Woodchuck Hepatitis Virus Post-transcriptional Regulatory Element Enhances Expression of Transgenes Delivered by Retroviral Vectors," *Journal of Virology*, 1999, 73:2886-92 (Exhibit 170).
Figurov, Alexander et al., "Regulation of synaptic responses to high-frequency stimulation and LTP by neurotrophins in the hippocampus," *Nature*, 1996, 381:706-9 (Exhibit 171).
Clark, et al. (2003) "Inferring nonneutral evolution from human-chimp-mouse orthologous gene trios", Science 302 (5652): 1960-63 (Exhibit 172).

(Continued)

*Primary Examiner* — Robert M Kelly
(74) *Attorney, Agent, or Firm* — Gavrilovich, Dodd & Lindsey LLP

(57) ABSTRACT

The invention provides an expression system for producing Caveolin-1 in neuronal cells or neural stem cells comprising a neuron-specific regulatory element and a nucleic acid sequence encoding Caveolin-1.

8 Claims, 36 Drawing Sheets

Specification includes a Sequence Listing.

(56) References Cited

OTHER PUBLICATIONS

Kugler, et al. (2003) "Human synapsin 1 gene promoter confers highly neuron-specific long-term transgene expression from an adenoviral vector in the adult rat brain depending on the transduced area", Gene Therapy, 10(4): 337-47 (Exhibit 173).

Thiel, et al. (1991) "Characterization of tissue-specific transcription by the human synapsin 1 gene promoter", Proceedings of the National Academy of Science, USA., vol. 88, pp. 3431-3435 (Exhibit 174).

Akagi, Kiwamu et al., "A novel tetracycline-dependent transactivator with E2F4 transcriptional activation domain," Nucleic Acids Research, 2001, 29:e23 (Exhibit 5).

Allen, John A. et al., "Lipid raft microdomains and neurotransmitter signaling," Nature Reviews, 2007, 8:128-40 (Exhibit 6).

Alto, Laura Taylor et al., "Chemotropic Guidance Facilitates Axonal Regeneration and Synapse Formation after Spinal Cord Injury," Nat Neurosci, 2009, 12:1106-13 (Exhibit 7).

Atkins, Coleen M. et al., "Modulation of the cAMP signaling pathway after traumatic brain injury," Exp Neurol., 2007, 208:145-58 (Exhibit 8).

Atkins, Coleen M. et al., "Deficits in ERK and CREB activation in the hippocampus after traumatic brain injury," Neurosci. Lett., 2009, 459:52-6 (Exhibit 9).

Bamji, Shernaz X. et al., "Role of β-Catenin in Synaptic Vesicle Localization and Presynaptic Assembly," Neuron, 2003, 40:719-31 (Exhibit 10).

Behrens, M. Margarita et al., "Ketamine-Induced Loss of Phenotype of Fast-Spiking Interneurons Is Mediated by NADPH-Oxidase," Science, 2007, 318:1645-7 (Exhibit 11).

Bertram, Lars and Rudolph E. Tanzi, "Thirty years of Alzheimer's disease genetics: the implications of systematic meta-analyses," Nature Reviews, 2008, 9:768-78 (Exhibit 12).

Besshoh, Shintaro et al., "Increased phosphorylation and redistribution of NMDA receptors between synaptic lipid rafts and post-synaptic densities following transient global ischemia in the rat brain," Journal of Neurochemistry, 2005, 93:186-94 (Exhibit 13).

Biegon, Anat et al., "Dynamic changes in N-methyl-D-aspartate receptors after closed head injury in mice: Implications for treatment of neurological and cognitive deficits," PNAS, 2004, 101-5117-22 (Exhibit 14).

Bilderback, Tim R. et al., "Caveolin Interacts with TrkA and p75$^{NTR}$ and Regulates Neurotrophin Signaling Pathways," The Journal of Biological Chemistry, 1999, 274:257-63 (Exhibit 15).

Bishop, Nicholas A. et al., "Neural mechanisms of ageing and cognitive decline," Nature, 2010, 464:529-35 (Exhibit 16).

Bist, Anita et al., "Two sterol regulatory element-like sequences mediate up-regulation of caveolin gene transcription in response to low density lipoprotein free cholesterol," Proc. Natl. Acad. Sci. USA, 1997, 94:10693-8 (Exhibit 17).

Bist, Anita et al., "p53 Regulates Caveolin Gene Transcription, Cell Cholesterol, and Growth by a Novel Mechanism," Biochemistry, 2000, 39:1966-72 (Exhibit 18).

Björk, Karl et al., "Regulation of serotonin receptor function in the nervous system by lipid rafts and adaptor proteins," Experimental Cell Research, 2010, 316:1351-6 (Exhibit 19).

Blesch, A. et al., "Modulation of neuronal survival and axonal growth in vivo by tetracycline-regulated neurotrophin expression," Gene Therapy, 2001, 8:954-60 (Exhibit 20).

Bourasset, Fanchon et al., "Reduction of the cerebrovascular volume in a transgenic mouse model of Alzheimer's disease," Neuropharmacology, 2009, 56:808-13 (Exhibit 21).

Bouwman, J, et al., "Quantification of Synapse Formation and Maintenance In Vivo in the Absence of Synaptic Release," Neuroscience, 2004, 126:115-26 (Exhibit 22).

Bulloj, Ayelén et al., "Detergent resistant membrane-associated IDE in brain tissue and cultured cells: Relevance to Aβ and insulin degradation," Molecular Neurodegeneration, 2008, 3:22 (Exhibit 23).

Cai, Dongming et al., "Neuronal Cyclic AMP Controls the Developmental Loss in Ability of Axons to Regenerate," The Journal of Neuroscience, 2001, 21:4731-9 (Exhibit 24).

Calabrese, Barbara et al., "Development and Regulation of Dendritic Spine Synapses," Physiology, 2006, 21:38-47 (Exhibit 25).

Cameron, Patricia L. et al., "Identification of Caveolin and Caveolin-Related Proteins in the Brain," The Journal of Neuroscience, 1997, 17:9520-35 (Exhibit 26).

Carmichael, S. Thomas et al, "Themes and Strategies for Studying the Biology of Stroke Recovery in the Post-Stroke Epoch," Stroke, 2008, 39:1380-8 (Exhibit 27).

Cecchi, C. et al., "Seladin-1/DHCR24 protects neuroblastoma cells against Aβ toxicity by increasing membrane cholesterol content," J. Cell Mol. Med., 2008, 12:1990-2002 (Exhibit 28).

Cerezo-Guisado, Maria Isabel et al., "Lovastatin inhibits the extracellular-signal-regulated kinase pathway in immortalized rat brain neuroblasts," Biochem. J., 2007, 401:175-83 (Exhibit 29).

Cohen, Alex W. et al., "Caveolin-1 null mice develop cardiac hypertrophy with hyperactivation of p42/44 MAP kinase in cardiac fibroblasts," American Journal of Physiology—Cell Physiology, 2003, 284:C457-74 (Exhibit 30).

Cohen, Alex W. et al., "Role of Caveolae and Caveolins in Health and Disease," Physiol Rev, 2004, 84:1341-79 (Exhibit 31).

Crameri, Arames et al., "The role of seladin-1/DHCR24 in cholesterol biosynthesis, APP processing and Aβ generation in vivo," The EMBO Journal, 2006, 25:432-43 (Exhibit 32).

Cronin, Carolyn A. et al., "The lac operator-repressor system is functional in the mouse," Genes & Development, 2001, 15:1506-17 (Exhibit 33).

Denny, John B., "Molecular Mechanisms, Biological Actions, and Neuropharmacology of the Growth-Associated Protein GAP-3," Current Neuropharmacology, 2006, 4:293-304 (Exhibit 34).

Derry, D. M. and L. S. Wolfe, "Gangliosides in Isolated Neurons and Glial Cells," Science, 1967, 158:1450-2 (Exhibit 35).

Dickstein, Dara L. et al., "Role of Vascular Risk Factors and Vascular Dysfunction in Alzheimer's Disease," Mt Sinai J Med, 2010, 77:82-102 (Exhibit 36).

Durand, Stéphanie and Andrea Cimarelli, "The Inside Out of Lentiviral Vectors," Viruses, 2011, 3:132-59 (Exhibit 37).

Ehrengruber, Markus U. et al., "Alphaviruses: Semliki Forest Virus and Sindbis Virus Vectors for Gene Transfer into Neurons," Current Protocols in Neuroscience, 2011, 57:4.22.1-27 (Exhibit 38).

Einav, Yulia et al., "Replication and episomal maintenance of Epstein-Barr virus-based vectors in mouse embryonal fibroblasts enable synthetic lethality screens," Molecular Cancer Therapeutics, 2003, 2:1121-8 (Exhibit 39).

Elder, Gregory A. et al., "Presenilin transgenic mice as models of Alzheimer's disease," Brain Struct Funct, 2010, 214:127-43 (Exhibit 40).

Elia, Lisa P. et al., "p120 Catenin Regulates Dendritic Spine and Synapse Development through Rho-Family GTPases and Cadherins," Neuron, 2006, 51:43-56 (Exhibit 41).

Ferrer, Isidro, "Altered mitochondria, energy metabolism, voltage-dependent anion channel, and lipid rafts converge to exhaust neurons in Alzheimer's disease," J Bioenerg Biomembr, 2009, 41:425-31 (Exhibit 42).

Follenzi, Antonia et al., "Gene transfer by lentiviral vectors is limited by nuclear translocation and rescued by HIV-1 pol sequences," Nature Genetics, 2000, 25:217-22 (Exhibit 43).

Francesconi, Anna et al., "Regulation of Group I Metabotropic Glutamate Receptor Trafficking and Signaling by the Caveolar/Lipid Raft Pathway," The Journal of Neuroscience, 2009, 29:3590-602 (Exhibit 44).

Gabbita, S. Prasad et al., "Aging and Caloric Restriction Affect Mitochondrial Respiration and Lipid Membrane Status: an Electron Paramagnetic Resonance Investigation," Free Radical Biology & Medicine, 1997, 23:191-201 (Exhibit 45).

Gabbita, S. Prasad et al., "Effects of mitochondrial respiratory stimulation on membrane lipids and proteins: an electron paramagnetic resonance investigation," Biochimica et Biophysica Acta, 1998, 1372:163-73 (Exhibit 46).

(56) References Cited

OTHER PUBLICATIONS

Gama Sosa, Miguel A. et al., "Age-Related Vascular Pathology in Transgenic Mice Expressing Presenilin 1-Associated Familial Alzheimer's Disease Mutations," *The American Journal of Pathology*, 2010, 176:353-68 (Exhibit 47).
Gan, Qingshen et al., "Long-term inducible expression in striatal neurons from helper virus-free HSV-1 vectors that contain the tetracycline-inducible promoter system," *Brain Res*, 2006, 1083:1-13 (Exhibit 48).
Gascón, Sergio et al., "Dual-promoter lentiviral vectors for constitutive and regulated gene expression in neurons," *Journal of Neuroscience Methods*, 2008, 168:104-12 (Exhibit 49).
Gaudreault, Sophie B. et al., "A role for caveolin-1 in post-injury reactive neuronal plasticity," *Journal of Neurochemistry*, 2005, 92:831-9 (Exhibit 50).
Gaudreault, Sophie B. et al., "Increased caveolin-1 expression in Alzheimer's disease brain," *Neurobiology of Aging*, 2004, 25:753-9 (Exhibit 51).
Gidday, Jeffrey M. et al., "Nitric Oxide Mediates Cerebral Ischemic Tolerance in a Neonatal Rat Model of Hypoxic Preconditioning," *Journal of Cerebral Blood Flow and Metabolism*, 1999, 19:331-40 (Exhibit 52).
Giles, K. E. et al., "Chromatin Boundaries, Insulators, and Long-Range Interactions in the Nucleus," *Cold Spring Harbor Symposia on Quantitative Biology*, 2010, 75:79-85 (Exhibit 53).
Gioiosa, Laura et al., "Altered emotionality, spatial memory and cholinergic function in caveolin-1 knock-out mice," *Behavioural Brain Research*, 2008, 188:255-62 (Exhibit 54).
Glenney, John R. Jr., "The sequence of human caveolin reveals identity with VIP21, a component of transport vesicles," *FEBS*, 1992, 314:45-8 (Exhibit 55).
Glover, Dominic J., "Artificial Viruses: Exploiting Viral Trafficking for Therapeutics," *Infectious Disorders—Drug Targets*, 2012, 12:68-80 (Exhibit 56).
Gonzales, Rueben A. et al., "N-Methyl-D-Aspartate Mediated Responses Decrease With Age in Fischer 344 Rat Brain," *Neurobiology of Aging*, 1991, 12:219-25 (Exhibit 57).
Gossen, Manfred and Hermann Bujard, "Tight control of gene expression in mammalian cells by tetracycline-responsive promoters," *Proc. Natl. Acad. Sci. USA*, 1992, 89:5547-51 (Exhibit 58).
Grider, M. H. et al., "Lipid Raft-Targeted Akt Promotes Axonal Branching and Growth Cone Expansion Via mTOR and Rac1, Respectively," *Journal of Neuroscience Research*, 2009, 87:303-342 (Exhibit 59).
Grove, Anna M. H. et al., "Reversible tetracycline-controlled activator (rtTA)-inducible expression of neuron-targeted Cav-1 and recovery after neuronal injury," *FASEB Journal*, 2010, 24:Abstract (Exhibit 60).
Guirland, Carmine and James Q. Zheng, "Membrane Lipid Rafts and Their Role in Axon Guidance," *Adv Exp Med Biol.*, 2007, 621:144-55 (Exhibit 61).
Guo, Xia and Leaf Huang, "Recent Advances in Nonviral Vectors for Gene Delivery," *Accounts of Chemical Research*, 2011, 45:971-9 (Exhibit 62).
Hardingham, Giles E. and Hilmar Bading, "The Yin and Yang of NMDA receptor signalling," *TRENDS in Neurosciences*, 2003, 26:81-89 (Exhibit 63).
Harland, Richard, "Neural induction," *Current Opinion in Genetics & Development*, 2000, 10:357-62 (Exhibit 64).
Harris, Benjamin et al., "Targeting ADAM10 to lipid rafts in neuroblastoma SH-SY5Y cells impairs amyloidogenic processing of the amyloid precursor protein," *Brain Research*, 2009, 1296:203-15 (Exhibit 65).
Hashimoto, Makoto et al., "a-Synuclein up-regulates expression of caveolin-1 and down-regulates extracellular signal-regulated kinase activity in B103 neuroblastoma cells: role in the pathogenesis of Parkinson's disease," *Journal of Neurochemistry*, 2003, 85:1468-79 (Exhibit 66).
Hattiangady, Bharathi et al. "Brain-derived neurotrophic factor, phosphorylated cyclic AMP response element binding protein and neuropeptide Y decline as early as middle age in the dentate gyrus and CA1 and CA3 subfields of the hippocampus," *Experimental Neurology*, 2005, 195:353-71 (Exhibit 67).
Hattori, Chinatsu et al., "BACE1 Interacts With Lipid Rafts Proteins," *Journal of Neuroscience Research*, 2006, 84:912-7 (Exhibit 68).
Head, Brian P. et al., "G-protein-coupled Receptor Signaling Components Localize in Both Sarcolemmal and Intracellular Caveolin-3-associated Microdomains in Adult Cardiac Myocytes," *The Journal of Biological Chemistry*, 2005, 280:31036-44 (Exhibit 69).
Head, Brian P. et al., "Microtubules and Actin Microfilaments Regulate Lipid Raft/Caveolae Localization of Adenylyl Cyclase Signaling Components," *The Journal of Biological Chemistry*, 2006, 281:26391-9 (Exhibit 70).
Head, Brian P. et al., "Caveolin-1 expression is essential for N-methyl-D-aspartate receptor-mediated Src and extracellular signal-regulated kinas ½ activation and protection of primary neurons from ischemic cell death," *The FASEB Journal*, 2008, 22:828-40 (Exhibit 71).
Head, Brian P. et al., "Inhibition of p75 Neurotrophin Receptor Attenuates Isoflurane-mediated Neuronal Apoptosis in the Neonatal Central Nervous System," *Anesthesiology*, 2009, 110:813-25 (Exhibit 72).
Head, Brian P. et al., "Loss of Caveolin-1 Accelerates Neurodegeneration and Aging," *PLoS One*, 2010, 5:e15697 (Exhibit 73).
Hebert, Liesi E. et al., "Alzheimer Disease in the US Population: Prevalence Estimates Using the 2000 Census," *Arch Neurol*, 2003, 60:1119-22 (Exhibit 74).
Hering, Heike et al., "Lipid Rafts in the Maintenance of Synapses, Dendritic Spines, and Surface AMPA Receptor Stability," *The Journal of Neuroscience*, 2003, 23:3262-71 (Exhibit 75).
Herschlag, Daniel et al., "The Importance of Being Ribose at the Cleavage Site in the Tetrahymena Ribozyme Reaction," *Biochemistry*, 1993, 32:8312-21 (Exhibit 76).
Heurteaux, Catherine et al., "Essential role of adenosine, adenosine A1 receptors, and ATP-sensitive $K^+$ channels in cerebral ischemic preconditioning," *Proc. Natl. Acad. Sci. USA*, 1995, 92:4666-70 (Exhibit 77).
Hibbert, Andrew P. et al., "The localization, trafficking and retrograde transport of BDNF bound to p75NTR in sympathetic neurons," *Molecular and Cellular Neuroscience*, 2006, 32:387-402 (Exhibit 78).
Hicks, R.R. et al., "Expression of trkB mRNA is altered in rat hippocampus after experimental brain trauma," *Molecular Brain Research*, 1998, 59:264-8 (Exhibit 79).
High, Katherine A. and Patrick Aubourg, "rAAV Human Trial Experience," *Methods in Molecular Biology*, 2011, 807:429-57 (Exhibit 80).
Hotulainen, Pirta and Casper C. Hoogenraad, "Actin in dendritic spines: connecting dynamics to function," *The Journal of Cell Biology*, 2010, 189:619-29 (Exhibit 81).
Huang, Jiakang and T. Jake Liang, "A Novel Hepatitis B Virus (HBV) Genetic Element with Rev Response Element-Like Properties That Is Essential for Expression of HBV Gene Products," *Molecular and Cellular Biology*, 1993, 13:7476-86 (Exhibit 82).
Huber, Andrea B. et al., "Signaling at the Growth Cone: Ligand-Receptor Complexes and the Control of Axon Growth and Guidance," *Annu. Rev. Neurosci.*, 2003, 26:509-63 (Exhibit 83).
Jasmin, Jean-Francois et al., "Caveolin-1 Deficiency Increases Cerebral Ischemic injury," *Circulation Research*, 2007, 100:721-9 (Exhibit 84).
Jasmin, Jean-Francois et al., "Genetic ablation of caveolin-1 increases neural stem cell proliferation in the subventricular zone (SVZ) of the adult mouse brain," *Cell Cycle*, 2009, 8:3978-83 (Exhibit 85).
Ju, Hong et al., "Direct Interaction of Endothelial Nitric-oxide Synthase and Caveolin-1 Inhibits Synthase Activity," *The Journal of Biological Chemistry*, 1997, 272:18522-5 (Exhibit 86).
Kafri, Tal et al., "Lentiviral Vectors: Regulated Gene Expression," *Molecular Therapy*, 2000, 1:516-21 (Exhibit 87).
Kannan, Madhuvanthi et al., "Mevastatin accelerates loss of synaptic proteins and neurite degeneration in aging cortical neurons in a heme-independent manner," *Neurobiology of Aging*, 2010, 31:1543-53 (Exhibit 88).

(56) References Cited

OTHER PUBLICATIONS

Kato, Shigeki et al., "Neuron-Specific Gene Transfer Through Retrograde Transport of Lentiviral Vector Pseudotyped with a Novel Type of Fusion Envelop Glycoprotein," *Human Gene Therapy*, 2011, 22:1511-23 (Exhibit 89).
Kerr, D. Steven et al., "Age-related changes in tolerance to the marine algal excitotoxin domoic acid," *Neuropharmacology*, 2002, 43:357-66 (Exhibit 90).
Kirkham, Matthew et al., "Evolutionary analysis and molecular dissection of caveola biogenesis," *Journal of Cell Science*, 2008, 121:2075-86 (Exhibit 91).
Koponen, J. K. et al., "Doxycycline-regulated lentiviral vector system with a novel reverse transactivator rtTA2$^S$-M2 shows a tight control of gene expression in vitro and in vivo," *Gene Therapy*, 2003, 10:459-66 (Exhibit 92).
Kumar, Bipin et al., "Mevastatin Induces Degeneration and Decreases Viability of cAMP-Induced Differentiated Neuroblastoma Cells in Culture by Inhibiting Proteasome Activity, and Mevalonic Acid Lactone Prevents These Effects," *Journal of Neuroscience Research*, 2002, 68:627-35 (Exhibit 93).
Kurzchalia, Teymuras V. et al., "VIP21, A 21-kD Membrane Protein is an Integral Component of Trans-Golgi-Network-Derived Transport Vesicles," *The Journal of Cell Biology*, 1992, 118:1003-14 (Exhibit 94).
Lee, Hyunjung et al., "Sustained delivery of thermostabilized chABC enhances axonal sprouting and functional recovery after spinal cord injury," *PNAS*, 2010, 107:3340-5 (Exhibit 95).
Lemkuil, Brian P. et al., "Isoflurane Neurotoxicity Is Mediated by p75$^{NTR}$-RhoA Activation and Actin Depolymerization," *Anesthesiology*, 2011, 114:49-57 (Exhibit 96).
Lentz, Thomas B. et al., "Viral vectors for gene delivery to the central nervous system," *Neurobiology of Disease*, 2012, 48:179-88 (Exhibit 97).
Li, Songlin et al., "An age-related sprouting transcriptome provides molecular control of axonal sprouting after stroke," *Nat Neurosci.*, 2010, 13:1496-504 (Exhibit 98).
Lim, Seung et al., "Exogenous gangliosides increase the release of brain-derived neurotrophic factor," *Neuropharmacology*, 2011, 60:1160-7 (Exhibit 99).
Lingwood, Daniel and Kai Simons, "Lipid Rafts As a Membrane-Organizing Principle," *Science*, 2010, 327:46-50 (Exhibit 100).
Lisanti, Michael P. et al., "Characterization of Caveolin-rich Membrane Domains Isolated from an Endothelial-rich Source: Implications for Human Disease," *The Journal of Cell Biology*, 1994, 126:111-26 (Exhibit 101).
Lisanti, Michael P. et al., "Caveolae, caveolin and caveolin-rich membrane domains: a signalling hypothesis," *Trends in Cell Biology*, 1994, 4:231-5 (Exhibit 102).
Loeb, Jonathan E. et al., "Enhanced Expression of Transgenes from Adeno-Associated Virus Vectors with the Woodchuck Hepatitis Virus Posttranscriptional Regulatory Element: Implications for Gene Therapy," *Human Gene Therapy*, 1999, 10:2295-305 (Exhibit 103).
Lufino, Michele M.P. et al., "Advances in High-capacity Extrachromosomal Vector Technology: Episomal Maintenance, Vector Delivery, and Transgene Expression," *Molecular Therapy*, 2008, 16:1525-38 (Exhibit 104).
Lufino, Michele M.P. et al., "Episomal Transgene Expression in Pluripotent Stem Cells," *Methods in Molecular Biology*, 2011, 767:369-87 (Exhibit 105).
MacArthur, Chad C. et al., "Chromatin Insulator Elements Block Transgene Silencing in Engineered Human Embryonic Stem Cell Lines at a Defined Chromosome 13 Locus," *Stem Cells and Development*, 2012, 21:191-205 (Exhibit 106).
MacDonald, Erin et al., "A Novel Phosphodiesterase Type 4 Inhibitor, HT-0712, Enhances Rehabilitation-Dependent Motor Recovery and Cortical Reorganization After Focal Cortical Ischemia," *Neurorehabilitation and Neural Repair*, 2007, 21:486-96 (Exhibit 107).

Magnusson, Kathy Ruth et al., "Age-related changes in the protein expression of subunits of the NMDA receptor," *Molecular Brain Research*, 2002, 99:40-5 (Exhibit 108).
Mateos, M. V. et al., "Selective localization of phosphatidylcholine-derived signaling in detergent-resistant membranes from synaptic endings," *Biochimica et Biophysica Acta*, 2010, 1798:624-36 (Exhibit 109).
Mauch, Daniela H. et al., "CNS Synaptogenesis Promoted by Glia-Derived Cholesterol," *Science*, 2001, 294:1354-7 (Exhibit 110).
Mermelstein, P. G., "Membrane-Localised Oestrogen Receptor and Influence Neuronal Activity Through Activation of Metabotropic Glutamate Receptors," *Journal of Neuroendocrinology*, 2009, 21:257-62 (Exhibit 111).
Monti, Barbara et al., "Alterations of markers related to synaptic function in aging rat brain, in normal conditions or under conditions of long-term dietary manipulation," *Neurochemistry International*, 2004, 44:579-84 (Exhibit 112).
Morgenstern, Peter F. et al., "Adeno-Associated Viral Gene Delivery in Neurodegenerative Disease," *Methods in Molecular Biology*, 2011, 793:443-55 (Exhibit 113).
Murray, Andrew J. et al., "cAMP-Dependent Axon Guidance Is Distinctly Regulated by Epac and Protein Kinase A," *The Journal of Neuroscience*, 2009, 29:15434-44 (Exhibit 114).
Murry, Charles E. et al., "Preconditioning with ischemia: a delay of lethal cell injury in ischemic myocardium," *Circulation*, 1986, 74:1124-36 (Exhibit 115).
Neumann, Simone et al., "Regeneration of Sensory Axons within the Injured Spinal Cord Induced by Intraganglionic cAMP Elevation," *Neuron*, 2002, 34:885-93 (Exhibit 116).
Nishio, Shinsaku et al., "Ischemic tolerance in the rat neocortex following hypothermic preconditioning," *J Neurosurg*, 2000, 93:845-51 (Exhibit 117).
Norris, Christopher M. et al., "Reversal of Age-Related Alterations in Synaptic Plasticity by Blockade of L-Type $Ca^{2+}$Channels," *The Journal of Neuroscience*, 1998, 18:3171-9 (Exhibit 118).
Oshikawa, Jin et al., "Nicotinic acetylcholine receptor $\alpha_7$, regulates cAMP signal within lipid rafts," *Am J Physiol Cell Physiol.*, 2003, 285:C567-74 (Exhibit 119).
Park, David S. et al., "Caveolin-1 Null (-/-) Mice Show Dramatic Reductions in Life Span," *Biochemistry*, 2003, 42:15124-31 (Exhibit 120).
Patterson, Susan L. et al., "Recombinant BDNF Rescues Deficits in Basal Synaptic Transmission and Hippocampal LTP in BDNF Knockout Mice," *Neuron*, 1996, 16:1137-45 (Exhibit 121).
Peri, Alessandro and Mario Serio, "Neuroprotective effects of the Alzheimer's disease-related gene seladin-1," *Journal of Molecular Endocrinology*, 2008, 41:251-61 (Exhibit 122).
Pike, Linda J., "The challenge of lipid rafts," *Journal of Lipid Research*, 2009, 50:S323-8 (Exhibit 123).
Poo, Mu-ming, "Neurotrophins as Synaptic Modulators," *Nature Reviews*, 2001, 2:24-32 (Exhibit 124).
Razani, Babak et al., "Caveolae: From Cell Biology to Animal Physiology," *Pharmacological Reviews*, 2002, 54:431-67 (Exhibit 125).
Renner, Marianne et al., "Control of the Postsynaptic Membrane Viscosity," *The Journal of Neuroscience*, 2009, 29:2926-37 (Exhibit 126).
Rubino, Annalisa and Derek M. Yellon, "Ischaemic preconditioning of the vasculature: an overlooked phenomenon for protecting the heart?," *TiPS*, 2000, 21:225-30 (Exhibit 127).
Samhan-Arias, Alejandro K. et al., "Clustering of plasma membrane-bound cytochrome $b_5$ reductase within 'lipid raft' microdomains of the neuronal plasma membrane," *Molecular and Cellular Neuroscience*, 2009, 40:14-26 (Exhibit 128).
Saneyoshi, Takeo et al., "Activity-Dependent Synaptogenesis: Regulation by a CaM-Kinase Kinase/CaM-Kinase I/βPIX Signaling Complex," *Neuron*, 2008, 57:94-107 (Exhibit 129).
Sauerwald, Angela et al., "The 5'-Flanking Region of the Synapsin I Gene," *The Journal of Biological Chemistry*, 1990, 265:14932-7 (Exhibit 130).

(56) References Cited

OTHER PUBLICATIONS

Schaller, B. J., "Influence of age on stroke and preconditioning-induced ischemic tolerance in the brain," *Experimental Neurology*, 2007, 205:9-19 (Exhibit 131).
Scherer, Philipp E. et al., "Identification, sequence, and expression of caveolin-2 defines a caveolin gene family," *Proc. Natl. Acad. Sci. USA*, 1996, 93:131-5 (Exhibit 132).
Shapira, Shlomo et al., "Aging has a complex effect on a rat model of ischemic stroke," *Brain Research*, 2002, 925:148-58 (Exhibit 133).
Smart, Eric J. et al., "Caveolins, Liquid-Ordered Domains, and Signal Transduction," *Molecular and Cellular Biology*, 1999, 19:7289-304 (Exhibit 134).
Sotgia, Federica et al., "Caveolin-1 Deficiency (-/-) Conveys Pre-malignant Alterations in Mammary Epithelia, with Abnormal Lumen Formation, Growth Factor Independence, and Cell Invasiveness," *American Journal of Pathology*, 2006, 168:292-309 (Exhibit 135).
Sparrow, J. R. et al., "Antibodies to Gangliosides Inhibit Goldfish Optic Nerve Regeneration In Vivo," *Journal of Neuroscience Research*, 1984, 12:233-43 (Exhibit 136).
Stefani, Massimo and Gianfranco Liguri, "Cholesterol in Alzheimer's Disease: Unresolved Questions," *Current Alzheimer Research*, 2009, 6:15-29 (Exhibit 137).
Stern, Christopher M. and Paul G. Mermelstein, "Caveolin regulation of neuronal intracellular signaling," *Cell Mol. Life Sci.*, 2010, 67:3785-95 (Exhibit 138).
Suzuki, Kunihiko, "Evaluation of the Extraction Procedures, Post-Mortem Changes and the Effect of Formalin Preservation," *Journal of Neurochemistry*, 1965, 12:629-38 (Exhibit 139).
Suzuki, Shingo et al., "BDNF-induced recruitment of TrkB receptor into neuronal lipid rafts: roles in synaptic modulation," *The Journal of Cell Biology*, 2004, 167:1205-15 (Exhibit 140).
Suzuki, Shingo et al., "Brain-Derived Neurotrophic Factor Regulates Cholesterol Metabolism for Synapse Development," *The Journal of Neuroscience*, 2007, 27:6417-27 (Exhibit 141).
Suzumura, Akio et al., "Roles of Glia-Derived Cytokines on Neuronal Degeneration and Regeneration," *Ann. N. Y. Acad. Sci.*, 2006, 1088:219-29 (Exhibit 142).
Svennerholm, Lars, "Composition of Gangliosides from Human Brain," *Nature*, 1956, 177:524-5 (Exhibit 143).
Takayasu, Yukihiro et al., "Caveolin-1 knockout mice exhibit impaired induction of mGluR-dependent long-term depression at CA3-CA1 synapses," *PNAS*, 2010, 107:21778-83 (Exhibit 144).
Tamaru, Masao et al., "Age-related decreases of the N-methyl-D-aspartate receptor complex in the rat cerebral cortex and hippocampus," *Brain Research*, 1991, 542:83-90 (Exhibit 145).
Tang, ZhaoLan et al., "The primary sequence of murine caveolin reveals a conserved consensus site for phosphorylation by protein kinase C," *Gene*, 1994, 147:299-300 (Exhibit 146).
Tang, ZhaoLan et al., "Molecular Cloning of Caveolin-3, a Novel Member of the Caveolin Gene Family Expressed Predominantly in Muscle," *The Journal of Biological Chemistry*, 1996, 271:2255-61 (Exhibit 147).
Tang, ZhaoLan et al., "Identification, Sequence, and Expression of an Invertebrate Caveolin Gene Family from the Nematode *Caenorhabditis elegans*," *The Journal of Biological Chemistry*, 1997, 272:2437-45 (Exhibit 148).
Thibault, Olivier et al., "Calcium dysregulation in neuronal aging and Alzheimer's disease: history and new directions," *Cell Calcium*, 1998, 24:417-33 (Exhibit 149).
Toescu, Emil C. et al., "Ca2+ regulation and gene expression in normal brain aging," *TRENDS in Neurosciences*, 2004, 27:614-20 (Exhibit 150).
Tolmachov, Oleg E., "Building Mosaics of Therapeutic Plasmid Gene Vectors," *Current Gene Therapy*, 2011, 11:466-78 (Exhibit 151).
Trushina, Eugenia et al., "Neurological abnormalities in caveolin-1 knock out mice," *Behavioural Brain Research*, 2006, 172:24-32 (Exhibit 152).
Vanmierlo, Tim et al., "Alterations in Brain Cholesterol Metabolism in the APPSLxPS1mut mouse, a Model for Alzheimer's Disease," *Journal of Alzheimer's Disease*, 2010, 19:117-27 (Exhibit 153).
Vetrini, Francesco and Philip Ng, "Gene Therapy with Helper-Dependent Adenoviral Vectors: Current Advances and Future Perspectives," *Viruses*, 2010, 2:1886-917 (Exhibit 154).
Wang, Lijun et al., "Production and Purification of Recombinant Adeno-Associated Vectors," *Methods in Molecular Biology*, 2011, 807:361-404 (Exhibit 155).
Wayman, Gary A. et al., "Activity-Dependent Dendritic Arborization Mediated by CaM-Kinase I Activation and Enhanced CREB-Dependent Transcription of Wnt-2," *Neuron*, 2006, 50:897-909 (Exhibit 156).
Williams, Terence M. and Michael P. Lisanti, "The caveolin proteins," *Genome Biology*, 2004, 5:214 (Exhibit 157).
Williams, Terence M. et al., "Caveolin-1 Gene Disruption Promotes Mammary Tumorigenesis and Dramatically Enhances Lung Metastasis in Vivo," *The Journal of Biological Chemistry*, 2004, 279:51630-46 (Exhibit 158).
Willmann, Raffaella et al., "Cholesterol and lipid microdomains stabilize the postsynapse at the neuromuscular junction," *The EMBO Journal*, 2006, 25:4050-60 (Exhibit 159).
Yam, Priscilla Y. et al., "Design of HIV Vectors for Efficient Gene Delivery into Human Hematopoietic Cells," *Molecular Therapy*, 2002, 5:479-84 (Exhibit 160).
Yamashita, Tadashi et al., "Interruption of ganglioside synthesis produces central nervous system degeneration and altered axon-glial interactions," *PNAS*, 2005, 102:2725-30 (Exhibit 161).
Yoon, Il-Sang et al., "Low-density lipoprotein receptor-related protein promotes amyloid precursor protein trafficking to lipid rafts in the endocytic pathway," *The FASEB Journal*, 2007, 21:2742-52 (Exhibit 164).

\* cited by examiner

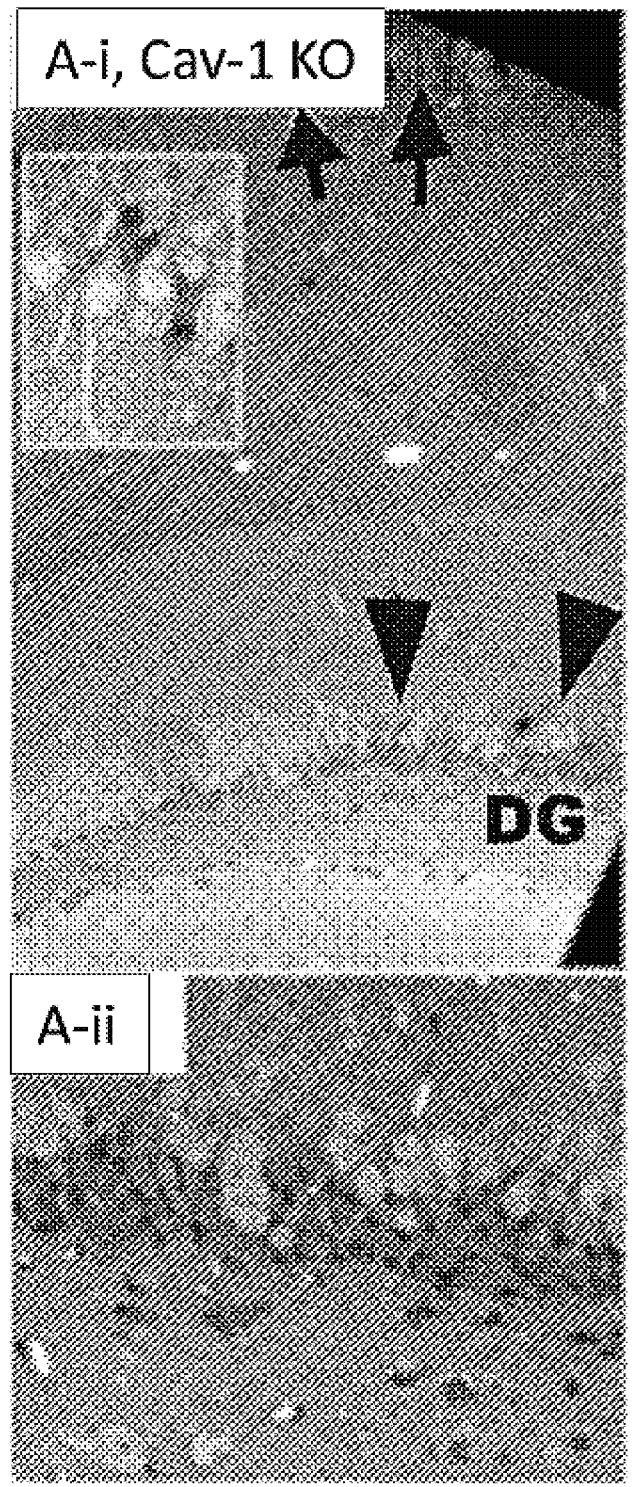
FIG. 5A(i-ii)

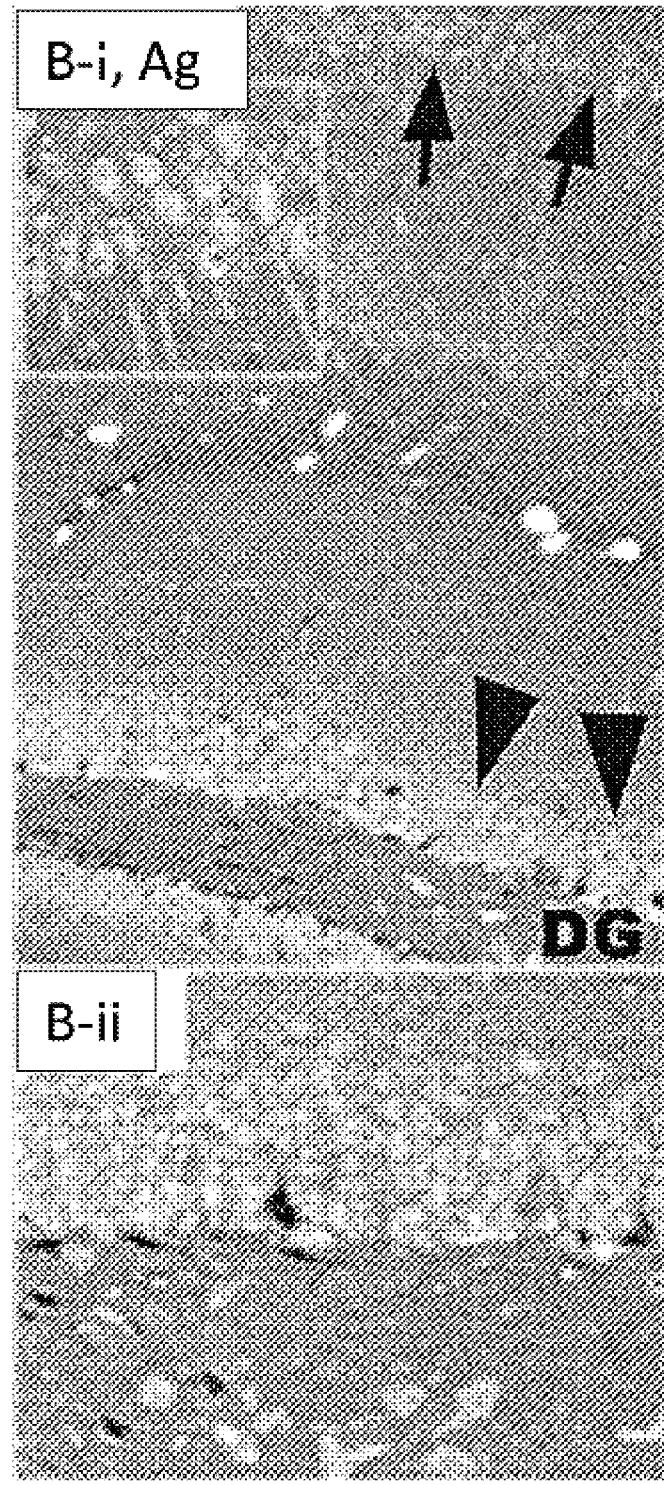
FIG. 5B (i-ii)

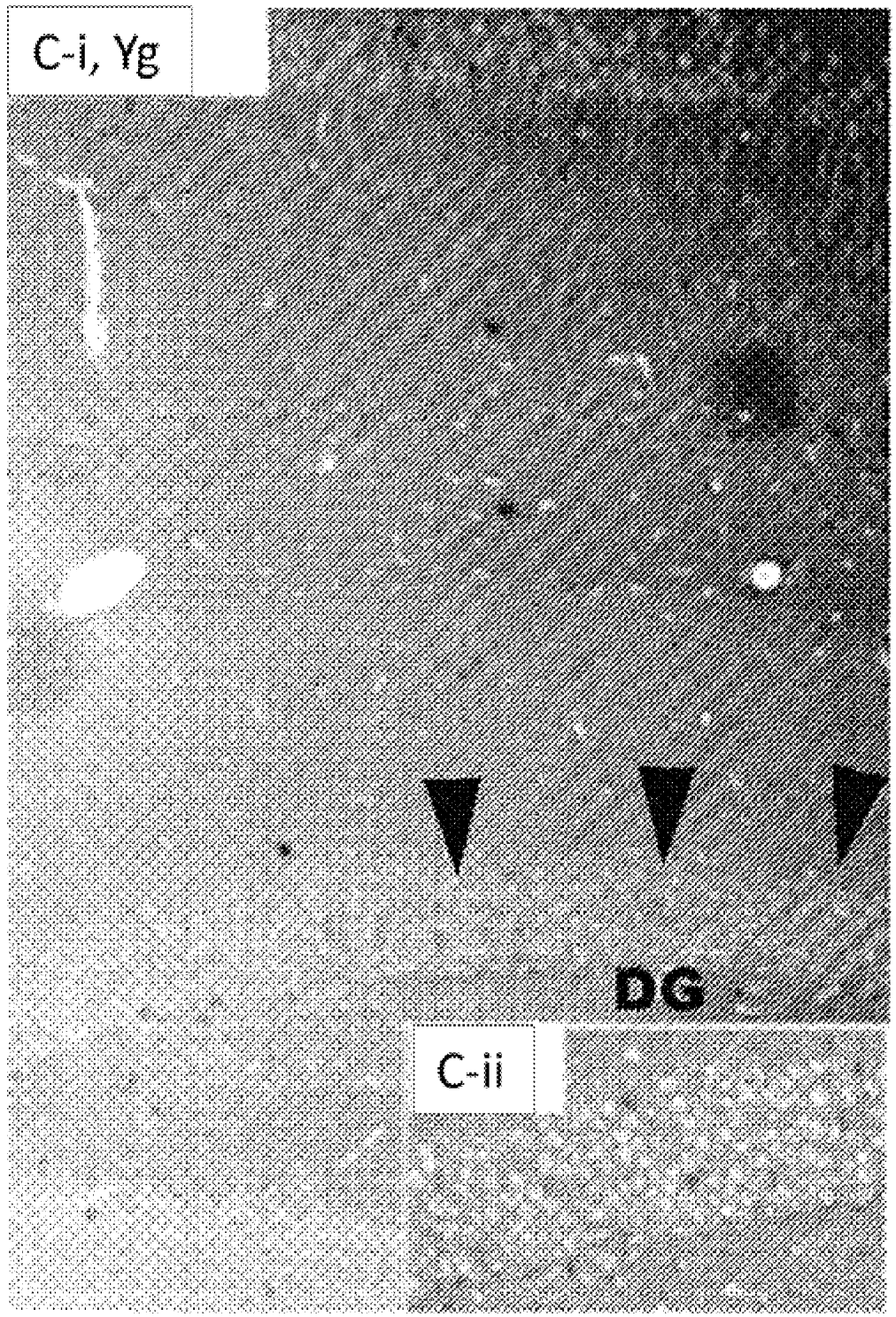
*FIG. 5C (i-ii)*

Sequence of Syn promoter-Cav1
Synapsin promoter: Blue
Caveolin-1: Red

ACGCGTATCGATGGCGCCAGCTGCAGAGGGCCCTGCGTATGAGTG
CAAGTGGGTTTTAGGACCAGGATGAGGCGGGGTGGGGGTGCCTACCTG
ACGACCGACCCCGACCCACTGGACAAGCACCCAACCCCCATTCCCCAA
ATTGCGCATCCCCTATCAGAGAGGGGGAGGGGAAACAGGATGCGGCG
AGGCGCGTGCGCACTGCCAGCTTCAGCACCGCGGACAGTGCCTTCGCC
CCCGCCTGGCGGCGCGCGCCACCGCCGCCTCAGCACTGAAGGCGCGCT
GACGTCACTCGCCGGTCCCCCGCAAACTCCCCTTCCCGGCCACCTTGGT
CGCGTCCGCGCCGCCGCCGGCCCAGCCGGACCGCACCACGCGAGGCGC
GAGATAGGGGGCACGGGCGCGACCATCTGCGCTGCGGCGCCGGCGAC
TCAGCGCTGCCTCAGTCTGCGGTGGGCAGCGGAGGAGTCGTGTCGTGC
CTGAGAGCGCAGTCGACGGTACCGCGGGCCCAAACGAATTCGCCCTTC
CAGGGAAACCTCCTCAGAGCCTGCAGCCAGCCACGCGCCAGCATGTCT
GGGGGCAAATACGTAGACTCCGAGGGACATCTCTACACTGTTCCCATCC
GGGAACAGGGCAACATCTACAAGCCCAACAACAAGGCCATGGCAGAC
GAGGTGACTGAGAAGCAAGTGTATGACGCGCACACCAAGGAGATTGAC
CTGGTCAACCGCGACCCCAAGCATCTCAACGACGACGTGGTCAAGATT
GACTTTGAAGATGTGATTGCAGAACCAGAAGGGACACACAGTTTCGAC
GGCATCTGGAAGGCCAGCTTCACCACCTTCACTGTGACAAAATATTGG
TTTTACCGCTTGTTGTCTACGATCTTCGGCATCCCAATGGCACTCATCTG
GGGCATTTACTTTGCCATTCTCTCCTTCCTGCACATCTGGGCGGTTGTAC
CGTGCATCAAGAGCTTCCTGATTGAGATTCAGTGCATCAGCCGCGTCTA
CTCCATCTACGTCCATACCTTCTGCGATCCACTCTTTGAAGCTATTGGC
AAGATATTCAGCAACATCCGCATCAGCACGCAGAAAGAGATATTAGGG
ACATTTCAAGGATGAAAGGTTTTTTTCCCCCCTTACTATTTCCTTGGTGC
CAATTCCAAGTTGCTCTCGCAGAAGGGCGAATTCGCGGCCGC

FIG. 8

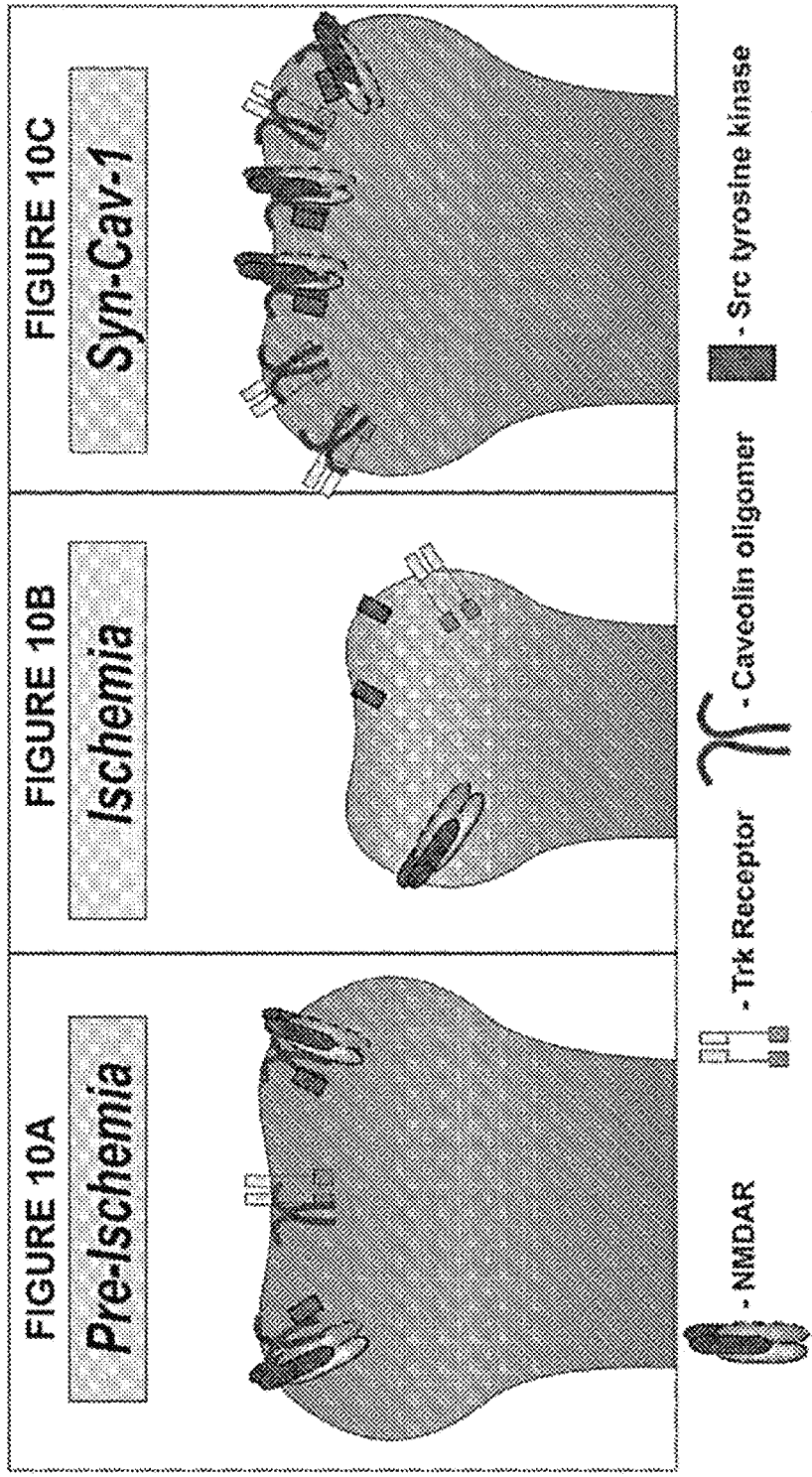

Figure. Schematic depicting the organization of ionotropic glutamate and neurotrophin receptors by Cav-1 in synaptic regions in neurons. A) Normal neurons show Cav-1 oligomers organizing N-methyl-D-aspartate receptors (NMDAR), tropomyosin kinase receptors (TrkR), and Src tyrosine kinases in synaptic regions. B) Following lethal ischemia, there is a drastic reduction in Cav-1, synapses, and functional receptors. C) Re-expression of Cav-1 driven by a neuronal specific synapsin promoter (Syn-Cav-1) enhances expression of glutamate and neurotrophin receptors and improves neuroprotective signaling in the central nervous system.

FIG. 10A-C

NEURONAL SPECIFIC TARGETING OF CAVEOLIN EXPRESSION TO RESTORE SYNAPTIC SIGNALING AND IMPROVE COGNITIVE FUNCTION IN THE NEURODEGENERATIVE BRAIN AND MOTOR FUNCTION IN SPINAL CORD

This application is a divisional of U.S. Ser. No. 13/883,503, filed May 3, 2013 (now U.S. Pat. No. 8,969,077), which is a 35 U.S.C. § 371 application of PCT application No. PCT/US2011/059635, filed Nov. 7, 2011, which claimed the priority of U.S. Ser. No. 61/456,425, filed Nov. 5, 2010, the contents of all of which are hereby incorporated by reference in their entirety into the present application.

Throughout this application various publications are referenced. The disclosures of these publications in their entirety are hereby incorporated by reference into this application in order to more fully describe the state of the art to which this invention pertains.

STATEMENT REGARDING FEDERALLY SPONSORED RESEARCH

This invention was made with Government support under Grant No. NS073653, awarded by the National Institutes of Health. The Government has certain rights in the invention.

BACKGROUND OF THE INVENTION

Cognitive decline is emerging as one of the greatest health problems in the elderly population. [1,2] Age alone increases the risk of stroke, Alzheimer's disease (AD), and other forms of dementia [2]. The risk of AD increases 14-fold between the ages of 65-85, and affects almost 47% over the age of 85 [3], Multiple signaling pathways regulate neuronal survival and growth to facilitate the formation of synapses and this signaling is altered with age [4,5,6,7], Synapses are essential for learning, memory and the development of neurons in the CNS [8]. Receptors and associated proteins aggregate to mold and shape post-synaptic densities in order to permit high fidelity signal transduction leading to rapid regulation of neuronal function [9,10, 11]. Understanding the basic pathophysiological mechanisms of cognitive decline and how the subcellular organization of signaling molecules is altered with cognitive decline could potentially yield novel therapeutic targets for neuronal aging and neurodegeneration.

Cholesterol is a major lipid component of synapses and a limiting factor in synapse development, synaptic activity, and neurotransmitter release [12]. Age-related impairments in the biosynthesis, transport, or uptake of cholesterol by neurons in the CNS may adversely affect development, plasticity, and synaptic circuitry associated with neurodegenerative diseases [13,14,15,16,17], Membrane lipid rafts (MLR), discrete regions of the plasma membrane enriched in cholesterol, glycosphingolipids and sphingomyelin, are essential for synapse development, stabilization, and maintenance [12,18]. Moreover, caveolin-1 (Cav-1), a cholesterol binding and resident protein of MLR [19,20,21], organizes and targets synaptic components of the neurotransmitter and neurotrophic receptor signaling pathways to MLR [e.g., NMDAR, AMPAR, TrkR, Src Family Kinases (SFK)] [22,23,24,25,26,27]. Additionally, neurotransmitter and neurotrophic receptors are found within MLR in growth cones, a finding that has major implications for neuronal plasticity [11,28].

Early-onset AD, which afflicts individuals prior to 60-65 years of age, is known to be caused by mutations in three genes: amyloid precursor protein (APP), presenilin-1, and presenilin-2 [29]. MLR and cholesterol play a protective role against APP processing and amyloid-β (Aβ) toxicity [13,14,16,30,31,32,33]. Cav-1 KO mice develop CNS pathology similar to AD, such as altered NMDA receptor signaling, motor and behavioral abnormalities, increased ischemic cerebral injury, impaired spatial memory, and cholinergic function [27,34,35,36]. Whether MLR, Cav-1 expression, and the organization of pro-survival and pro-growth signaling mechanisms are altered in neurodegenerative states (age-related dementia and AD) has yet to be investigated. The present study tested whether 1) Cav-1 organizes synaptic signaling components in neuronal MLR and synaptosomes, 2) the localization of synaptic signaling components to neuronal MLR and synaptosomes is reduced in brains from aged wild-type and young Cav-1 KO mice, and 3) brains from Cav-1 KO mice develop a neuropathological phenotype similar to Alzheimer's disease.

The aged brain exhibits a loss in gray matter and a decrease in spines and synaptic densities that may represent a sequela for neurodegenerative diseases such as Alzheimer's. Membrane/lipid rafts (MLR), discrete regions of the plasmalemma enriched in cholesterol, glycosphingolipids, and sphingomyelin, are essential for the development and stabilization of synapses. Caveolin-1 (Cav-1), a cholesterol binding protein organizes synaptic signaling components within MLR. It is unknown whether loss of synapses is dependent on an age-related loss of Cav-1 expression and whether this has implications for neurodegenerative diseases such as Alzheimer's disease. We analyzed brains from young (Yg, 3-6 months), middle age (Md, 12 months), aged (Ag, >18 months), and young Cav-1 KO mice and show that localization of PSD-95, NR2A, NR2B, TrkBR, AMPAR, and Cav-1 to MLR is decreased in aged hippocampi. Young Cav-1 KO mice showed signs of premature neuronal aging and degeneration. Hippocampi synaptosomes from Cav-1 KO mice showed reduced PSD-95, NR2A, NR2B, and Cav-1, an inability to be protected against cerebral ischemia-reperfusion injury compared to young WT mice, increased Aβ, P-Tau, and astrogliosis, decreased cerebrovascular volume compared to young WT mice. As with aged hippocampi, Cav-1 KO brains showed significantly reduced synapses. Neuron-targeted re-expression of Cav-1 in Cav-1 KO neurons in vitro decreased Aβ expression. Therefore, Cav-1 represents a novel control point for healthy neuronal aging and loss of Cav-1 represents a non-mutational model for Alzheimer's disease.

Decreased expression of pro-survival and growth-stimulatory pathways, in addition to an environment that inhibits neuronal growth, contribute to the limited regenerative capacity in the central nervous system following injury or neurodegeneration. Membrane/lipid rafts, plasmalemmal microdomains enriched in cholesterol, sphingolipids, and the protein caveolin (Cav), are essential for synaptic development/stabilization and neuronal signaling. Cav-1 concentrates glutamate and neurotrophin receptors and pro-survival kinases, and regulates cAMP formation. Here, we show that primary neurons that express a synapsin-driven Cav-1 vector (SynCav1) have increased raft formation, neurotransmitter and neurotrophin receptor expression, NMDA- and BDNF-mediated pro-survival kinase activation, agonist-stimulated cAMP formation, and dendritic growth. Moreover, expression of SynCav1 in Cav-1 KO neurons restores NMDA- and BDNF-mediated signaling and enhances dendritic growth. The enhanced dendritic growth occurred even in the presence of inhibitory cytokines (TNFα, IL-1β) and myelin-associated glycoproteins (MAG, Nogo). Targeting of Cav-1 to neurons thus enhances pro-survival and pro-growth signaling and may be a novel means to repair the injured and neurodegenerative brain.

Multiple signaling pathways have been identified that promote growth and survival of neurons and thereby facilitate the formation of synaptic connections that are essential for learning, memory, and the development of the CNS (Toescu, E. C., Verkhratsky, A., and Landfield, P. W. (2004) Trends Neurosci 27, 614-620; Hattiangady, B., Rao, M. S., Shetty, G. A, and Shetty, A. K. (2005) Exp Neurol 195, 353-371; Hotulainen, P., and Hoogenraad, C. C. (2010) J Cell Biol 189, 619-629). Neurotransmitter and neurotrophic receptors, non-receptor tyrosine kinases and other signaling mediators aggregate to mold and shape postsynaptic densities in order to permit high-fidelity signal transduction and the regulation of neuronal function (Huber, A, B., Kolodkin, A, L., Ginty, D. D., and Cloutier, 1 F. (2003) Annu Rev Neurosci 26, 509-563; Calabrese, B., Wilson, M. S., and Halpain, S. (2006) Physiology (Bethesda) 21, 38-47; Guirland, C., and Zheng, J. Q. (2007) Adv Exp Med Biol 621, 144-155). A major non-protein component of synapses is cholesterol, which can be a limiting factor in synapse development, synaptic activity, and transmitter release (Mauch, D. H., Nagler, K., Schumacher, S., Goritz, C., Muller, E, C., Otto, A., and Pfrieger, F. W. (2001) Science 294, 1354-1357).

Increasing evidence shows that membrane/lipid rafts, discrete regions of the plasma membrane enriched in cholesterol, glycosphingolipids and sphingomyelin, organize pro-survival and pro-growth neuronal signaling pathways (Allen, J. A., Halverson-Tamboli, R. A., and Rasenick, M. M. (2007) Nat Rev Neurosci 8, 128-140; Head, B. P., Patel, H. H., Tsutsumi, Y. M., Hu, Y., Mejia, T., Mora, R. C., Insel, P. A., Roth, D. M., Drummond, J. C., and Patel, P. M. (2008) Faseb J 22, 828-840; Stern, C. M., and Mermelstein, P. G. (2010) Cell Mol Life Sci 67, 3785-3795), regulate cAMP formation (Oshikawa, J., Toya, Y., Fujita, T., Egawa, M., Kawabe, J., Umemura, S., and Ishikawa, Y. (2003) Am J Physiol Cell Physiol 285, C567-574), and are essential for synapse development, stabilization, and maintenance (Mauch, D. H., Nagler, K., Schumacher, S., Goritz, C., Muller, E. C., Otto, A., and Pfrieger, F. W. (2001) Science 294, 1354-1357; Willmann, R., Pun, S., Stallmach, L., Sadasivam, G., Santos, A. F., Caroni, P., and Fuhrer, C. (2006) Embo J 25, 4050-4060). Caveolin (Cav), a cholesterol binding protein and scaffolding protein found within membrane/lipid rafts (Smart, E. J., Graf, G. A., McNiven, M. A., Sessa, W. C., Engelman, J. A., Scherer, P. E., Okamoto, T., and Lisanti, M. P. (1999) Mol Cell Biol 19, 7289-7304), organizes and targets certain neuronal growth-promoting proteins, such as components of the neurotransmitter and neurotrophic receptor signaling pathways, to membrane/lipid rafts; these include NMDAR, AMPAR, TrkR, GPCRs, Src Family Kinases (SFK)] (Head, B. P., Patel, H. H., Tsutsumi, Y. M., Hu, Y., Mejia, T., Mora, R. C., Insel, P. A., Roth, D. M., Drummond, J. C., and Patel, P. M. (2008) Faseb J 22, 828-840; Bilderback, T. R., Gazula, V. R., Lisanti, M. P., and Dobrowsky, R. T. (1999) J Biol Chem 274, 257-263; Hibbert, A. P., Kramer, B. M., Miller, F. D., and Kaplan, D. R. (2006) Mol Cell Neurosci 32, 387-402; Bjork, K., Sjogren, B., and Svenningsson, P. (2010) Exp Cell Res 316, 1351-1356). These receptors and signaling molecules can enhance cAMP formation, an essential second messenger for promoting neuronal growth and dendritic arborization (Neumann, S., Bradke, F., Tessier-Lavigne, M., and Basbaum, A. I. (2002) Neuron 34, 885-893; Wayman, G. A., Impey, S., Marks, D., Saneyoshi, T., Grant, W. F., Derkach, V., and Soderling, T. R. (2006) Neuron 50, 897-909; MacDonald, E., Van der Lee, H., Pocock, D., Cole, C., Thomas, N., VandenBerg, P. M., Bourtchouladze, R., and Kleim, J. A. (2007) Neurorehabil Neural Repair 21, 486-496; Saneyoshi, T., Wayman, G., Fortin, D., Davare, M., Hoshi, N., Nozaki, N., Natsume, T., and Soderling, T. R. (2008) Neuron 57, 94-107; Murray, A. J., Tucker, S. J., and Shewan, D. A. (2009) J Neurosci 29, 15434-15444) and are found within membrane/lipid rafts in growth cones (Guirland, C., and Zheng, J. Q. (2007) Adv Exp Med Biol 621, 144-155). In the setting of traumatic brain injury and neurodegenerative disorders, interventions that activate signaling pathways to stimulate cAMP production thus have the potential to improve functional recovery in such settings (MacDonald, E., Van der Lee, H., Pocock, D., Cole, C., Thomas, N., VandenBerg, P. M., Bourtchouladze, R., and Kleim, J. A. (2007) Neurorehabil Neural Repair 21, 486-496; Atkins, C. M., Oliva, A. A., Jr., Alonso, O. F., Pearse, D. D., Bramlett, H. M., and Dietrich, W. D. (2007) Exp Neurol 208, 145-158).

A major problem following brain injury (e.g., stroke or trauma) and neurodegeneration is limited functional recovery as a consequence of a reduction in signaling that promotes neuronal growth and survival (Atkins, C. M., Oliva, A. A., Jr., Alonso, O. F., Pearse, D. D., Bramlett, H. M., and Dietrich, W. D. (2007) Exp Neurol 208, 145-158; Hicks, R. R., Zhang, L., Dhillon, H. S., Prasad, M. R., and Seroogy, K. B. (1998) Brain Res Mol Brain Res 59, 264-268; Biegon, A., Fry, P. A., Paden, C. M., Alexandrovich, A., Tsenter, J., and Shohami, E. (2004) Proc Natl Acad Sci USA 101, 5117-5122; Atkins, C. M., Falo, M. C., Alonso, O. F., Bramlett, H. M., and Dietrich, W. D. (2009) Neurosci Lett 459, 52-56), This loss of "protective signaling" increases neuronal loss, impairs brain repair, and increases functional deficits. Therapeutic interventions, such as addition of growth factors or approaches to increase cAMP, are relatively ineffective because of the loss of key receptors and their downstream signaling molecules. Therefore, interventions that restore pro-growth and pro-survival signaling within neurons have the potential not only to reduce neuronal loss and enhance endogenous brain repair, but also to increase the efficacy of pharmacologic agents designed to improve functional outcome (Carmichael, S. T. (2008) Stroke 39, 1380-1388).

We show that over-expression of neuron-targeted Cav-1 in primary neurons enhances expression of membrane/lipid rafts, neurotransmitter and neurotrophin receptors and increases pro-growth signaling, cAMP production, and dendritic growth and arborization. Conversely, siRNA-mediated loss of Cav-1 decreases membrane/lipid rafts and expression of neurotransmitter and neurotrophin receptors, and blunts NMDA- and BDNF-mediated signaling and attenuates agonist-stimulated cAMP production. Re-expression of Cav-1 in Cav-1 KO primary neurons restores pro-survival signaling and promotes neuronal growth and arborization even in the presence of inhibitory cytokines and myelin-associated glycoproteins. These growth-promoting effects of neuron-targeted Cav-1 expression suggest that it might be useful as a therapeutic intervention to limit neurodegeneration and to enhance repair of the injured CNS.

SUMMARY OF THE INVENTION

The invention provides an expression system for producing Caveolin-1 in neuronal cells or neural stem cells comprising a neuron-specific regulatory element and a nucleic acid sequence encoding Caveolin-1.

The invention also provides methods for promoting neural cell growth comprising administering Caveolin-1 or portion thereof to neural cells in a sufficient amount so as to promote neural cell growth

DESCRIPTION OF THE FIGURES

FIG. 5A-E shows Cav-1 KO mice exhibit enhanced astrogliosis and neuronal degeneration. (A-C) Light microscopic image displaying 0.5 μm thick hippocampal sections of Cav-1 KO (A-i, A-ii), aged (B-i, B-ii), and young (C-i, C-ii) stained with toludine blue. There is a drastic reduction in neurons within the dentate gyms (large arrow heads) and CA1 regions (arrows) of young Cav-1 KO mice compared to young and aged WT. In addition, there appears to be the presence of more glia and glial scar formation within the dentate gyms of Cav-1 KO mice as indicated by the darker gray cell bodies intermixed with the neurons. (D) Hippocampal coronal cryostat sections (10 μm) from WT and Cav-1 KO mice were stained with Nissl (neuronal marker, red pixels) and GFAP (astrocyte marker, green) to show no overlap between neurons and astrocytes (#$p<0.05$). (E) Coronal cryostat sections (25 um) of 2 month WT, 2 month Cav-1 KO and 12 month Cav-1 KO stained with 0.0004% Flouro-Jade®B and fluorescent red Nissl with DAPI. Areas from CA1 of the hippocampus were imaged. WT CA1 showed well-organized astrocytes. Two month Cav-1 KO had areas of disorganized astrocytes with lightly labeling areas of potential future plaque development. Twelve month Cav-1 KO CA1 areas had large bright, entangled green fluorescence with red neurons inside and significantly less organized astrocytes, further demonstrating a degenerating neuronal model.

FIG. 8 shows the sequence for synapin-caveolin-1 (SynCav1) (SEQ ID NO:1). The synapsin promoter along with cloning sites are notated in blue and the caveolin-1 gene is notated in red. The start (ATG) and stop (TGA) codons are notated in brownish-orange font and highlighted with yellow. Underlined green or green/blue fonts a restriction enzyme cleavage site that can be used to isolate the entire SynCav1 DNA fragment (e.g., MluI and NotI), Syn promoter DNA fragment (e.g., MluI and SalI), Cav1 encoding DNA fragment (e.g., SalI and NotI). Since these restriction cleavage sites are part of several multiple cloning sites (MCS), other restriction enzymes that can serve a similar purpose are found within the proximity of the underlined green or green/blue fonts.

Figure 1:
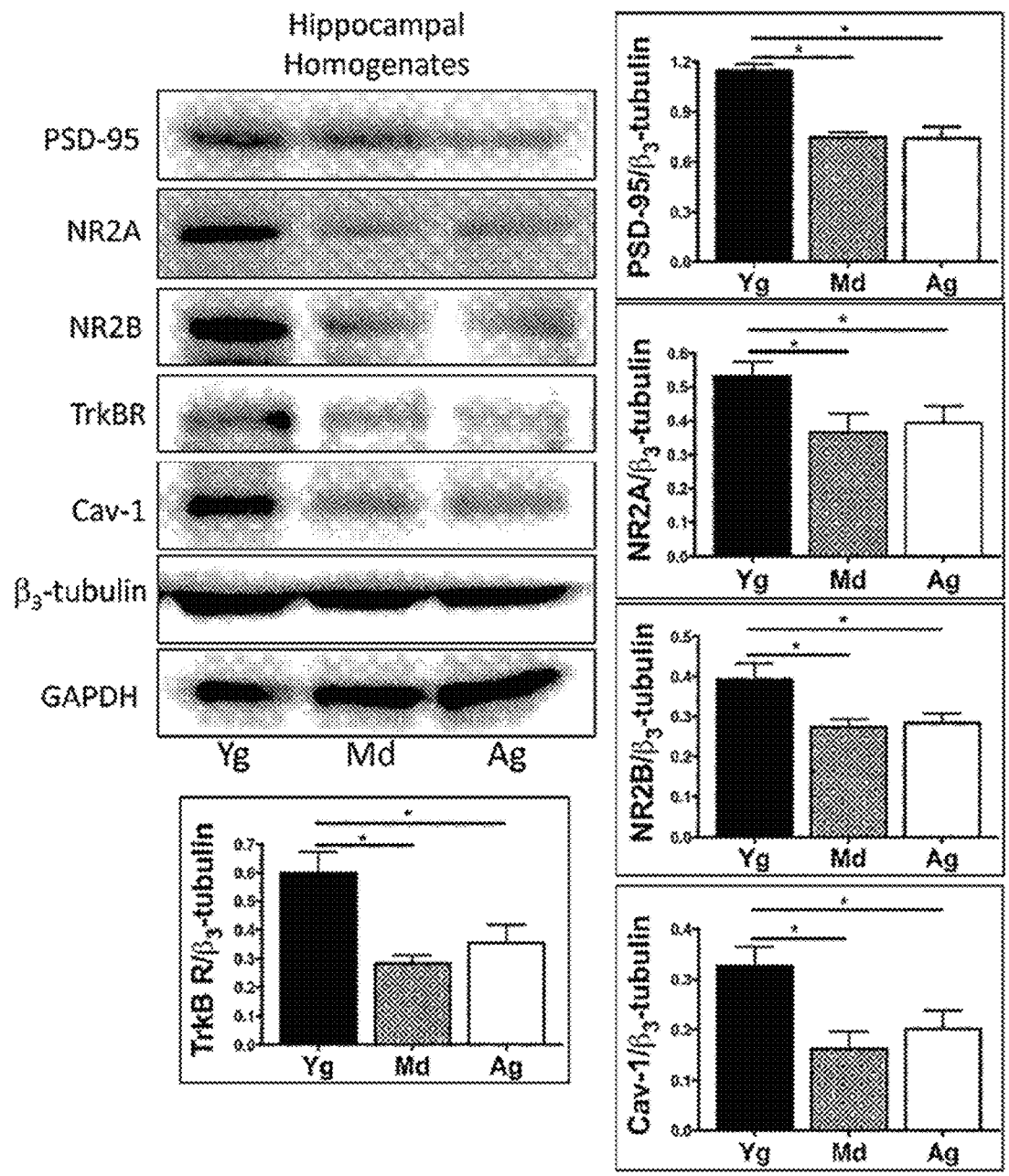
FIG. 1 shows Hippocampal homogenates show an aged dependent reduction in NR2A, NR2B, PSD-95, and Cav-1. Hippocampi were isolated from the brains of C57BL/6J mice at 3-6 months (young, Yg), 12 months (middle aged, Md), and 24 months (aged, Ag). Immunoblot and densitometric analysis demonstrated a significant reduction in PSD-95, NR2A, NR2B, TrkBR, and Cav-1 in the Md and Ag hippocampus compared to Yg. Immunoblots are representative of tissue isolated from 6-7 mice per age group. (*$p<0.05$).

| Nucleotide Position: | Description |
| --- | --- |
| 1-1199 | Human Synapsin I (Syn1) promoter-mouse caveolin-1 (Cav1) protein coding sequence cassette |
| 1-26 | Multiple cloning sequence 1-6 MluI/AflIII restriction enzyme recognition sequence |
| 1-6 | MluI/AflIII restriction enzyme recognition sequence |
| 7-12 | ClaI/BspDI/BanIII/Bsa29I/BseCI/BshVI/BsiXI/Bsp106I/BspXI/Bsu15I/BsuT-UI/ZhoI restriction enzyme recognition sequence |
| 13-18 | KasI/NarI/SfoI/BbeI/DinI/EgeI/EheI/Mly113I restriction enzyme recognition sequence |
| 18-23 | PvuII restriction enzyme recognition sequence |
| 21-26 | PstI/BspMAI restriction enzyme recognition sequence |
| 21-489 | *Homo sapiens synapsin* I (Syn1) promoter sequence corresponding to nucleotide position 1889-2357 of GenBank Accession No. M55301 |
| 229-241 | Conserved sequence element, CSTTYGCCYCYGC (SEQ ID NO: 13), shared with other neuron specifically transcribed genes or promoters, including those for human and rat synapsin I, neurofilament, and nerve growth factor receptor, where S = C or G and Y = C or T; reference for conserved sequence element - Sauerwald A, Hoesche C, Oschwald R, Kilimann MW (1990) The 5'-flanking region of the synapsin I gene. A G + C-rich, TATA- and CAAT-less, phylogenetically conserved sequence with cell type-specific promoter function. J Biol Chem 265: 14932-14937 |
| 279-287 | Conserved sequence element, CGSTGACGTCNC (SEQ ID NO: 14), shared with other neuron specifically transcribed genes or promoters, including those for human and rat synapsin I, neurofilament, and nerve growth factor receptor, where S = C or G and N = A, G, C or T; reference for conserved sequence element - Sauerwald A, Hoesche C, Oschwald R, Kilimann MW (1990) The 5'-flanking region of the synapsin I gene. A G + C-rich, TATA- and CAAT-less, phylogenetically conserved sequence with cell type-specific promoter function. J Biol Chem 265: 14932-14937 |
| 284-291 | cAMP-responsive element, TGACGTCA; reference - Sauerwald A, Hoesche C, Oschwald R, Kilimann MW (1990) The 5'-flanking region of the synapsin I gene. A G + C-rich, TATA- and CAAT-less, phylogenetically conserved sequence with cell type-specific promoter function. J Biol Chem 265: 14932-14937 442 Start site of transcription from synapsin I promoter; reference - Sauerwald A, Hoesche C, Oschwald R, Kilimann M W (1990) The 5'-flanking region of the synapsin I gene. A G + C-rich, TATA- and CAAT-less, phylogenetically conserved sequence with cell type-specific promoter function. J Biol Chem 265: 14932-14937 |
| 442 | Start site of transcription from synapsin I promoter; reference - Sauerwald A. Hoesche C, Oschwald R, Kilimann MW (1990) The 5'-flanking region of the synapsin I gene, A G + C-rich, TATA- and CAAT-less, phylogeneitically conserved sequence with cell type-specific promoter function. J. Biol. Chem. 265: 14932-14937 |

-continued

| Nucleotide Position: | Description |
|---|---|
| 489-508 | Multiple cloning sequence 489-494 SalI restriction enzyme recognition sequence |
| 489-494 | SalI restriction enzyme recognition sequence |
| 495-500 | Acc65I/KpnI/Asp718I restriction enzyme recognition sequence |
| 503-508 | ApaI/PspOMI/Bsp120I restriction enzyme recognition sequence |
| 506-512 | Sequence, CCCAAAC, obtained after replacing SmaI-NotI EGFP-containing fragment of pSyn-EGFP DNA with 685 bp PmeI-NotI Cav1-coding sequence fragment to obtain pSyn-Cav1 DNA; sequence is from joining SmaI end (CCC) to PmeI end (AAAC) |
| 509-530 | Homology to nucleotide position 7437-7417 of GenBank Accession No. AB617819 |
| 525-1179 | *Mus musculus* caveolin 1 (Cav1) sequences corresponding to nucleotide position 73-727 of NCBI Reference Sequence Accession No. NM_007616 |
| 568-1104 | Sequences coding for caveolin 1 protein, corresponding to nucleotide position 116-652 of NCBI Reference Sequence Accession No. NM_007616 or nucleotide position 24-560 of GenBank Accession No. BC038280 |
| 568-570 | Translational initiation codon, ATG, within caveolin 1 coding sequence |
| 1102-1104 | Translational termination codon, TGA, within caveolin 1 coding sequence |
| 1186-1191 | EcoRI/FunII restriction enzyme recognition sequence |
| 1192-1199 | NotI/CciNI restriction enzyme recognition sequence. |

Figure 9A:
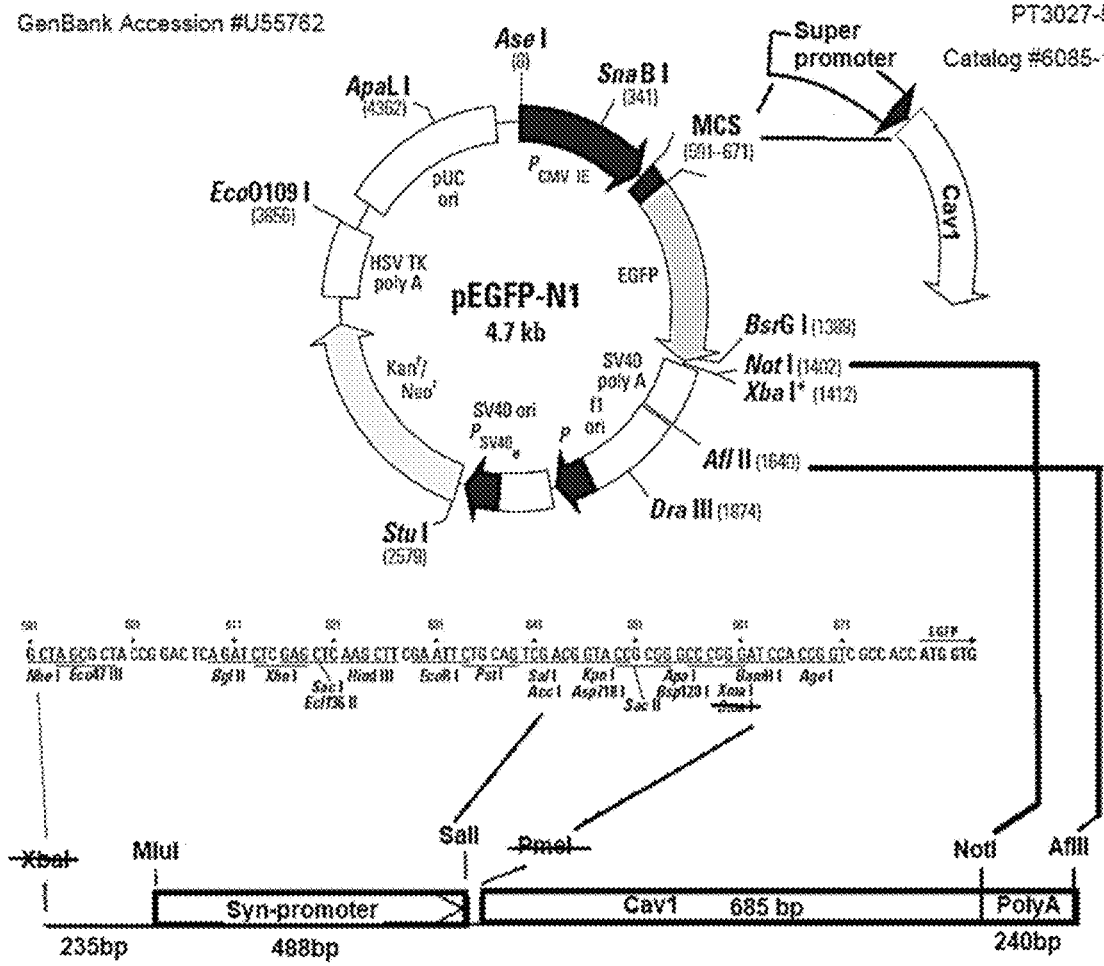
Figure 9B:
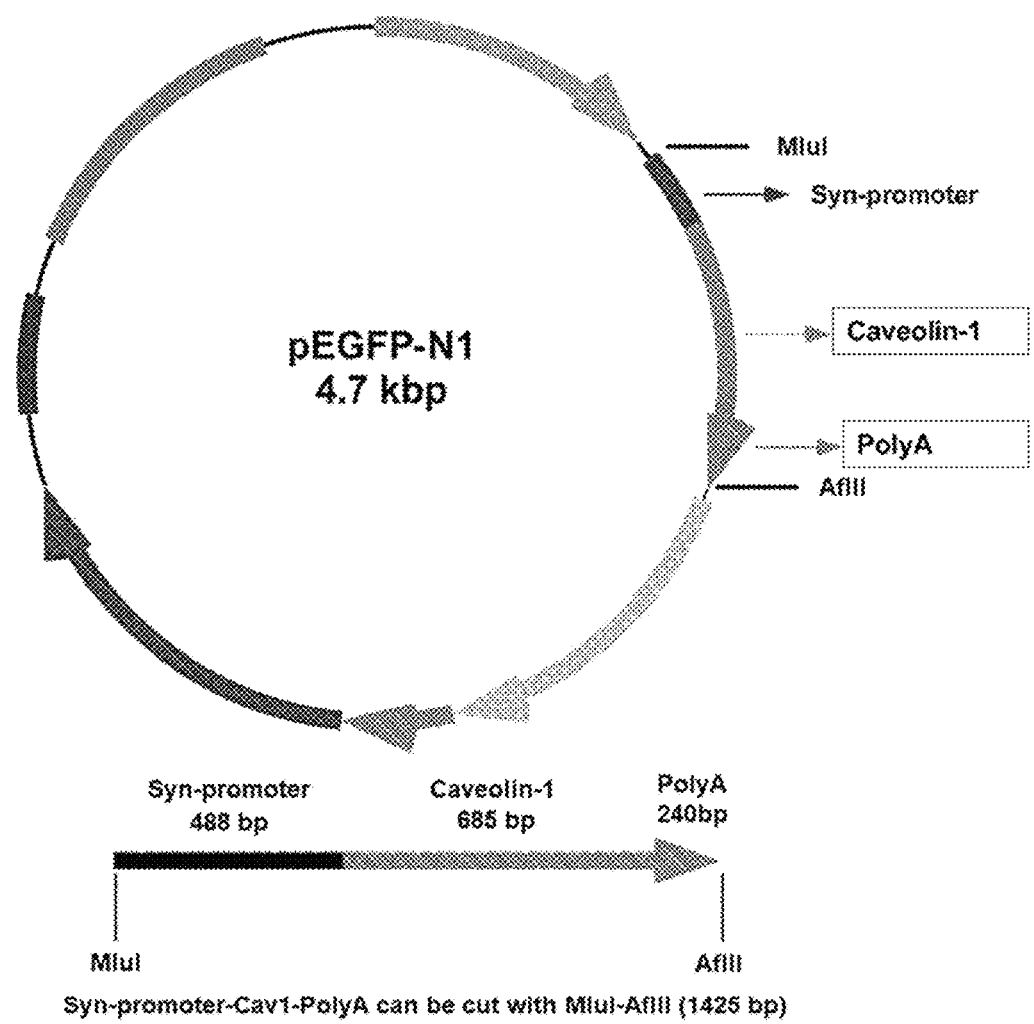
Figure 9C:
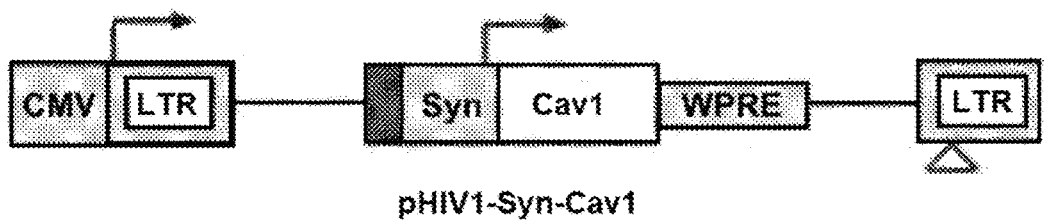

FIG. 9A-C is a schematic of the cloning scheme used to produce the Syn-promoter-Cav1-PolyA DNA cassette unit, using pEGFP-N1 DNA (A), and the resultant pSyn-Cav1 plasmid DNA from which Syn-promoter-Cav1 with or without polyA DNA cassette unit can be obtained following appropriate restriction enzyme digestions (B). A XbaI-SalI DNA fragment, approximately 720 bp, containing the human synapsin I promoter (nucleotide position 1889-2357 of GenBank Accession No. M55301) was inserted into the NheI-SalI sites of pEGFP-N1 (Clontech Catalog #6085-1; GenBank Accession No. U55762) as shown in top of (A). The resulting plasmid called pSyn-EGFP was digested with SmaI and NotI, and the released EGFP coding DNA fragment replaced with a 685 bp PmeI-NotI DNA fragment containing the mouse caveolin 1 coding and flanking sequence (nucleotide position 73-727 of NCBI Reference Sequence Accession No. NM_007616) to produce pSyn-Cav1 plasmid DNA as shown in top of (B). The pSyn-Cav1 plasmid DNA can be used to isolate Syn-promoter-Cav1-PolyA DNA cassette unit by digesting with MluI and AflII releasing approximately 1425 bp fragment with the Syn promoter, full length Cav1 coding sequence, and SV40 polyadenylation signal as shown in bottom of (B); or alternatively if additional flanking sequences are desired with NheI and DraIII to release approximately 1900 bp fragment as stated in bottom of (A). These fragments can be transferred into DNA vectors, such as adenoviral or lentiviral vectors, appropriately digested with restriction enzymes to insert the cassette unit for the delivery of Syn-Cav1 chimeric gene into desired host cells with restricted expression of additional Cav1 protein in neuronal or stem cells. In addition to the Syn-promoter-Cav1-PolyA DNA cassette unit, a smaller cassette unit containing only the Syn-promoter-Cav1 cassette unit without the downstream SV40 polyadenylation signals can be obtained by digesting with MluI and NotI, see notations in FIG. 8. In this case, it is recommended that the recipient vector should supply a polyadenylation signal. An example of a lentiviral vector used to produce retrovirus for delivery of the Syn promoter-Cav1 sequences into neuronal cells is pHIV1-Syn-Cav1 DNA, which was obtained by inserting a Syn promoter-Cav1 cassette unit into the unique BamHI site of the HIV1 vector backbone plasmid pHIV7 (Yam, P. Y., Li, S., Wu, J., Hu, J., Zaia, J. A. and Yee, J. K. (2002) Molecular Therapy 5, 479-484) as shown in (C). A represents a 400-bp deletion in the 3'-LTR that completely removes the HIV enhancer and promoter sequences. Arrows depict the direction of transcription. The 5'-LTR of this HIV-based SIN vector construct contains a fusion promoter with the CMV enhancer linked to the promoter of the HIV LTR. The Syn promoter is used to drive the transcription of downstream caveolin-1 coding region. The solid boxes represent the 190 bp flap sequence from HIV-1, which consists of a polypurine tract sequence (cPPT) and a central termination sequence (CTS) from the HIV polymerase (pol) gene and functions to facilitate nuclear import of the viral preintegration complex (Follenzi, A., Allies, L. E., Bakovic, S., Geuna, M. and Naldini, L. (2000) Nature Genetic, 25, 217-222; Zennou, V., Petit, C., Guetard, D., Nerhbass, U., Montagnier, L. and Charneau, P. (2000) Cell 101, 173-185). Presence of the WPRE or woodcheck hepatitis virus post-transcriptional regulatory element increases transgene expression in the context of plasmid DNAs or viral vectors (Zufferey, R., Donello, J. E., Trono, D. and Hope, T. J. (1999) J Virology 73, 2886-2892; Loeb, J. E., Cordier, W. S., Harris, M. E., Weitzman, M. D. and Hope, T. J. (1999) Human Gene Therapy 10, 2295-2305; Huang, J. and Liang, T. J. (1993) Molec Cell Biol 13, 7476-7486).

The Syn-promoter-Cav1-PolyA DNA cassette unit may be used to directly transfect recipient cells along with a marker gene to select or identify the successfully transfected cells, or alternatively, to obtain stable cell lines.

For the line drawing at the bottom of (A), the numbers in basepair or basepairs (bp) indicated refer to the fragment sizes following digestion with the indicated restriction enzymes on either side of the indicated bp value. The restriction enzyme cleavage sites, XbaI and PmeI, with a strikethrough refer to the fact that these restriction enzyme cleavage sites used to generate a DNA fragment end were lost following fusion of XbaI cohesive end with NheI cohesive end or PmeI blunt end with SmaI blunt end.

FIG. 10A-C shows a schematic depicting the organization of ionotropic glutamate and neurotrophin receptors by Cav-1 in synaptic regions in neurons. (A) Normal neurons show Cav-1 oligomers organizing N-methyl-D-aspartate receptors (NMDAR), tropomyosin kinase receptors (TrkR), and Src tyrosine kinases in synaptic regions. (B) Following lethal ischemia, there is a drastic reduction in Cav-1, synapses, and functional receptors. (C) Re-expression of Cav-1 driven by a neuronal specific synapsin promoter (Syn-Cav-1) enhances expression of glutamate and neurotrophin receptors and improves neuroprotective signaling in the central nervous system.

FIG. 11A-F shows Neuron-targeted expression of Cav-1 enhances expression of pro-survival signaling components in wild-type primary neurons. (A) Cav-1 KO glia were incubated with SynCav1 or a non-tissue specific adenoviral vector containing the Cav-1 gene (AdvCav1). Cav-1 KO glia show re-expression of Cav-1 with the non-specific AdvCav1 but not SynCav1, indicating SynCav1 neuronal specificity. (B) Primary neurons were transfected with Syn-GFP or SynCav1 ($2 \times 10^9$ viral particles) for 72 h and then subjected to immunoblot analysis. SynCav1 enhanced protein expression of PSD-95, NR2A, NR2B, TrkBR, and CT-B (cholera toxin B, lipid raft marker) (n=6, #p<0.05). (C) NMDA (10 μM; 10 min) treatment enhanced P-ERK1/2, P-CaMKII, and P-Src (n=4-9, p<0.05) in SynCav1-expressing neurons. (D) BDNF (50 ng/ml; 10 min) treatment enhanced P-TrkB, P-Akt, and P-ERK1/2 (n=4, p<0.05) in SynCav1-expressing neurons. (E) Forskolin (Fsk, 10 μM; 10 min) treatment enhanced P-ERK1/2 (n=4, p<0.05) in SynCav1-expressing neurons. (F) Neurons were transfected with SynGFP, SynCav1, or AdvshRNACav1 for 72 h followed by treatment with a dopamine 1 receptor agonist (10 μM), NMDA, serotonin receptor 6 agonist (10 μM, 5-HT6), or Fsk (10 μM) and cAMP was measured by radioimmunoassay (28,29). Neurons were pre-treated with the PDE4 inhibitor, rolipram (10 μM). Stimulation of D1R, NMDAR, 5-HT7, and adenylyl cyclase (AC) significantly increased cAMP formation in the SynCav1-transfected neurons (n=4; p<0.05). Conversely, agonist-stimulated cAMP formation is blunted in shRNACav1-transfected neurons.

Figure 12A:
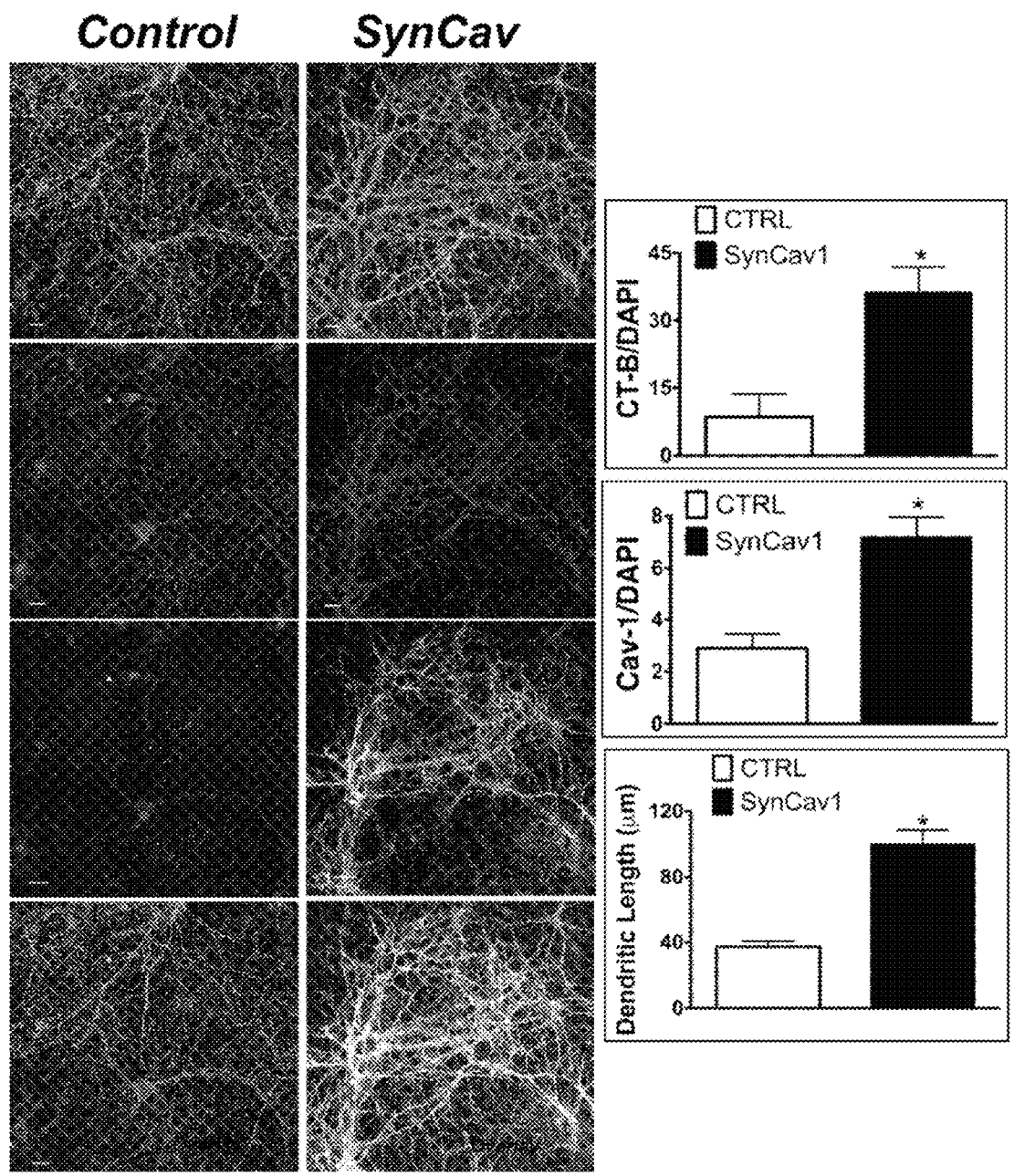
Figure 12B:
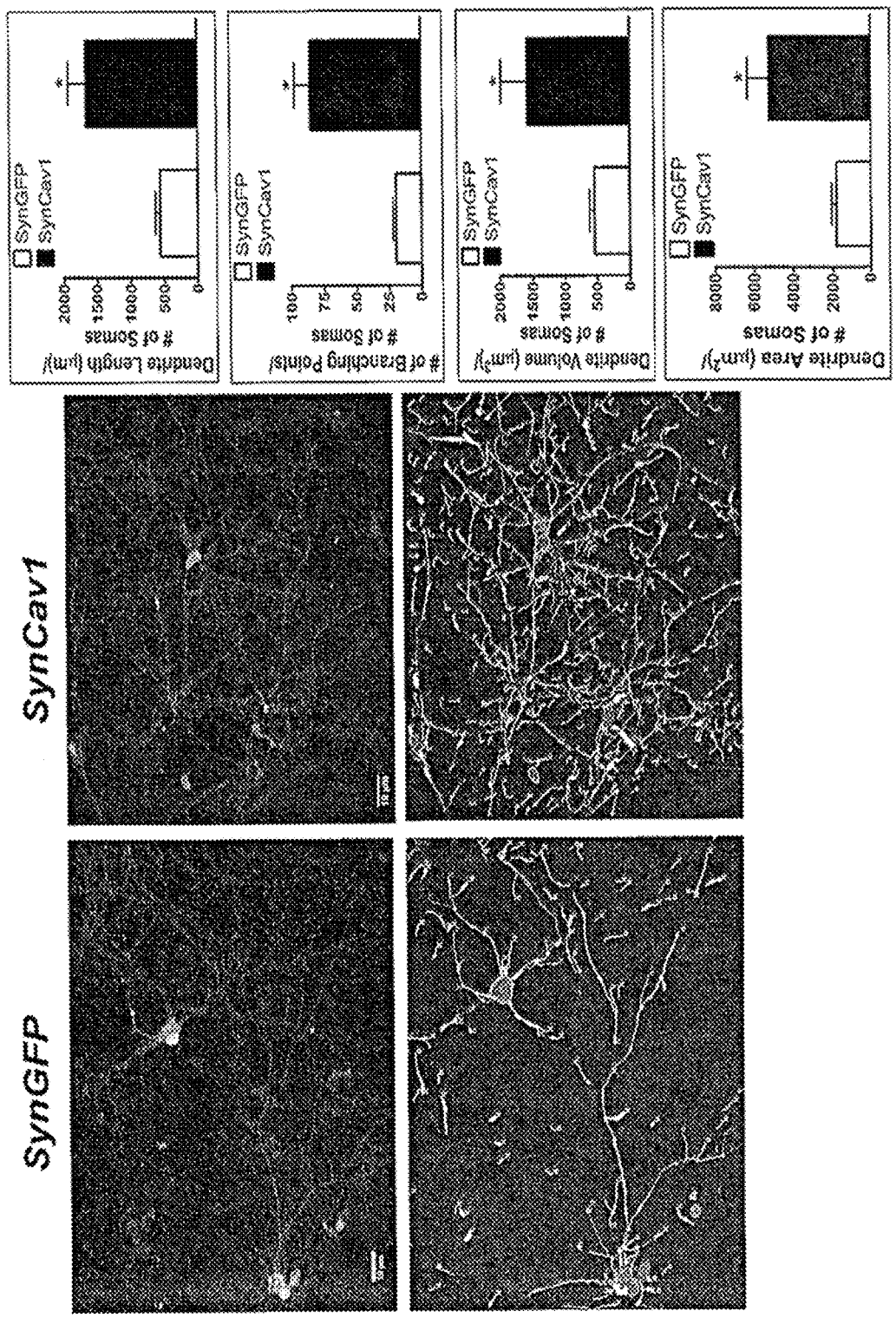

FIG. 12A-B shows Neuron-targeted expression of Cav-1 enhances membrane/lipid rafts, dendrite number and length. (A) Primary neurons (days in vitro, DIV4) were transfected with SynCav1 (109 viral particles/μl) and cells were grown for 21 days and then stained with CT-B (488) (green, top panels), the dendritic shaft marker β3-tubulin (red, middle panels), and for Cav-1 (white, bottom panels). (B) Primary neurons were incubated with SynCav1 or SynGFP for 21 days; dendritic branching, length, and area were then measured using Autoneuron, a tracing algorithm that measures 3D image volume stacks. Top panels, Neurons stained for the neuronal F-actin binding protein drebrin (red); bottom panels, Autoneuron tracing of the drebrin stain. Scale bar, 10 μm.

Figure 13A:
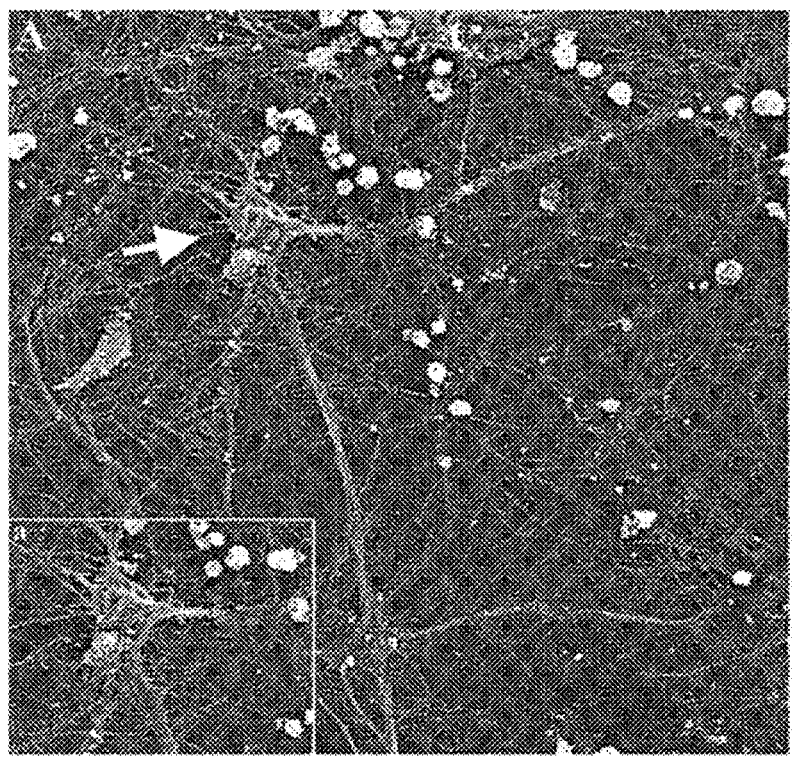
Figure 13B:
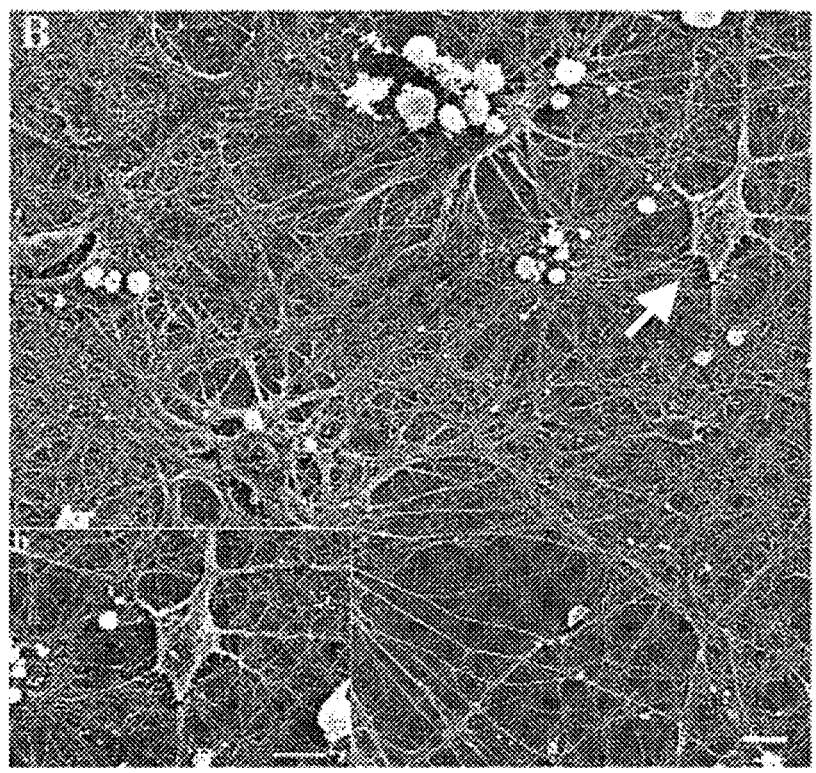

FIG. 13A-B shows Neuron-targeted expression of Cav-1 enhances dendritic growth. Primary neurons were incubated with SynCav1 or SynGFP for 21 days and imaged by scanning electron microscopy. (A) SynGFP neurons; (B) SynCav1-incubated neurons; Scale bar, 10 um. Images were acquired on a Hitachi S-270 SEM with Gatan digital camera.

Figure 14A:
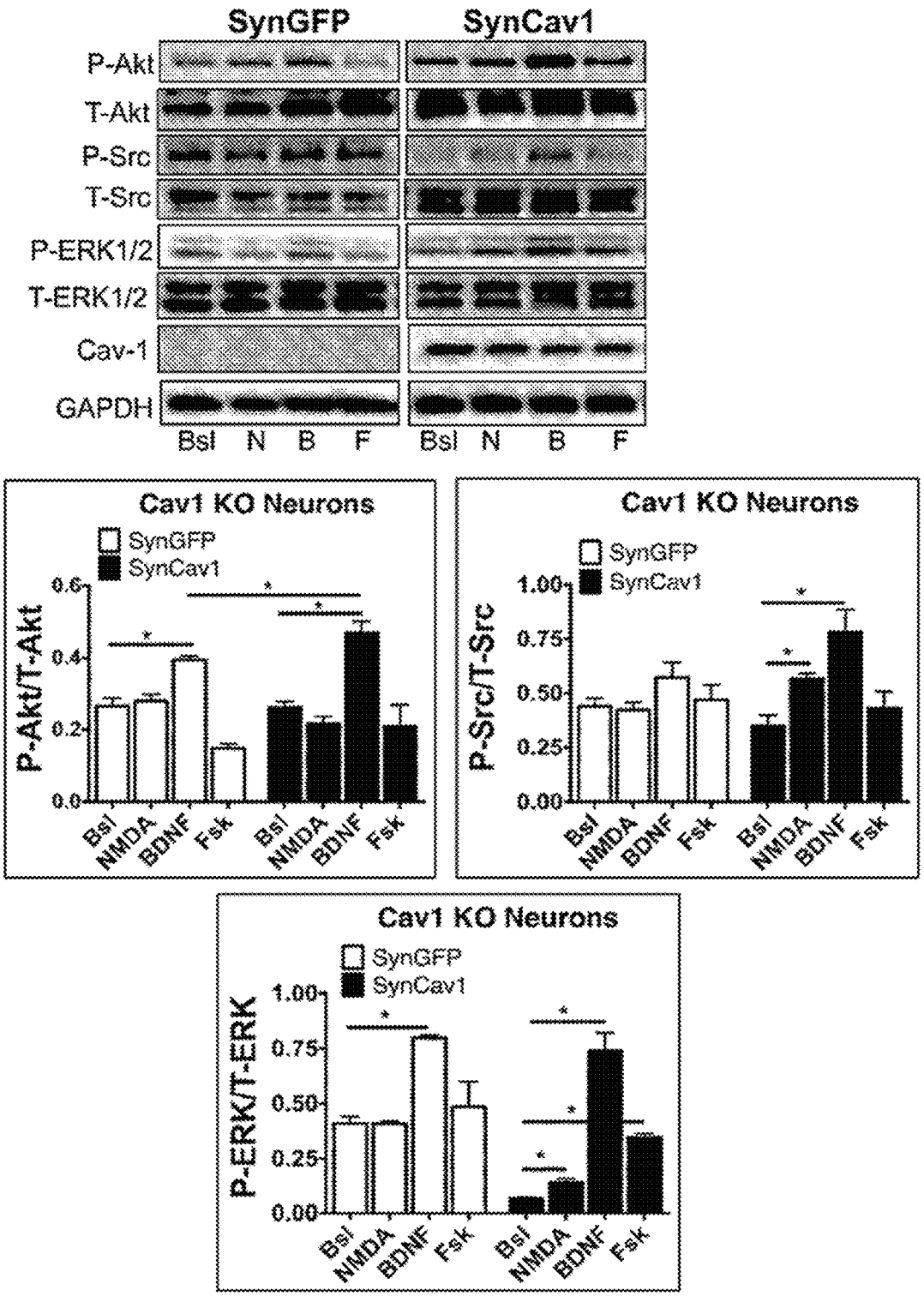
Figure 14B:
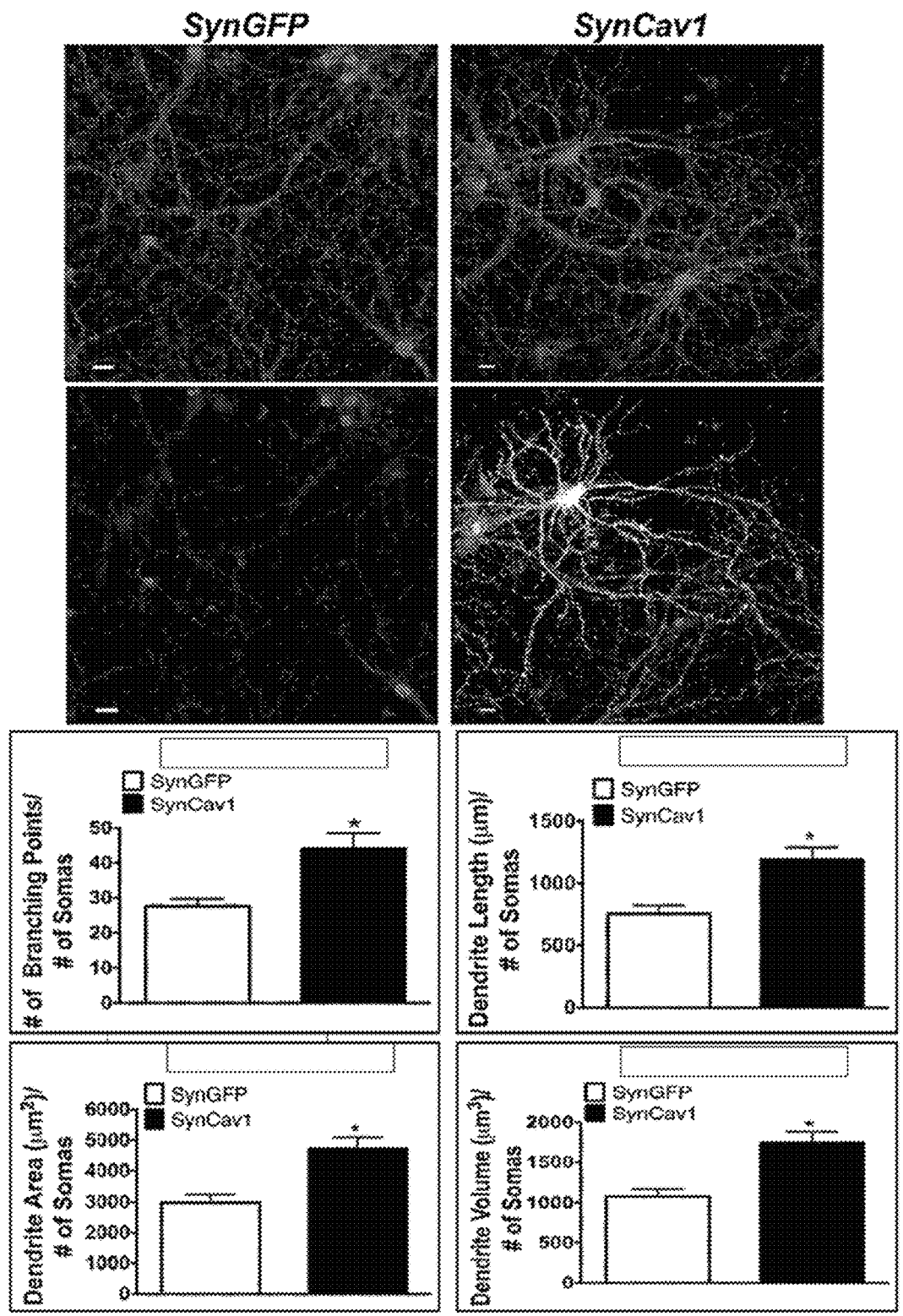

FIG. 14A-B shows Neuron-targeted expression of Cav-1 in Cav-1 KO neurons restores pro-survival signaling and enhances growth of dendrites. (A) Primary neurons from Cav-1 KO mice were incubated with SynGFP or SynCav1 ($2 \times 109$ viral particles) for 72 h and the treated with various agonists. SynCav1 significantly enhanced NMDA (10 μM; 10 min)-mediated P-ERK1/2 (n=4 *p<0.05) expression, BDNF (50 ng/ml; 10 min)-promoted expression of P-Akt, P-Src, and P-ERK1/2 (n=4, *p<0.05) and Fsk (10 μM; 10 min)-promoted expression of P-ERK1/2 (n=4, *p<0.05). Bsl=basal, N=NMDA, B=BDNF, F=forskolin. (B) SynCav1 expression in Cav-1 KO neurons significantly enhanced dendritic branching, length, and area (*p<0.05) (n=5, mean±SEM) 21 d post-treatment. Neurons were stained for the dendritic marker MAP2 (red), Cav-1 (white), and DAPI (blue). Scale bar, 10 μm.

Figure 15A:
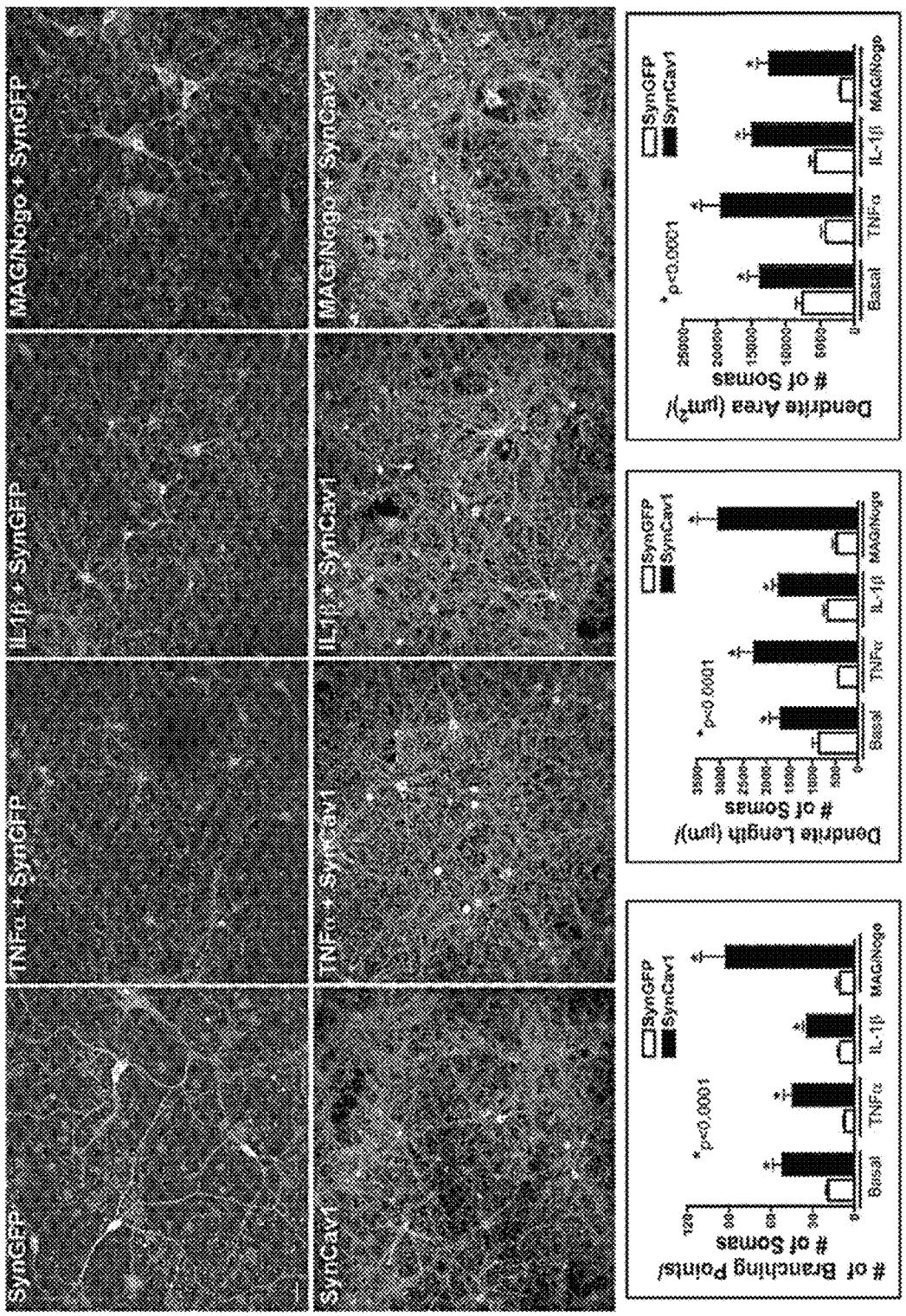
Figure 15B:
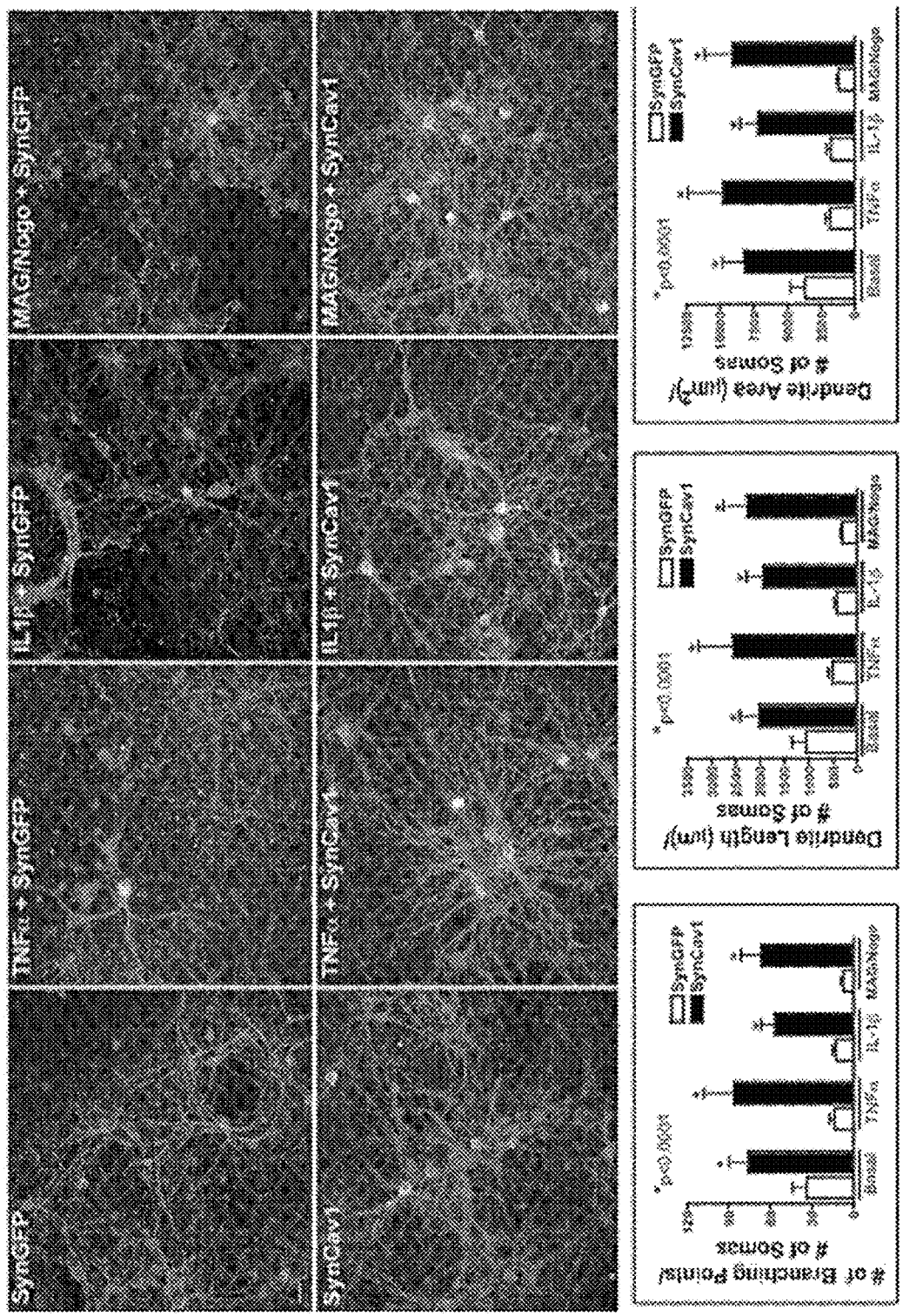

FIG. 15A-B shows Neuron-targeted expression of Cav-1 enhances growth in primary neurons in the presence of inhibitory cytokines and myelin associated glycoproteins. Primary neurons from wild-type (A) or Cav-1 KO (B) mice were incubated with TNFα (1 ng/ml), IL-1β (1 ng/ml), or MAG+Nogo (1 mg/ml) prior to incubation with SynGFP or SynCav1 for 21 days. Neurons were stained for β3-tubulin (red pixels) and Cav-1 (white pixels) followed by measurement of brandling, length, and area of dendrites using Autoneuron. SynCav1 significantly enhanced dendritic arborization in neurons from both WT and Cav-1 KO mice in neurons pre-treated with TNFα, IL-1β, and MAG/Nogo compared to neurons from SynGFP mice (One-way ANOVA Bonferroni's Multiple Comparison Test, *p<0.0001, n=4-7). Images were captured with an Olympus confocal microscope (Fluoroview 1000). Optical sections spaced by 0.2-0.5 μm were obtained. Scale bar, 10 um.

Figure 16A:
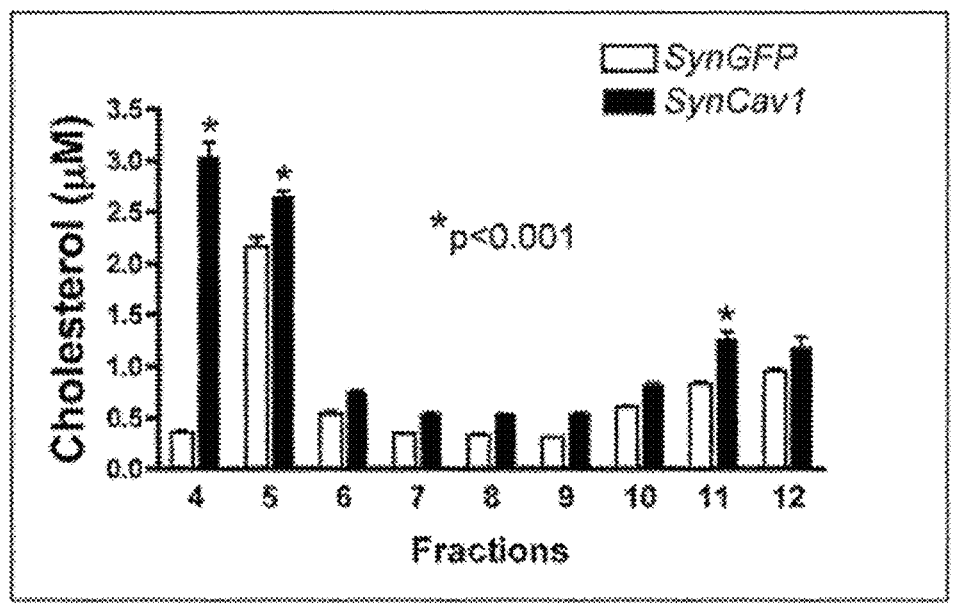
Figure 16B:
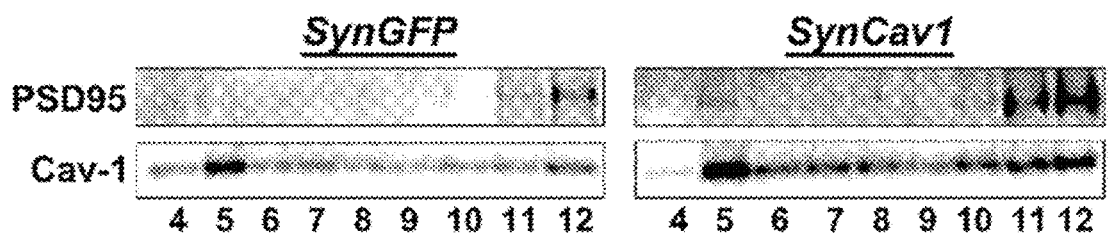
Figure 16C:
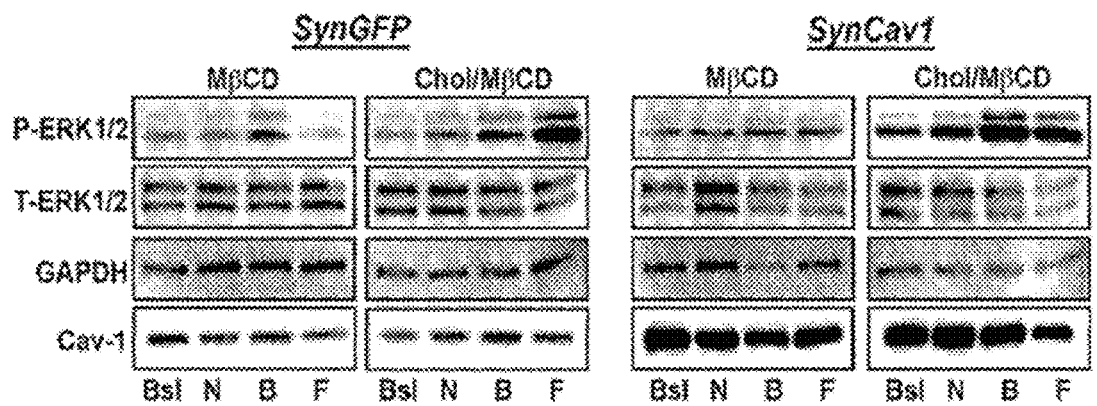

FIG. 16A-C shows Neuron-targeted expression of Cav-1 in wild-type primary neurons enhances membrane cholesterol. (A) Primary neurons were incubated with SynGFP or SynCav1 (2×109 viral particles) for 72 h and membrane/lipid rafts were purified by sucrose density fractionation. SynCav1 significantly increased cholesterol in buoyant fractions 4 & 5 (One-way ANOVA Bonferroni's Multiple Comparison Test, *p<0.001, n=3). (B) Immunoblot analysis detected an increase in PSD-95 and Cav-1 in the buoyant fractions. (C) SynCav1 neurons pre-treated with MβCD (3 mM, 30 min) exhibited a loss in NMDA (10 μM; 10 min), BDNF (50 ng/ml; 10 min), and Fsk (10 uM; 10 min)-mediated P-ERK1/2 compared to cholesterol:MβCD treated SynCav1 neurons, Bsl=basal, N=NMDA, B=BDNF, F=forskolin.

DETAILED DESCRIPTION OF THE INVENTION

Definitions

All scientific and technical terms used in this application have meanings commonly used in the art unless otherwise specified. As used in this application, the following words or phrases have the meanings specified.

As used herein, "administer" or "administering" to a subject includes but is not limited to tumoral administration, intratumoral administration, peritumoral administration, intravenous (i.v.) administration, intraperitoneal (i.p.) administration, intramuscular (i.m.) administration, subcutaneous administration, oral administration, inhalation administration, topical administration, administration by injection, or the implantation of a slow-release device such as a miniosmotic pump, or administration by slow release devices such as vesicles or capsules to the subject.

The phrase "treating" or "treatment" refers to any manner in which one or more of the symptoms of a disease or disorder are ameliorated or otherwise beneficially altered, whether in a permanent or temporary manner, which can be attributed to or associated with administration of the compound or composition herein. The term encompasses any pharmaceutical use, including prophylactic uses in which the development of one or more of the symptoms of a disease or disorder is prevented, delayed or reduced, whether in a permanent or temporary manner, which can be attributed to or associated with administration of the composition. In an embodiment of the invention, treatment encompasses the use of Caveolin-1 for treating a neurological (e.g., neurodegenerative) disease or disorder.

As used herein, "subject" means any living organism to which the agents can be administered in order to treat the neurological disorder. Subjects may include, but are not limited to, humans, monkeys, cows, goats, sheep, mice, rats, cats, rabbits, dogs, hamsters, horses, and any transgenic animals.

As used herein, "pharmaceutically acceptable carrier" means any material that may be combined with an expression system, components of an expression system, biological material derived from an expression system, biological material derived from the use of an expression system, nucleic acid or modified nucleic acid of an expression system, DNA or modified DNA of an expression system, RNA or modified RNA of an expression system of the invention (or derivatives thereof) and composition containing caveolin-1 protein, its variants, or its protein fragment from any species (Tang, Z., Scherer, P. E., Okamoto, T., Song, K., Chu, C., Kohtz, D. S., Nishimoto, I., Lodish, H. F. and Lisanti, M. P. (1996) The Journal of biological chemistry 271, 2255-2261; Williams, T. M. and Lisanti, M. P. (2004) Genome biology 5, 214; Cameron, P. L., Ruffin, J. W., Bollag, R., Rasmussen, H. and Cameron, R. S, (1997) J Neurosci 17, 9520-9535; Scherer, P. E., Okamoto, T., Chun, M., Nishimoto, I., Lodish, H. F. and Lisanti, M P. (1996) Proc Natl Acad Sci USA 93, 131-135; Tang, Z., Okamoto, T., Boontrakulpoontawee, P., Katada, T., Otsuka, A. J. and Lisanti, M. P. (1997) J Biol Chew 272, 2437-2445; Cohen, A. W., Hnasko, R., Schubert, W. and Lisanti, M. P. (2004) Physiol Reviews 84, 1341-1379; Kirkham, M., Nixon, S. J., Howes, M. T., Abi-Rached, L., Wakeham, D. E., Hanzal-Bayer, M., Ferguson, C., Hill, M. M., Femandez-Rojo, M., Brown, D. A. et al. (2008) J Cell Sci 121, 2075-2086; Razani, B., Woodman, S. E. and Lisanti, M. P. (2002) Pharm Reviews 54, 431-467), be it purified from the original species or produced via recombinant DNA methods, in order to administer them to a subject in any form so as to prevent or treat a neurodegenerative disease or neurological disorder. For example, a carrier includes any material that will maintain the agents' effective activity when administered to a subject and that is non-reactive with a subject's immune system. Potential carriers may include, but are not limited to, any solvents, media, suspensions, emulsions or other excipients such as starch, milk, sugar, certain types of clay, gelatin, stearic acids, stearate salts, talcum, oils, gums, glycols, flavorings, preservatives or color additives, etc. Potential carrier forms may include sterile solutions, aerosols, liposomes, amphoteric liposomes, lipid-based transfection agents, peptide-based transfection agents, positively charged polymers, negatively charged polymers, dendrimer transfection agents, poly(amidoamine) (PAMAM)-based dendrimer, positively charged, activated dendrimers (such as SuperFect or PolyFect; Qiagen) poly anions, poly actions, spermidine, spermine, divalent metals, calcium ion and calcium salts, calcium chloride, calcium phosphate, vesicles, biolballistic or biolistic particles, gold nano- or micro-particles, spermidine-coated nano- or micro-particles, positively charge-coated nano- or micro-particles, 1.0-micron to 1.5-micron diameter gold particles used in conjunction with Helios gene gun (BioRad) pills, tablets or capsules.

As used herein, "neuronal cell" is any electrically excitable cell constituting the developing nervous system or developed nervous system, which typically does not undergo cell division. "Neural stem cell" is any multipotent and self-renewing cell, which gives rise to a more lineage restricted progenitor cell that differentiates either into a neuron or a glial cell.

A "neuron-specific regulatory element" can be a nucleic acid with a binding site for a protein factor which specifically is characteristically present in a neuronal cell and specifically binds to the sequence in the binding site, or alternatively, a group of binding sites such as those constituting a transcriptional regulatory unit, a promoter, a transcriptional enhancer, or promoter-enhancer pair to which a set of factors (several factors) bind, the combination of these factors confer specificity for a neuronal cell. The "neuron-specific regulatory element" may be derived from nature or alternatively maybe conceived and made by the hands of man such as to confer selective or specific expression of caveolin-1 coding sequences or its derivative in neuronal cells or neural stem cells. The "neuron-specific regulatory element" may respond to a signal controlling its activity. One such example of a man made "neuron-specific regulatory element" dependent on a signal for its function is the incorporation of tetracycline operator sites (tetO) and a doxycycline-regulated transcriptional activator and/or repressor to control the transcriptional activity of multiple tetO-containing responder gene, as is well known in the art (Blesch, A., Conner, J. M. and Tuszynsld, M. H. (2001) Gene Therapy 8, 954-960; Gascon, S., Paez-Gomez, J. A., Diaz-Guerra, M., Scheiffele, P. and Scholl, F. G. (2008) J Neurosci Methods 168, 104-112; Kafri, T., van Praag, H., Gage, F. H. and Verma, I. M. (2000) Molecular Therapy 1, 516-521; Koponen, J. K., Kankkonen, H., Kannasto, J., Wirth, T., Hillen, W., Bujard, H. and Yla-Herttuala, S. (2003) Gene Therapy 10, 459-466; Zhou, X., Vink, M., Klaver, B., Berkhout, B. and Das, A. T. (2006) Gene Therapy 13, 1382-1390; Gao, Q., Sun, M., Wang, X., Zhang, G. R, and Geller, A. I. (2006) Brain Res 1083, 1-13).

"Specific" as used within the context of "neuron-specific," "neuronal cell-specific," or "neural stem cell-specific" should be construed in the broadest term to reflect a factor that may not only be restricted to particular cells but also a factor that may be most abundant or most active in the particular cells.

As used herein, a "vector" is a nucleic acid into which a neuron-specific regulatory element and caveolin-1 coding sequence can be inserted, following which the "vector" permits transcription and proper processing of the nascent transcript to allow expression of the caveolin-1 protein. The "vector" may also be a nucleic acid which following introduction into a cell and in the presence of viral proteins produces virions or viral particles with the nucleic acid sequence of the neuron-specific regulatory element and caveolin-1 coding sequence incorporated in the genome of the virion or viral particle.

While by no means meant to be exhaustive, examples of viral vectors and non-viral vectors along with their use and mode of delivery can be found in the following references: Gossen, M. and Bujard, H. (1992) Proc Natl Acad Sci USA 89, 5547-5551; Gossen, M., Freundlieb, S., Bender, G., Muller, G., Hillen, W. and Bujard, H. (1995) Science, 268, 1766-1769; Akagi, K., Kanai, M., Saya, H., Kozu, T. and Berns, A. (2001) Nucleic Acids Res 29, E23; Einav, Y., Shistik, E., Shenfeld, M., Simons, A. H., Melton, D. W. and Canaani, D. (2003) Molec Cancer Therapeutics, 2, 1121-1128; Lufino, M. M., Edser, P. A. and Wade-Martins, R. (2008) Molec Therapy 16, 1525-1538; Durand, S. and Cimarelli, A. (2011) Viruses 3, 132-159; Glover, D. J. (2011) Infectious Disorders Drug Targets. [PMID: 22034936]; High, K. A. and Aubourg, P. (2011) Methods Mol Biol 807, 429-457; Wang, L., Blouin, V., Brument, N., Bello-Roufai, M. and Francois, A. (2011) Methods Mol Biol 807, 361-404; Tohnachov, O. E. (2011) Current Gene Therapy 11; Lentz, T. B., Gray, S. J. and Samulski, R. J. (2011) Neurobiol Disease [PMID: 22001604]; Vetrini, F. and Ng, P. (2010) Viruses 2, 1886-1917; Ehrengruber, M. U., Schlesinger, S. and Lundstrom, K. (2011) Curr Protocols Nneurosci/editorial board, Jacqueline N. Crawley . . . [et al.], Chapter 4, Unit4 22; Morgenstern, P. F., Marongiu, R., Musatov, S. A. and Kaplitt, M. G. (2011) Methods Mol Biol 793, 443-455; Guo, X. and Huang, L. (2011) Accounts of chemical research [PMID: 21870813]; Lufino, M. M., Popplestone, A. R., Cowley, S. A., Edser, P. A., James, W. S. and Wade-Martins, R. (2011) Methods Mol Biol 767, 369-387; Kato, S., Kuramochi, M., Takasumi, K., Kobayashi, K., Inoue, K. I., Takahara, D., Hitoshi, S., Ikenaka, K., Shimada, T. and Takada, M. (2011) Human Gene Therapy [PMID: 21806473]; Zhao, L., Wu, J., Zhou, H., Yuan, A., Zhang, X., Xu, F. and Hu, Y. (2011) Current gene therapy [PMID: 21711227].

In order that the invention herein described may be more fully understood the following description is set forth.

Compositions of the Invention

The invention provides expression systems for producing Caveolin-1 primarily in neuronal cells or neural stem cells comprising at least one neuron-specific regulatory element and a nucleic acid sequence encoding Caveolin-1.

In one embodiment, the neuron-specific regulatory element is a binding site for a sequence-specific DNA-binding protein, primarily expressed in neuronal cells or neural stem cells. In another embodiment, the neuron-specific regulatory element is a group of binding sites for a transcription factor or its interacting protein uniquely or predominantly present in neuronal cells. In a different embodiment, the neuron-specific regulatory element is a group of different binding sites for a group of transcription factors uniquely or predominantly present in neuronal cells.

In one embodiment, the neuron-specific regulatory element (e.g., a neuron-specific transcriptional regulatory element) is a neuron-specific promoter. It may be a synapsin promoter, e.g., as set forth in FIG. 8 beginning at position 21 and ending at position 489 (SEQ ID NO:1). Other suitable promoters include, but are not limited to, a Dopaminergic promoter, enolase promoter, neurofilament promoter, nerve growth factor receptor promoter, and CaMKII promoter.

In one embodiment, the neuron-specific regulatory element (e.g., a neuron-specific transcriptional regulatory element) is a neuron-specific transcriptional enhancer or neuron-specific transcriptional enhancer-promoter combination.

In one embodiment, the neuron-specific regulatory element is based on either multiple lac operator (lacO) sites or multiple tetracycline operator (tetO) sites fused upstream of a minimal or basal promoter. A bacterial transcription factor that can bind to its respective operator site is expressed in a neuronal cell or a neural stem cell, such as lac repressor for the series of lacO sites or tetracycline repressor for a series of tetO sites. Binding of the lac repressor to the lacO sites or tetracycline repressor to the tetO sites, is controlled by the presence or absence of IPTG or doxycycline/tetracycline, respectively, giving an "on-off" switch to control the transcription of the downstream sequences (Cronin, C. A., Gluba, W. and Scrable, H. (2001) Genes Dev 15, 1506-1517; Blesch, A., Conner, J. M. and Tuszynski, M. H. (2001) Gene Therapy 8, 954-960; Gascon, S., Paez-Gomez, J. A., Diaz-Guerra, M., Scheiffele, P. and Scholl, F. G. (2008) J Neurosci Methods 168, 104-112; Kafri, T., van Praag, H., Gage, F. H. and Verma, I. M (2000) Molecular Therapy 1, 516-521; Koponen, J. K., Kankkonen, H., Kannasto, J., Wirth, T., Hillen, W., Bujard, H. and Yla-Herttuala, S. (2003) Gene Therapy 10, 459-466; Zhou, X., Vink, M., Klaver, B., Berkhout, B. and Das, A. T. (2006) Gene Therapy 13, 1382-1390; Gao, Q., Sun, M., Wang, X., Zhang, G. R. and Geller, A. I. (2006) Brain Res 1083, 1-13). In the case of the tetracycline/doxycycline regulated system, the repressor of the tetracycline resistance operon of *Escherichia coli* was initially fused to the transcriptional activation domain of virion protein 16 (VP 16) of herpes simplex virus to produce a tetracycline- (or doxycycline-) controlled transactivator called tTA, which binds tetO sites only in the absence of tetracycline to produce robust transcription (Gossen, M. and Bujard, H. (1992) Proc Natl Acad Sci USA 89, 5547-5551).

In one embodiment, the multiple tetracylcine operator (tetO) sites fused upstream of a minimal or basal promoter is regulated by a neuronal cell-specific or neural stem cell-specific expression of a mutant tTA called reverse transctivator (rtTA) in which the tetracycline repressor chimeric transactivator binds its tetO sequences only in the presence of tetracycline (or doxycycline) to drive the transcription from the minimal promoter (Gossen, M., Freundlieb, S., Bender, G., Muller, G., Hillen, W. and Bujard, H. (1995) Science, 268, 1766-1769). The transcriptional activation domain may be exchanged, e.g., SV40 VP16 activation domain with transcriptional activating domain of human E2F4 transcription factor, with other activation domain to obtain a more suitable transcriptional activation domain (Akagi, K., Kanai, M., Saya, H., Kozu, T. and Berns, A. (2001) Nucleic Acids Res 29, E23).

In one embodiment, the neuron-specific regulatory element (e.g., a neuron-specific transcriptional regulatory element) and caveolin-1 coding sequence reside on a nucleic acid with chromatin insulator sequences, e.g., chicken beta-globin locus insulator (Giles, K. E., Gowher, H., Ghirlando, R., Jin, C. and Felsenfeld, G. (2010) Cold Spring Harbor Symp Quant Biol 75, 79-85; Macarthur, C. C., Xue, H., Van Hoof, D., Lieu, P. T., Dudas, M., Pontes, A., Swistowski, A., Touboul, T., Seerke, R., Laurent, L. C. et al. (2011) Stem Cells Dev (PMID: 21699412)) such that the insulators are on either side of the neuronal cell- or neural stem cell-specific transcription Unit. The function of the insulator DNA sequences is to ensure long term gene expression and prevent silencing of the introduced transgene.

In one embodiment, the neuron-specific regulatory element (e.g., a neuron-specific transcriptional regulatory element) and caveolin-1 coding sequence reside on a vector, which can replicate autonomously in neuronal cell or neural stem cell and be stably inherited as an episome. One such vector uses Epstein-Barr virus cis- and trans-elements to create a stably replicated and maintained episome in mammalian cells (Einav, Y., Shistik, E., Shenfeld, M., Simons, A. H., Melton, D. W. and Canaani, D. (2003) Molec Cancer Therapeutics 2, 1121-1128; Lufino, M. M., Edser, P. A. and Wade-Martins, R. (2008) Molecular Therapy 16, 1525-1538).

The nucleic acid sequence encoding Caveolin-1 may be from any mammal including but not limited to humans, monkeys, cows, goats, sheep, mice, rats, cats, dogs, hamsters, and horses.

In one embodiment, the nucleic acid sequence encoding a murine Caveolin-1 is set forth in FIG. 8 beginning at position 568 and ending at position 1104 (Tang, Z. L., Scherer, P. E. and Lisanti, M. P. (1994) Gene 147, 299-300; GenBank Accession No. U07645).

In another embodiment, the nucleic acid sequence encoding a human Caveolin-1 is set forth in SEQ ID NO:5 beginning at position 1 and ending at position 537 (Glenney, J. R., Jr. (1992) FEBS letters, 314, 45-48; Cohen, A W., Hnasko, R., Schubert, W. and Lisanti, M. P. (2004) Physiol Reviews 84, 1341-1379; GenBank Accession No. AB45128 and Z189514).

In a further embodiment, the nucleic acid sequence encoding a canine Caveolin-1 is shown in SEQ ID NO:7 beginning at position 1 and ending at position 537 (Kurzchalia, T. V., Dupree, P., Parton, R. G., Kellner, R., Virta, H., Lehnert, M. and Simons, K. (1992) J Cell Biol 118, 1003-1014; NCBI Reference Sequence: NM_001003296; GenBank Accession No. Z12161).

In yet a further embodiment, the nucleic acid sequence encoding a bovine Caveolin-1 is shown in SEQ ID NO:9 beginning at position 1 and ending at position 537 (Ju, H., Zou, R., Venema, V J. and Venema, R. C. (1997) J Biol Chem 272, 18522-18525; GenBank Accession No. U86639).

Additionally, in another embodiment, the nucleic acid sequence encoding an equine Caveolin-1 is shown in SEQ ID NO:11 beginning at position 268 and ending at position 804 (NCBI Reference Sequence: NM_001114143).

In one embodiment of the invention, the expression system is a double-stranded DNA molecule with a neuron-specific promoter or promoter-enhancer upstream of a caveolin-1 coding sequence, so as to permit specific or selective transcription of the caveolin-1 coding sequences in neuronal cell or neural stem cell. To ensure proper processing and maturation of the nascent caveolin-1 transcript, the expression system will have a polyadenylation signal in the 3' untranslated region (3' UTR) of the transcript, such as those from SV40 polyadenylation signals as found in pEGFP-N1 plasmid DNA (Clontech) and preferably include an intron, e.g., a chimeric intron as described in pCI plasmid DNA (Promega), either in the 5' UTR or 3' UTR of the nascent transcript. The context of the translation initiation codon may be altered to better fit Kozak consensus sequence for efficient utilization of the start site of translation ATG, as is known in the art. The transcription unit consisting of a promoter or promoter-enhancer, caveolin-1 coding sequences, polyadenylation signals and preferably an intron maybe flanked by insulator elements to ensure long term and stable expression of the trans gene.

In one embodiment of the invention, the expression system is a vector, e.g., a viral vector, into which a neuron-specific regulatory element and caveolin-1 coding sequences have been inserted. This vector will supply the necessary polyadenylation signals as well as the optional intron and insulator elements.

In one embodiment of the invention, the expression system is a vector, e.g., a viral vector, into which a neuron-specific regulatory element, caveolin-1 coding sequences, and polyadenylation signals have been inserted.

Merely by way of example, the vector may comprise nucleic acids, e.g., deoxyribonucleic acid (DNA). The vector may be used to produce viral particles, either corresponding to RNA viruses or DNA viruses. In one embodiment, the vector or a minimal expression system (consisting of a neuron-specific promoter or promoter-enhancer linked upstream of a caveolin-1 coding sequence which is joined to polyadenylation signals at its 3' end with an optional intron either in the 5'- or 3'-UTR and optional insulator elements at either end of the transcription unit) may be associated or included within liposome particles. In another, the vector may be, e.g., associated or included in a complex with dendrimers, e.g., poly(amidoamine) (PAMAM)-based dendrimer and positively charged, activated dendrimers, such as SuperFect or PolyFect (Qiagen). Additionally, in yet another embodiment, the vector may be associated with nano- or micro-particles, e.g., micro-gold biolistic particles used in Helios gene gun (BioRad).

In one embodiment, the vector has schematic as set forth in FIG. 9B or 9C.

Suitable examples of a viral vector include but are not limited to a retrovirus vector, lentivirus vector, adeno virus vector, adeno-associated virus vector, DNA virus vector, herpes simplex virus vector, and chimeric adeno-associated virus vector. In one embodiment, the lentivirus vector is derived from human immunodeficiency virus (HIV), e.g., a human immunodeficiency virus-1 (HIV-1).

The HIV-derived vector may contain a central DNA flap, having, e.g., a polypurine tract sequence (cPPT) and a central termination sequence (CTS) from the HIV polymerase (pol) gene and facilitating nuclear import of the viral preintegration complex.

Further, the HIV-derived vector may contain woodchuck hepatitis virus posttranscriptional regulatory element, WPRE, to e.g., increase transgene expression in the context of plasmid DNAs or viral vectors.

Additionally, in one embodiment of the invention, the expression system further comprises a reverse transactivator neuronal target gene that regulates expression of Caveolin-1. For example, a reverse transactivator neuronal target gene may be regulated by doxycycline.

Methods of the Invention

Additionally, the invention further provides methods for promoting neural cell growth or neural stem cell growth comprising administering Caveolin-1 to neural cells in a sufficient amount so as to promote neural cell growth or neural stem cell growth.

The Caveolin-1 so administered may be recombinant Caveolin-1 obtained by expressing the Caveolin-1 gene of different mammals including but not limited to humans, horses, cows, cats, dogs, rabbits, rats, monkeys, and mice and additionally also from non-mammals including chicken, worms, and fishes. Caveolin-1 may be administered directly as a protein or indirectly as a gene that can be expressed in neural cells or neural stem cells (e.g., through gene therapy).

In one embodiment, the method provides transferring the caveolin-1 gene in a neural stem cell or neuronal cell comprising introducing the expression system of the invention into the neural stem cell or neuronal cell, thereby transferring the caveolin-1 gene into a neural stem cell or neuronal cell, respectively. The expression system thereby expresses the Caveolin-1 thereby administering Caveolin-1 to neural cells or neural stem cells.

In accordance with the practice of the invention, the neural stem cell or neuronal cell may be from any mammal, including but not limited to, a dog, cat, rat, rabbit, mouse, horse, donkey, monkey, and human.

Also, the Caveolin-1 gene and resulting protein may be from any mammal, including but not limited to, dog, cat, rat, rabbit, mouse, horse, donkey, monkey, and human.

Merely by way of example, the neuronal cell may be derived from, including but not limited to, brain cortex, cerebrum, hippocampus, thalamus, hypothalamus, amygdala, corpus callosum, tectum, tegmentum, cerebellum, pons, and medulla.

The invention also provides methods of transferring the caveolin-1 gene into a producer cell. In one embodiment, the method comprises introducing the expression system of the invention into the producer cells and permitting the expression system to be incorporated as part of the genome of the producer cells (or maintained as an autonomously replicating episomal DNA in the nucleus of the producer cells). Optionally, the method may further include the step of selecting producer cells in which the expression system is incorporated as part of the genome of the producer cells (or maintained as an autonomously replicating episomal DNA in the nucleus of the producer cells). The producer cell may men express caveolin-1 protein from the caveolin-1 gene so transferred. Gene transfer may be effected ex vivo, in vivo, or in vitro.

In an embodiment of the invention, the producer cell is a neural cell or a stem cell.

In accordance with the practice of the invention, the producer cell may be grafted or transferred into a subject. Subjects include but are not limited to a dog, cat, rat, rabbit, mouse, horse, donkey, monkey, and human.

The invention further provides methods for increasing the expression of Caveolin-1 in a subject.

In one embodiment, the method comprises transferring a caveolin-1 gene into producer cells by the transfer method of the invention above and grafting or transferring the producer cells into the subject, e.g., to a desired location in the nervous system (e.g., the brain), thereby increasing the expression of Caveolin-1 in the subject.

In another embodiment, the method comprises transferring the caveolin-1 gene into neural stem cells or neural cells introducing the expression system of the invention into the neural stem cell or neuronal cell, thereby transferring the caveolin-1 gene into a neural stem cell or neuronal cell, respectively. The Caveolin-1 may then be expressed in the neural cells or neural stem cell, thereby increasing the expression of Caveolin-1 in the subject. One transfer method would be through transfection with chemical agents to introduce the expression vector or DNA either circular or linear into neural stem cells or neural cells. Another method would be microinjection into the recipient cell. Other methods include liposome-mediated transfer of the vector or DNA, dendrimer-based reagents for transfection of nucleic acids such as SuperFect or PolyFect (Qiagen), and biolistic projection of nano- or micro-particles, such as micro-gold particles, using a Helios gene gun (BioRad). Transfers may also be mediated by virus or viral particles containing within its RNA or DNA genome sequences corresponding to the caveolin-1 expression system.

In yet a further embodiment, the method comprises administering Caveolin-1 protein, in neural stem cells or neural cells of the subject, thereby increasing the level of Caveolin-1 in the subject.

Further provided are methods of increasing synapse formation and improving synaptic function in neurodegenerative diseases by increasing the expression or level of Caveoline-1 in the subject by any of the methods of the invention, thereby increasing synapse formation and improving synaptic function.

Examples of neurological diseases or disorders include but are not limited to Alzheimer's disease, hemorrhagic stroke associated with traumatic brain injury (TDI), hemorrhagic or ischemic stroke, spinal cord injury, peripheral nerve injury, Amyotrophic lateral sclerosis (ALS), cerebro-vascular amyloidosis (HCHWA), or cerebral amyloid angiopathy (CAA), idiopathic dilated cardiomyopathy, Down Syndrome (DS), Parkinson's Disease (PD), Lewy Body Dementia (LBD), Prion Diseases, Inclusion Body Myositis (IBM) and Huntington's Disease (HD).

Additionally, the invention provides methods of increasing the efficacy of serotonin and dopamine regulated signal transduction by increasing the expression or level of Caveolin-1 in the subject by any of the methods of the invention, thereby increasing the efficacy of serotonin regulated signal transduction.

Further, the invention also provides methods of treating depression in a subject comprising increasing the efficacy of serotonin and dopamine regulated signal transduction by increasing the expression or level of Caveolin-1 in the subject by any of the methods of the invention, thereby treating depression in a subject.

Also provided are methods for increasing synapse formation and improve synaptic function in the brain and spinal cord of subjects who have sustained ischemic (e.g., stroke) or traumatic injury by increasing the expression or level of Caveolin-1 in the subject by any of the methods of the invention, thereby increasing synapse formation and improve synaptic function in the brain and spinal cord of subjects who have sustained ischemic or traumatic injury.

The invention further provides methods of improving the efficacy of transplanted stem cells for purposes of regenerating or repairing the central nervous system by increasing the expression or level of Caveolin-1 in the subject by any of the methods of the invention, thereby improving the efficacy of transplanted stem cells.

Additionally provided are methods of increasing neuronal membrane/raft formation, neurotransmitter and neurotrophin receptor expression, NMDA- and BDNF-mediated prosurvival kinase activation, agonist-stimulated cAMP formation, dendritic growth, arborization, and neuronal growth by increasing the expression or level of Caveolin-1 in the subject by any of the methods of the invention, thereby increasing neuronal membrane/raft formation, neurotransmitter and neurotrophin receptor expression, NMDA- and BDNF-mediated prosurvival kinase activation, agonist-stimulated cAMP formation, dendritic growth, arborization, and neuronal growth.

Further provided are methods of enhancing dendritic growth in the presence of inhibitory cytokines and myelin-associated glycoproteins by increasing the expression or level of Caveolin-1 in the subject by any of the methods of the invention, thereby enhancing dendritic growth in the presence of inhibitory cytokines and myelin-associated glycoproteins. Suitable examples of inhibitory cytokines include but are not limited to tumor necrosis factor alpha (TNF-α) and interleukin-1 beta (IL-1β).

Examples of suitable myelin-associated glycoproteins include but are not limited to MAG and Nogo.

The invention also provides methods for decreasing Aβ protein level in a neuronal cell by increasing the expression or level of Caveolin-1 in the subject by any of the methods of the invention, thereby decreasing Aβ protein level in a neuronal cell.

Dosages

The appropriate dosage of Caveolin-1 for use in accordance with the methods of the present invention may depend on a variety of factors. Such factors may include, but are in no way limited to, a subject's physical characteristics (e.g., age, weight, sex), whether the compound is being used as single agent or adjuvant therapy, the progression (i.e., pathological state) of the disease, and other factors that may be recognized by one skilled in the art.

One skilled in the art would be able, by routine experimentation, to determine an effective, non-toxic amount of Caveolin-1 which would be required to treat the subject.

Typically, in therapeutic applications, the treatment would be for the duration of the disease state or condition. Further, it will be apparent to one of ordinary skill in the art that the optimal quantity and spacing of individual dosages will be determined by the nature and extent of the disease state or condition being treated, the form, route and site of administration, and the nature of the particular individual being treated. Also, such optimum conditions can be determined by conventional techniques. It will also be apparent to one of ordinary skill in the art that the optimal course of treatment can be ascertained using conventional course of treatment determination tests.

Where two or more therapeutic entities are administered to a subject "in conjunction", they may be administered in a single composition at the same time, or in separate compositions at the same time or in separate compositions separated in time. In certain embodiments, the methods of the invention involve the administration of Caveolin-1 (by means of any of the methods of the invention) in multiple separate doses.

Kits

According to another aspect of the invention, kits are provided. Kits according to the invention include package(s) or containers comprising any of the compositions of the invention or the Caveolin-1 expressed thereby. The kit may further include an instruction letter for the treatment and/or prophylaxis of a disease, for example, a veterinary disease.

The phrase "package" means any vessel containing compounds or compositions presented herein. In preferred embodiments, the package can be a box or wrapping. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering Caveolin-1 or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package (s) is a container for intravenous administration. In still other embodiments compounds are provided in a polymeric matrix or in the form of a liposome.

The following examples are provided to further illustrate aspects of the invention. These examples are non-limiting and should not be construed as limiting any aspect of the invention.

EXAMPLES

Example 1

Materials and Methods

All studies performed on animals were approved by Veteran Affairs San Diego Institutional Animal Care and Use Committee (Protocol*: 08-035 and ID#: 1141788) and conform to relevant National Institutes of Health guidelines, Primary Neuron Isolation and Culture Neonatal mouse neurons were isolated using a papain dissociation kit (Worthington Biochemical, Lakewood, N.J.) as previously described [27]. Neurons were cultured in Neurobasal A media supplemented with B27 (2%), 250 mM GLUTMax1, P/S (1%). Cells were cultured on poly-D-lysine/laminin (2 pg/cm2) coated plates at 37° C. in 5% CO2 for 4 d prior to transfection with lentiviral vectors. Cav-1 cDNA was cloned in our laboratory and given to Dr. Atushi Miyanohara at the UCSD Viral Vector Core. Dr. Miyanohara successfully generated a lentiviral vector containing the synapsin promoter up-stream of the Cav-1 gene (SynCav1), SynGFP was used as control vector. Titer for both vectors was approximately 109 infectious units (i.u.) per µl.

Sucrose-Density Fractionation

Membrane/lipid rafts were isolated from adult brain and neurons using detergent-free methods. Tissue and cells were homogenized in sodium carbonate (150 mM, pH 11.0), and then sonicated with three cycles of 20 sec bursts with 1 min incubation on ice. Homogenate (1 mL) was mixed with 1 mL of 80% sucrose to generate 2 mL of 40% sucrose. Above the 40% layer, 6 mL of 35% and 4 mL of 5% sucrose were carefully layered. The mixture was centrifuged at 175,000 g using SW41Ti rotor (Beckman) for 3 h at 4° C. Samples were removed in 1 ml aliquots and the membrane/lipid rafts are found in buoyant fractions 4-5 (5/35% interface).

Synaptosomal Membrane Preparation

Neuronal cells or brain tissue were homogenized in 5 ml of solution A [0.32 M sucrose (34 g/500 ml), 0.5 mM CaCl2 (36 mg/500 ml), 1 mM NaHCO3 (42 mg/500 ml), 1 mM MgCl2 (102 mg/500 ml)] containing protease and phosphatase inhibitors with 12 strokes of a 19×84 mm tissue grinder (Potter Elvehjem, plastic coated) at 800 r.p.m. Samples were then subjected to centrifugation for 10 min at 1000 g at RT to remove large debris. Centrifugation 1 involved careful layering of the supernatant onto 4 ml of 1.2 M sucrose (41 g/100 ml or 41% sucrose) in a SW41 centrifuge tube (Beckman) and then spun at 160,000 g for 15 min (or 33,000 r.p.m. with SW41 rotor). The synaptosomes were found at the interface between the 1.2 M and 0.32 M sucrose layers. The synaptosomes were then mixed with 4 ml of 0.32 M sucrose and then carefully layered onto 4 ml of 0.S M sucrose (or 27% sucrose) in a fresh centrifuge tube for second major centrifugation. Centrifugation 2 consisted of spinning the sample at 160,000 g for 15 min (33,000 rpm with SW41 rotor) generating a pellet enriched in the synaptosomes. The pellet was then resuspended in 1 ml of neuronal lysis buffer containing protease and phosphatase inhibitors and used for immunoprecipitation and/or immunoblot analysis.

Determination of Synaptosomal Membrane Fluidity using Electron Paramagnetic Resonance (EPR)

Hydrocarbon chain mobility was measured using fatty acid spin labeling EPR analysis using 5-nitroxyl stearate (5-DSA, Aldrich) as a spin probe [76,77]. The number 5 designation indicates the relative position of the nitroxide on the stearic acid relative to the polar carboxylic group. In the case of 5-DSA, the spin probe is firmly held in place by the head groups of the lipids, which is reflected in broad EPR lines. Synaptosomes from young (3-6 m) and aged (>18 m) mice were isolated as described previously [78]. Freshly prepared synaptosomal protein (0.1-0.2 mg) was incubated for 15 minutes with 5-DSA (1 mM final concentration) in synaptosomal buffer (120 mM NaCl, 4.7 mM KCl, 2.2 mM $CaCl_2$, 1.2 mM $MgCl_2$, 25 mM HEPES, 1.2 mM $MgSO_4$, 1.2 mM $KH_2PO_4$, 10 mM glucose) at 25° C. The mixture was then loaded into a 50 µl-glass capillary and inserted into the EPR cavity of a MiniScope MS200 Benchtop spectrometer (Magnettech, Berlin), maintained at 37° C., where the EPR spectra registered. EPR conditions were the following: microwave power, 5 mW; modulation amplitude, 2 G; modulation frequency, 100 kHz; sweep width, 150 G centered at 3349.0 G; scan rate, 7.5 G/s, with each spectrum representing the average of 5 scans. The fluidity parameters T∥ and T⊥ are defined in FIG. 2E and are used to calculate the order parameter as previously described [76,77].

In Vivo BCAO (Bilateral Carotid Artery Occlusion) Model of Neuronal Preconditioning Male C57BL/6J and Cav-1 KO mice were anesthetized with isoflurane. After endotracheal intubation, the lungs were mechanically ventilated with 1.5% isoflurane in 30% $O_2$, balanced $N_2$. Pericranial temperature was controlled at 37° C. Via a pre-tracheal incision, the carotid arteries and the basilar artery were exposed and a temporary clip was applied to the basilar artery. Thereafter, preconditioning (PC) was induced by occlusion of the carotid arteries. The clips were removed after a defined interval (3 min for PC and 10 min for lethal ischemia), the wounds were infiltrated with 0.25% bupivacaine and the anesthetic was discontinued. Upon resumption of spontaneous ventilation, the endotracheal tube was removed and the animals were transferred to the animal care facility 4 hr post extubation. Animals underwent transcardiac perfusion with heparinized saline followed by buffered paraformaldehyde. The brains were removed and the extent of injury to the CA1 sector of the hippocampus was determined by Cresyl violet staining.

Routine and Immunoelectron Microscopy

Brains were transcardially perfusion fixed with standard Karnovsky's fix, 4% paraformaldehyde, 1% gluteraldehyde, 0.1 M cacodylate buffer with 5 mM $CaCl_2$. PND5-7 animals were fixed with 2% paraformaldehyde, 2.5% glutaraldehyde, 0.1 M cacodylate buffer and 5 mM $CaCl_2$ to prevent tissue artifacts. Hippocampi were dissected from whole brains after 24 h and 400 um vibratome slices prepared and re-fixed an additional 24 h. Brains were blocked (i.e., dissected) to include hippocampal areas, one hemisphere for sagittal orientation, and one hemisphere for coronal. Blocks were re-fixed for an additional 24 h followed by post-fixation with 1% $OsO_4$ in 0.1 M cacodylate buffer, en bloc stained with uranyl acetate and embedded with flat orientation to locate appropriate hippocampal regions of interest. Each block was thick sectioned, stained with toludine blue, and re-trimmed to isolate hippocampal areas prior to preparation of grids. Grids (70 nm sections) were stained with uranyl acetate and lead nitrate for contrast and observed on the electron microscope [JEOL 1200 EX-II (Tokyo, Japan)] equipped with a digital camera system. 25 random low magnification micrographs of the stratum radiatum were obtained from each specimen. Micrographs were analyzed for the quantity of synapses and for synapse abnormalities (reduction or changes in synapse and dendritic filopidal spine morphology, i.e., degradation of cytoskeletal architecture). The dendritic profiles were characterized by abundant organelles such as mitochondria and endoplasmic reticulum and frequent contacts from vesicle-filled axon terminals. Spine synapses were identified by an electron dense region associated with vesicles pre-synaptically and that lacked cellular organelles or contained a spine apparatus (as indicated by cytoskeletal architecture) with post-synaptic densities as described previously. [79,80,81,82] Approximately 25 electron micrographs (3350 µm2) per animal were analyzed in a blinded fashion for total synapse number per area (synapse #13350 µm2).

Generation of SynCav 1 Construct

To link the neuron-specific synapsin (Syn) promoter with the Cav1 cDNA, XbaI-SalI DNA fragment containing the Syn promoter was inserted into the NheI-SalI sites of the pEGFP-N1 (Clontech) and the resulting plasmid was designated pSyn-EGFP. A 685 bp Cav1 cDNA was isolated from the pCRII-TOPO vector (Invitrogen) by PmeI-NotI digest and inserted into the SmaI-NotI site of the pSyn-EGFP to generate the pSyn-Cav1, in which the EGFP gene was replaced with the Cav1 cDNA. The Syn-promoter-Cav 1 cassette was isolated from the pSyn-Cav1 and inserted into the BamHI site of the HIV1 vector backbone plasmid pHIV7 [83] and the resulting plasmid was designated pHIV1-Syn-Cav1.

Statistics

All parametric data were analyzed by unpaired t-tests or ANOVA Bonferroni's Multiple Comparison as appropriate; post hoc comparisons were made by Student Neuman Keuls tests. Significance was set at p<0.05. Statistical analysis was performed using Prism 4 (GraphPad Software, Inc., La Jolla, Calif.).

Results

PSD-95, NR2A, NR2B, and Cav-1 Protein Expression Is Decreased in Middle Aged and Aged Hippocampus Hippocampi were isolated from brains of C57BL/6J mice (wild-type, WT) at 3-6 months (young), 12 months (middle aged), and >18 months (aged). Immunoblots of hippocampal homogenates showed a significant reduction in PSD-95, NR2A, NR2B, TrkB, and Cav-1 in hippocampi from middle aged and aged mice when compared to young mice (FIG. 1). These data demonstrate an age-dependent reduction in synaptic signaling components and Cav-1 in the hippocampus.

Age-Related Decreases in Synaptic Signaling Components from MLR

Figure 2A:
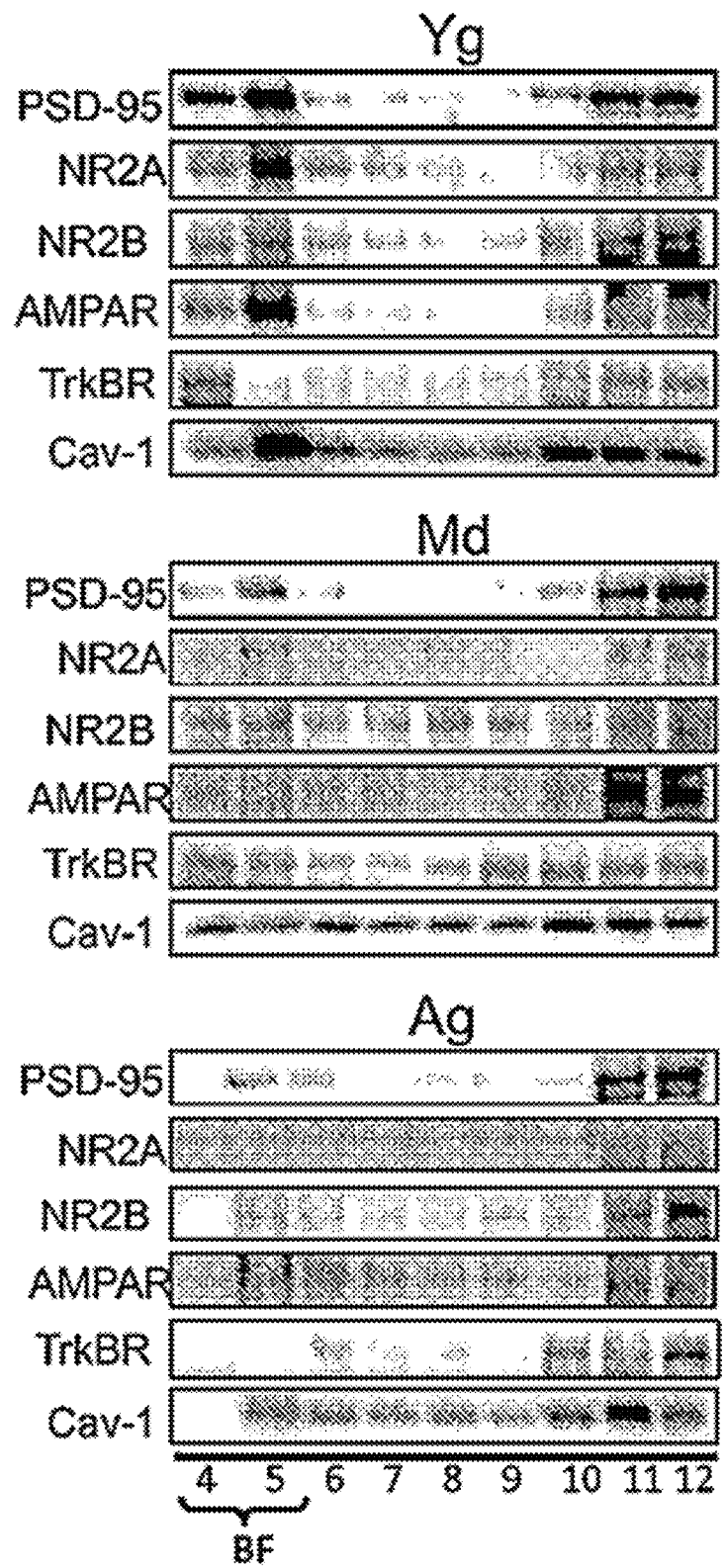
FIG. 2A-E shows PSD-95, NR2A, NR2B, AMPAR, TrkBR, and Cav-1 are abundantly detected in buoyant fractions (BF) from young mouse brains homogenates, yet are less abundant BFs from middle aged and aged brains. Sucrose density fractionated was performed on brains from three different age groups of C57BL/6J mice: young (Yg, 3-6 months), middle aged (Md, 12 months), and aged (Ag, >18 months). Immunoblot analysis detected the majority of PSD-95 (post-synaptic density marker), NR2A, NR2B, AMPAR, TrkBR, and Cav-1 in buoyant fractions 4 and 5 (BFs) isolated from Yg brains (A). In contrast, the Md and Ag brains exhibited a drastic reduction in these synaptic signaling components, with the majority of these proteins detected in heavy fractions 11 and 12 (HFs) only. Densitometric analysis of the data is represented in (B) and is representative of 4-7 mice per age group (*$p<0.05$). (C) Cav-1 (C) and PSD-95 (P) immunoprecipitates pulled down NR2A, NR2B, AMPAR, and TrkB in the buoyant fractions of Yg mice, with decreased detection in Md and Ag. (D) Immunoblot analysis detected a significant decrease in PSD-95 (post-synaptic density marker), NR2A, NR2B, AMPAR, and Cav-1 in hippocampal synaptosomes from Md and Ag brains compared to Yg (*$p<0.05$, n=6). PSD-95, NR2, NR2B, AMPAR, and Cav-1 decreased in PSD-95 immunoprecipitates of Md, and Ag synaptosomes compared to Yg, (E) Electron paramagnetic resonance (EPR) was performed on synaptosomal membranes from brains of C57BL/6J mice: young (Yg, 3-6 months) and aged (Old, >18 months). Membrane localized spin labels 5-doxylstearic acid (5-DSA) probes changes in the neuronal membrane fluidity closer to the membrane surface. Lineshape analysis of 5-DSA spin label using the indicated parameters revealed that neuronal membrane of aged mice exhibit significantly lower order parameter (i.e. increased fluidity) than young animals. Aged membranes were 8.5±1.2% more fluid than young membranes ($F(1,10)=223.5$, $p=0$) (*$p<0.05$).
Figure 2B:
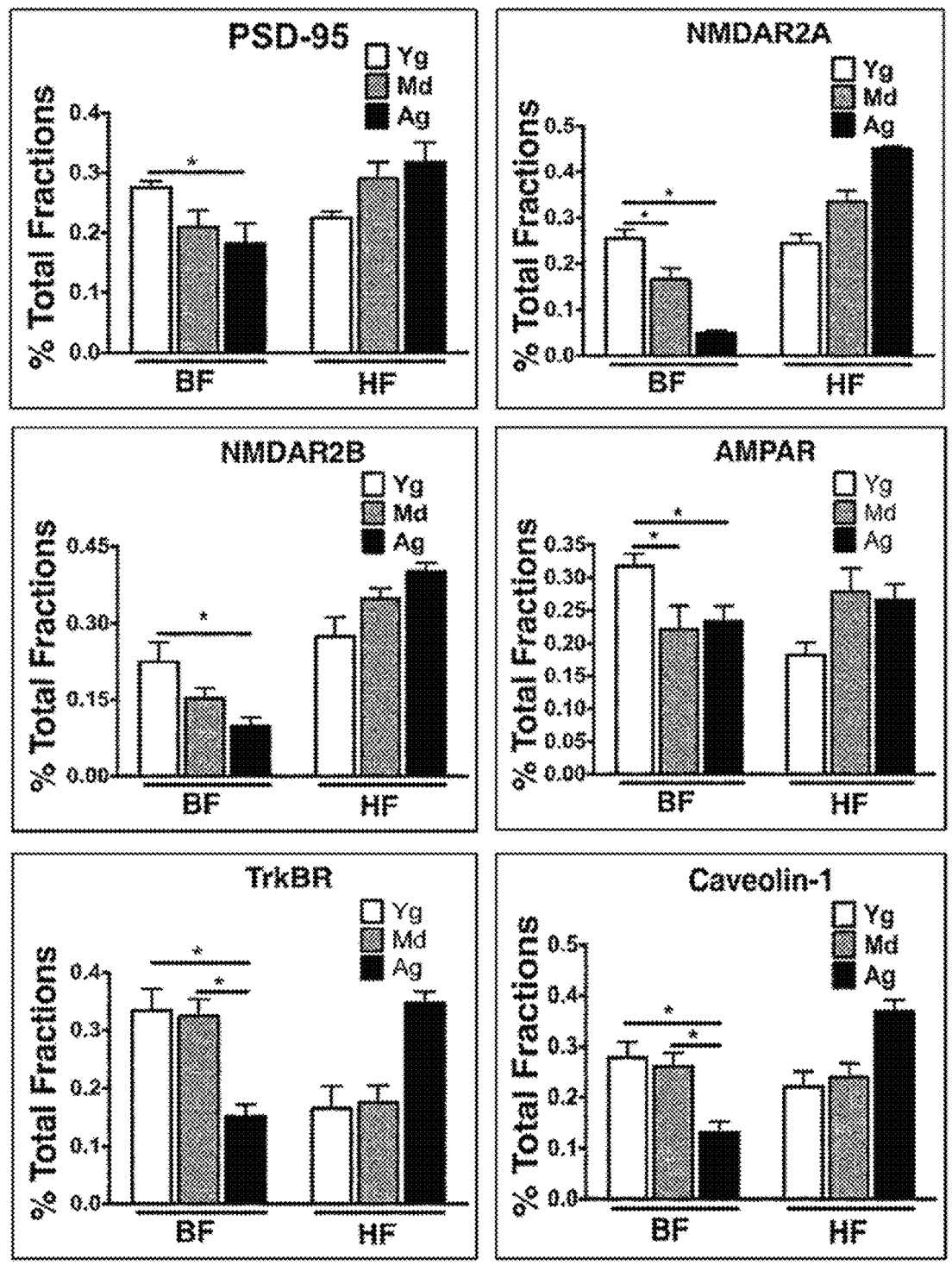
Figure 2C:
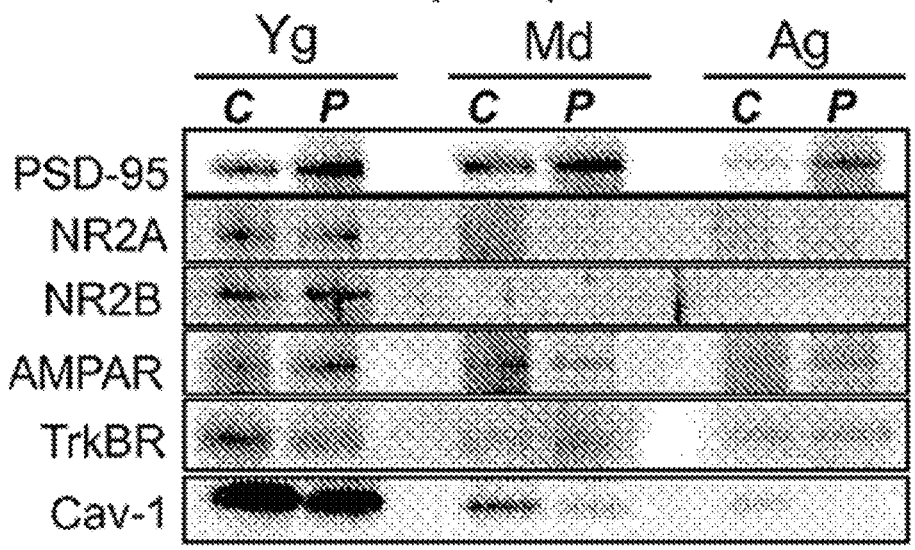

MLR play a role in stabilizing synapses in the mammalian brain,[12,18] therefore we performed sucrose density fractionation of whole brain homogenates from young, middle aged and aged WT mice to purify MLR. Immunoblots showed buoyant fractions from young brains contained the majority of PSD-95, NR2A, NR2B, AMPAR, TrkB, and Cav-1 (FIG. 2A,B) In contrast, buoyant fractions from the middle aged and aged brains showed a reduction in synaptic signaling components, with the majority of the proteins detected in heavy fractions, 11 and 12 only. Cav-1 (Q and PSD-95 (P) co-immunoprecipitated with NR2A, NR2B, AMPAR, and TrkB in the buoyant fractions of Yg mice, with decreased detection in Md and Ag. (FIG. 2C). These data demonstrate an age-dependent decrease in synaptic signaling components including Cav-1 from MLR and PSD-95 immunoprecipitation of MLR.

Figure 2D:
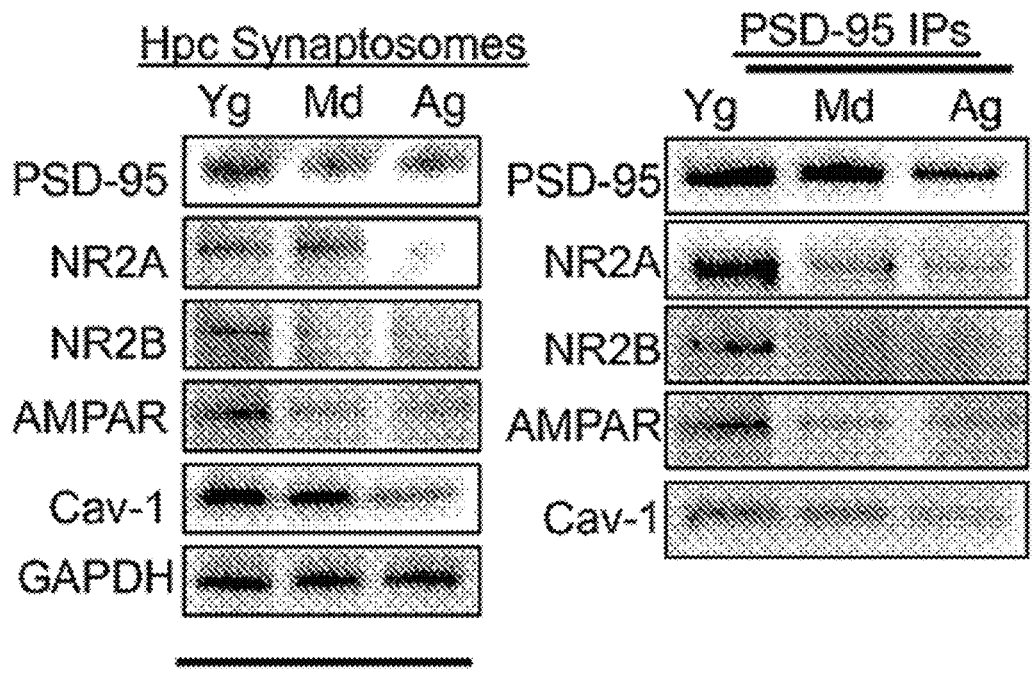
Figure 2E:
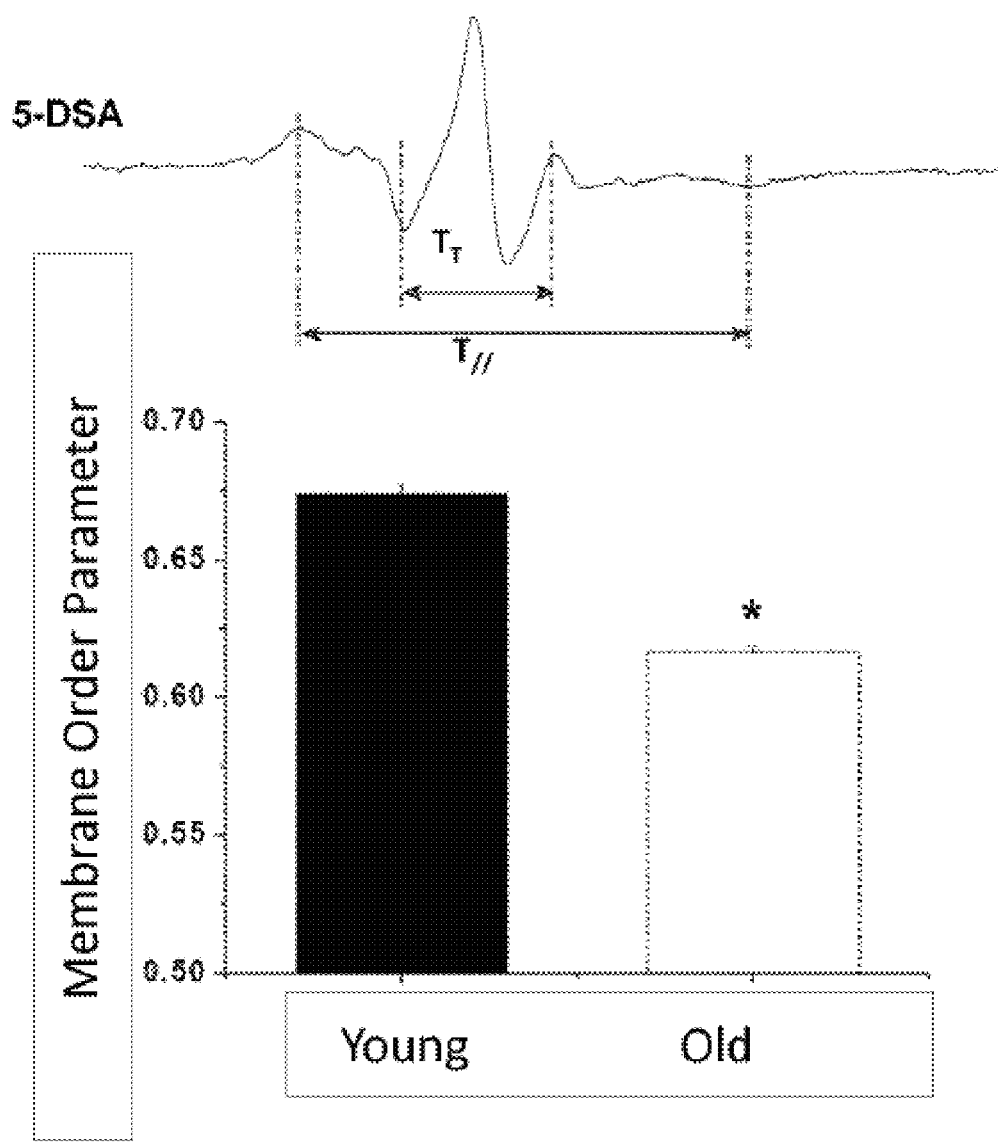

Previous work has shown that MLR facilitate neuronal synapse formation. [12, 18] We sought to confirm whether the age-related decrease in synaptic signaling components in MLR also occurred in synaptosomes purified from hippocampi of young, middle aged, and aged WT mice. Immunoblots and immunoprecipitates of synaptosomes from middle aged and aged mice showed a significant decrease in PSD-95, NR2A, NR2B, AMPAR, and Cav-1 relative to young mice (FIG. 2D). Assessment of membrane fluidity of synaptosomes isolated from whole brain of young and aged mice using electron paramagnetic resonance showed that membranes of aged mice had significantly lower membrane order parameter (greater fluidity) than membranes from young animals (FIG. 2E). These findings suggest that age-related decrease in MLR and Cav-1 expression are associated with increased membrane fluidity (i.e., increased liquid-disordered phase). [37]

Young Cav-1 KO Mice Demonstrate Accelerated Aging and Neuro Degeneration

Loss of Synaptic Proteins and Neuronal Preconditioning

Figure 3A:
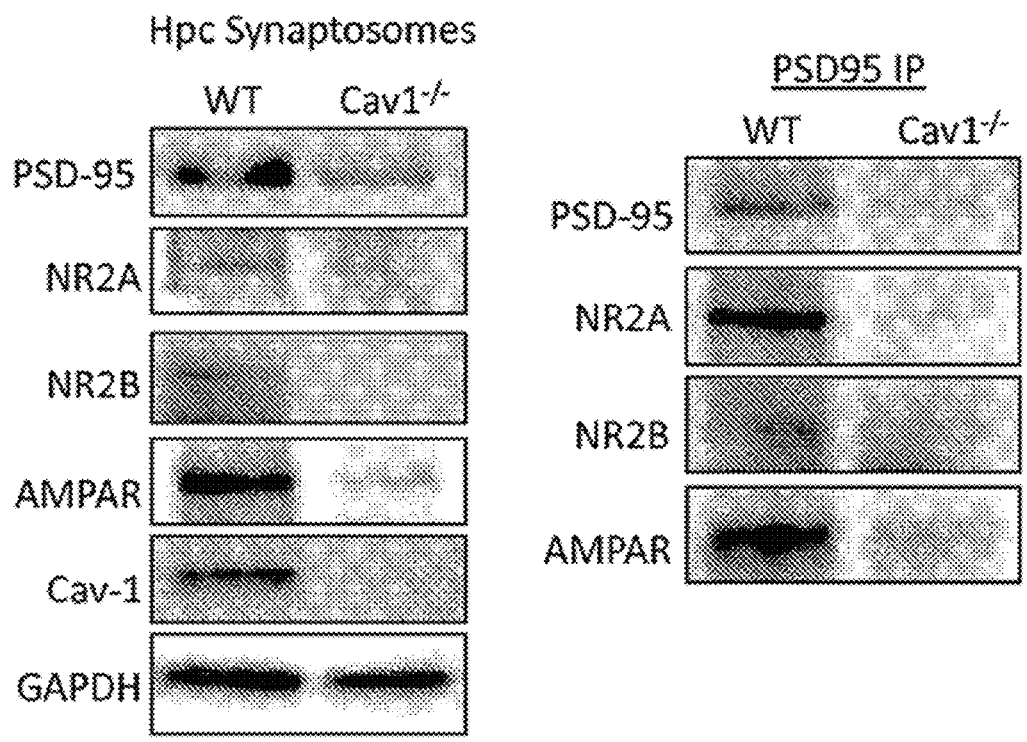
FIG. 3A-C shows Ischemic preconditioning (IPC) does not occur in Cav-1 KO mice. (A) Hippocampal synaptosomes from Cav-1 KO (Yg) showed a similar pattern to Ag, with a decrease in PSD-95, NR2A, NR2B, and AMPAR. PSD-95 IPs of Cav-1 KO synaptosomes revealed minimal detection in PSD-95, NR2A, NR2B, and AMPAR. (B) WT or Cav-1 KO mice were subjected to 3 min (ischemic preconditioning, IPC) and/or 12 min (lethal ischemia, LI) induced by bilateral carotid artery occlusion (BCAO). Intact neurons in CA1 hippocampal (HP) region were counted from Cresyl Violet stained paraffin fixed sections. IPC (3 min, BCAO) significantly protected CA1 neurons against LI (12 min, BCAO) in WT mice (iv, ***$p<0.0001$, n=7). There was a significant increase in CA1 neuronal death in Cav-1 KO animals subject to IPC (viii) versus WT IPC+LI. Representative Cresyl Violet stained CA1 hippocampal images from (i) WT sham, (ii) WT IPC, (iii) WT LI, and (iv) WT IPC and (v) Cav-1 KO sham, (vi) Cav-1 KO IPC, (vii) Cav-1 KO LI, and (viii) Cav-1 KO IPC. Quantitation of images is presented by the graph (C).

Cav-1 expression is decreased in hippocampi and buoyant fractions (i.e., MLR) from aged mice (FIGS. 1 and 2), we therefore assessed whether Cav-1 KO mice display reduced synaptic protein expression. Hippocampal synaptosomes from young Cav-1 KO mice showed a similar pattern to aged WT mice, reduced protein expression of PSD-95, NR2A, NR2B, and AMPAR (FIG. 3A). Similar to aged WT mice, PSD-95 immunoprecipitation of hippocampal synaptosomes from Cav-1 KO mice showed minimal detection of PSD-95, NR2A, NR2B, and AMPAR.

Figure 3B:
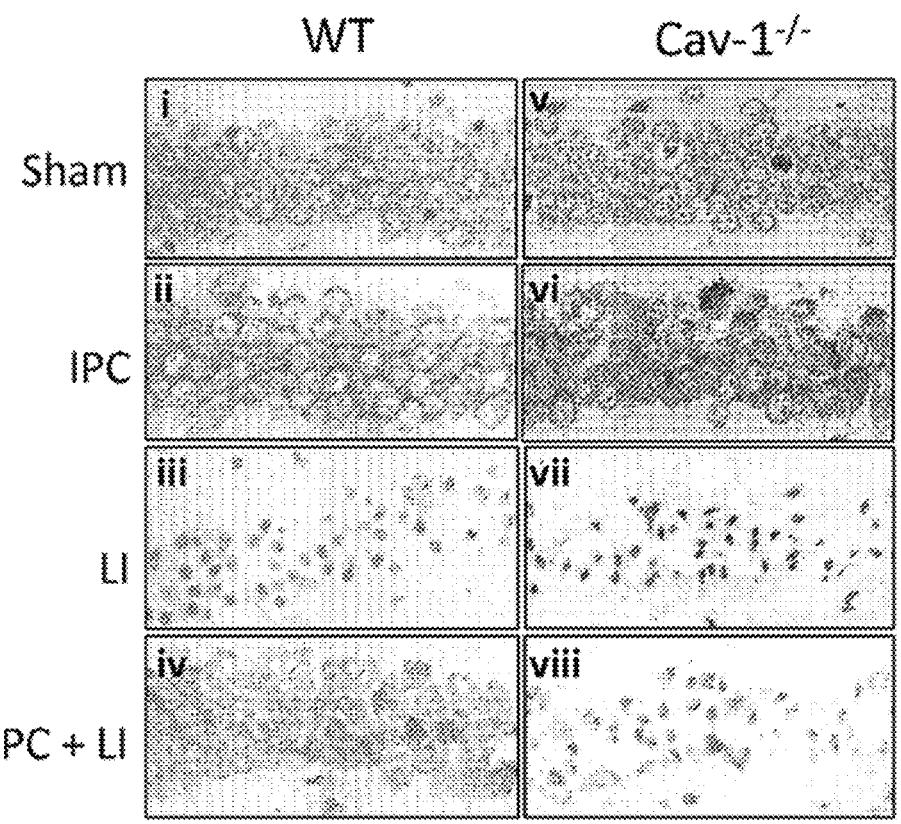
Figure 3C:
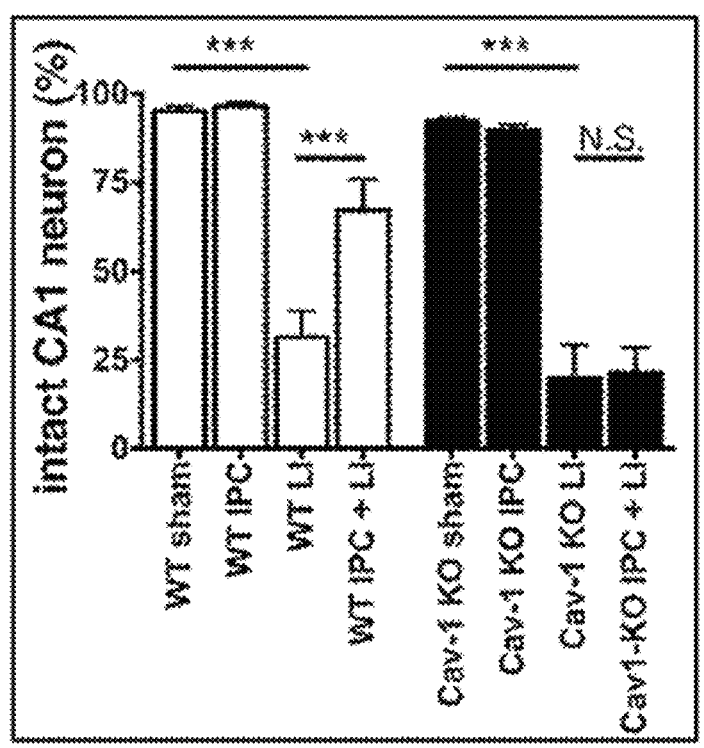

Ischemic preconditioning (IPC), a phenomenon wherein sublethal ischemia protects the brain from a subsequent lethal ischemic event, is absent in brains from aged animals [38,39] and in neurons in vitro that have reduced or no Cav-1 expression. [27] We show here for the first time that Cav-1 KO mice show a similar reduction in neuroprotective signaling components to that exhibited by brains from aged WT mice. IPC protected CA1 neurons against lethal ischemia in WT mice (FIG. 3B-iv). There was a significant increase in CA1 neuronal death in Cav-1 KO mice subjected to IPC versus WT (FIG. 3B-viii). In terms of expression and function of synaptic signaling components, young Cav-1 KO mice resemble aged WT mice.

Early on-Set of AD-Like Phenotype

Figure 4A:
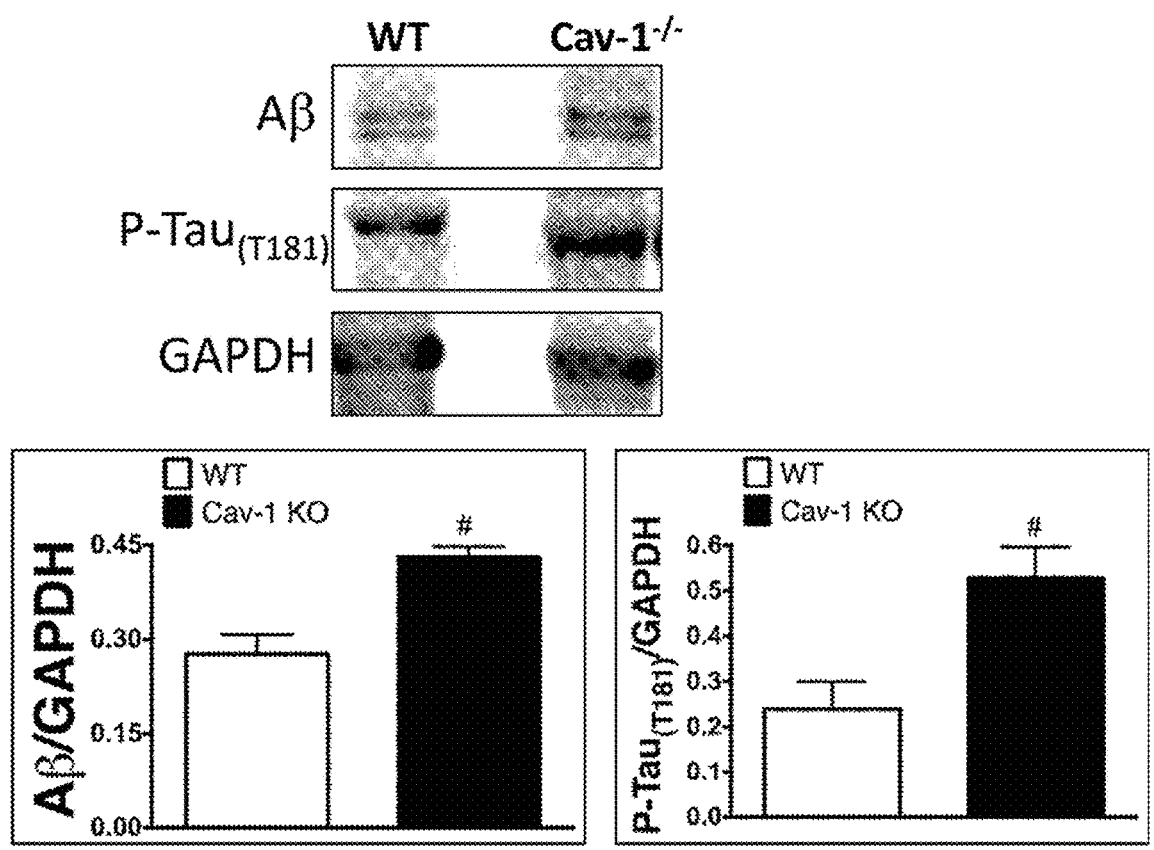
FIG. 4A-C shows Aβ, A4 protein, and P-Tau(T181) are elevated in the hippocampus of young Cav-1 KO mice. (A) Hippocampal homogenates from WT (3 m) and Cav-1 KO (Cav-1 KO, 3-6 m) C57Bl/6J mice were immunoblotted for Aβ and phosphorylated Tau (P-Tau[T181]), and GAPDH. Aβ and P-Tau[T181] were significantly elevated in young Cav-1 KO hippocampal homogenates (#$p<0.05$ vs WT, n=4). (B) Immunofluorescence microscopy showed that Cav-1 KO CA1 region of the hippocampus displayed elevated Aβ staining (green) overlapping with Nissl positive neurons (red) as indicated by yellow fluorescence. Quantitation of the data is represented in the graph (*$p<0.05$, n=4). (C) Cryostat sections (50 μm) of mouse hippocampus were stained with lectin GSA (*Griffonia simplicafolia*) to label blood vessels. There was a 20-25% reduction in overall area occupied by blood vessels in Cav-1 KO (#$p<0.05$ vs WT, n=3-4). Quantitation of the data is represented in the graph (right).
Figure 4B:
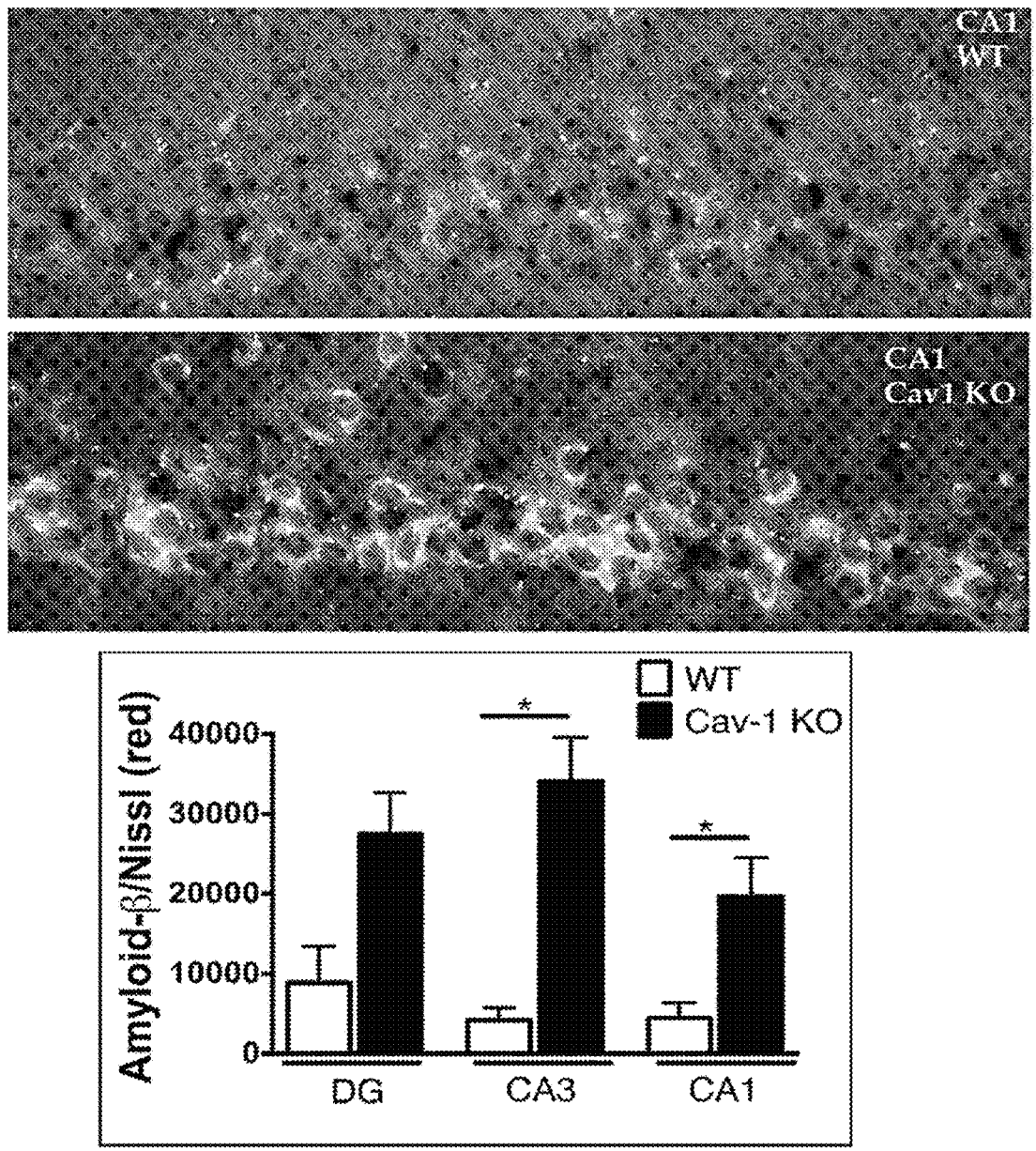
Figure 4C:
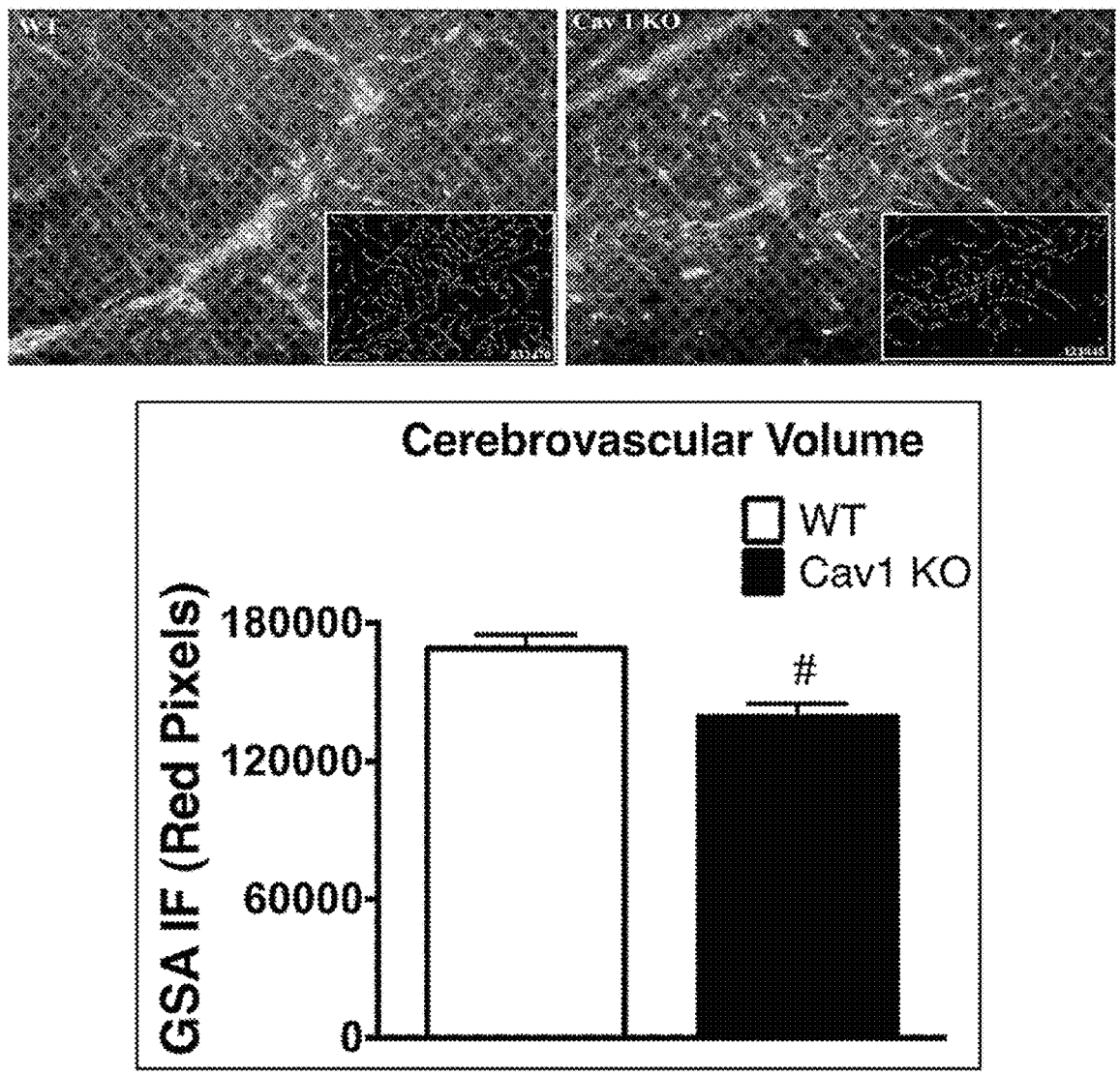

Cav-1 and MLR can regulate amyloidogenic processing of APP.[30] Therefore we assessed whether brains from Cav-1 KO mice have pathological signs indicative AD. $A\beta$ and P-TaU[T181] were significantly elevated in hippocampal homogenates from young Cav-1 KO mice (FIG. 4A). Immunofluorescence microscopy demonstrated that young Cav-1 KO mice had increased $A\beta$ staining in Nissl positive neurons in the CA1 region of the hippocampus compared to WT mice (FIG. 4B). Hippocampi from Cav-1 KO mice showed a 20-25% reduction in cerebrovascular volume (GSA, blood vessel marker—FIG. 4C).

Enhanced Astrogliosis and Neurodegeneration

Figure 5D:
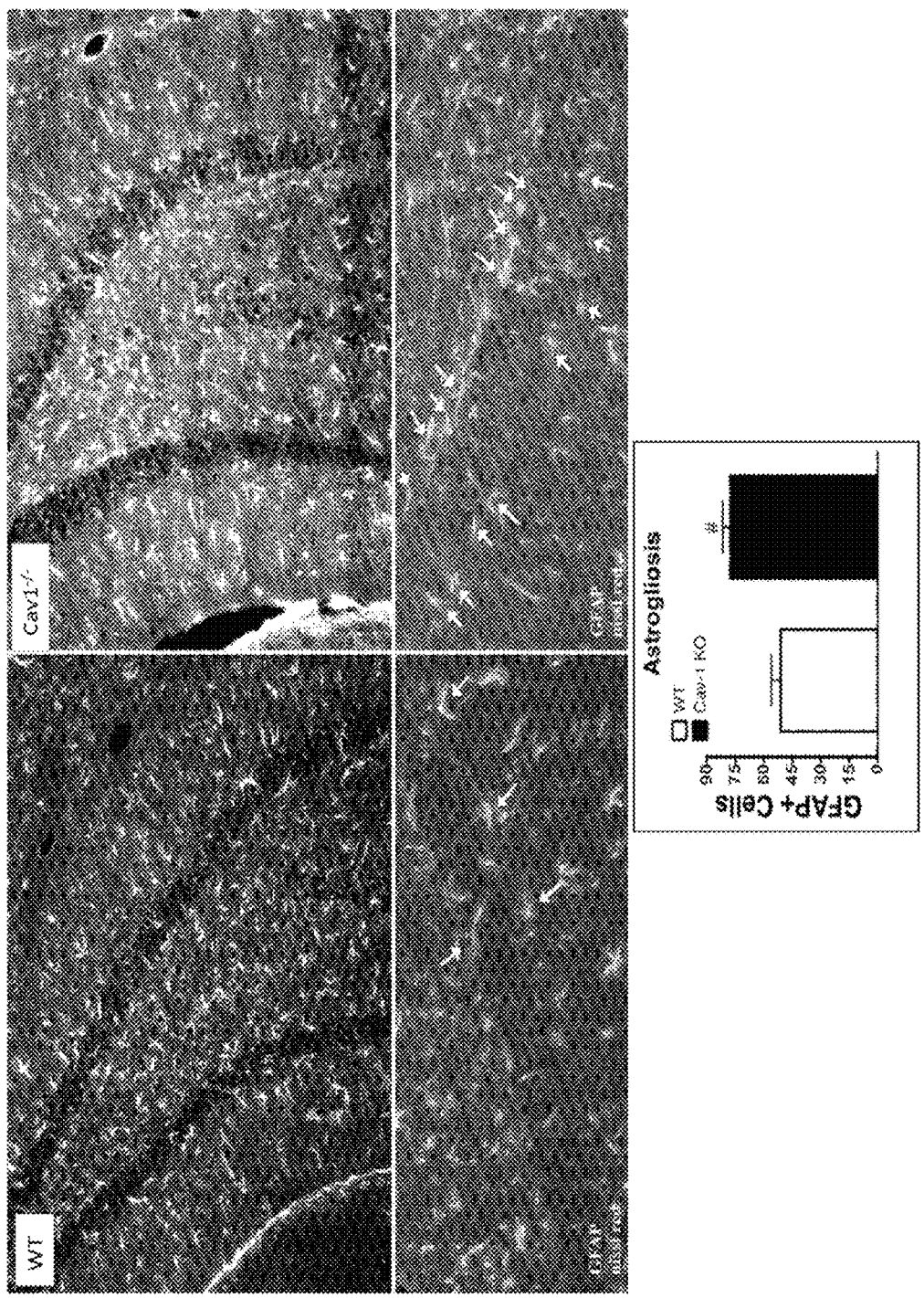
Figure 5E:
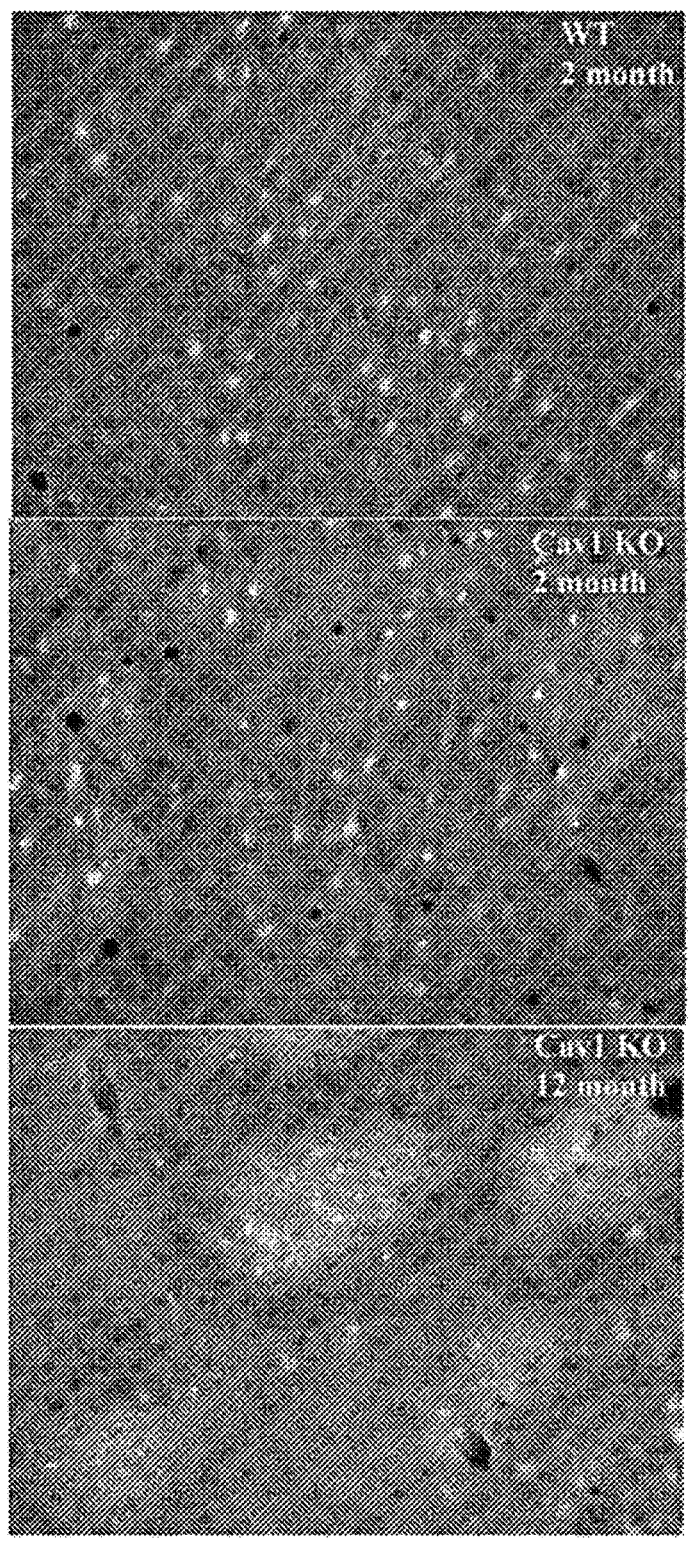
Figures 6A, 6B:
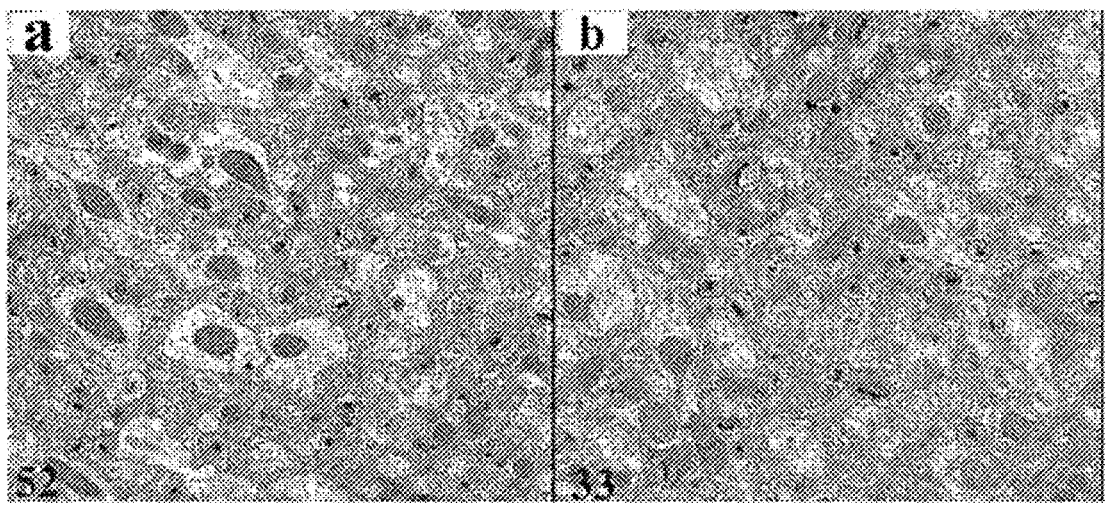
FIG. 6A-G shows Cav-1 KO mice have reduced hippocampal synapses. Synapses were quantified by routine electron microscopy as previously described, [82] EM analysis revealed a significant reduction in hippocampal synapses in both (C) Cav-1 KO (Yg) and (B) Ag mice compared to (A) WT (#$p<0.05$, n=6-9). Synapses are indicated by red circles in WT, blue circles in Ag, and green circles in Cav-1 KO. (D) WT micrographs exhibited dendritic processes (indicated by d) with intact cytoskeletal architecture (arrows and arrowheads), while (E) Ag and (F) Cav-1 KO displayed less organized dendritic shafts (asterisk) with more abundant astrocyte presence (arrows). (G) Quantitation of data.
Figures 6C, 6D:
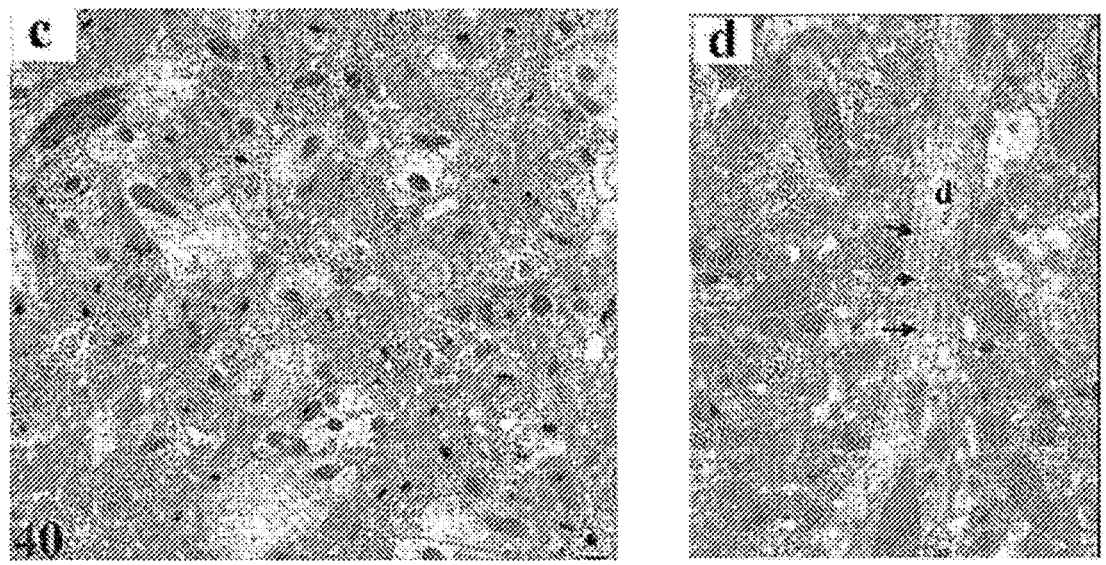
Figures 6E, 6F:
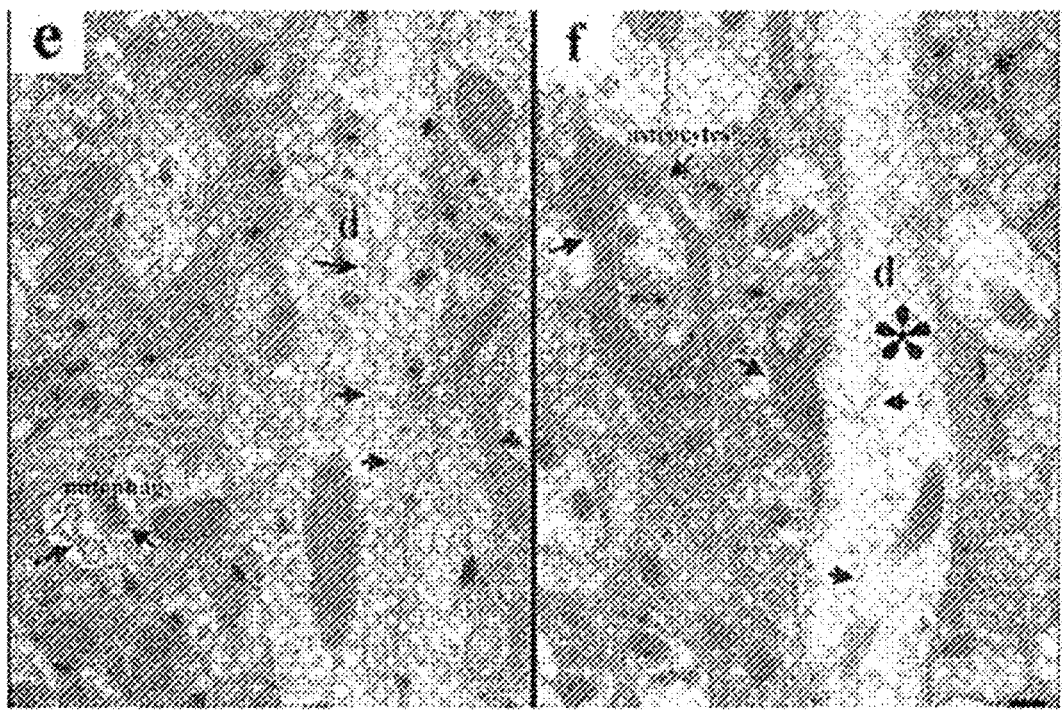
Figure 6G:
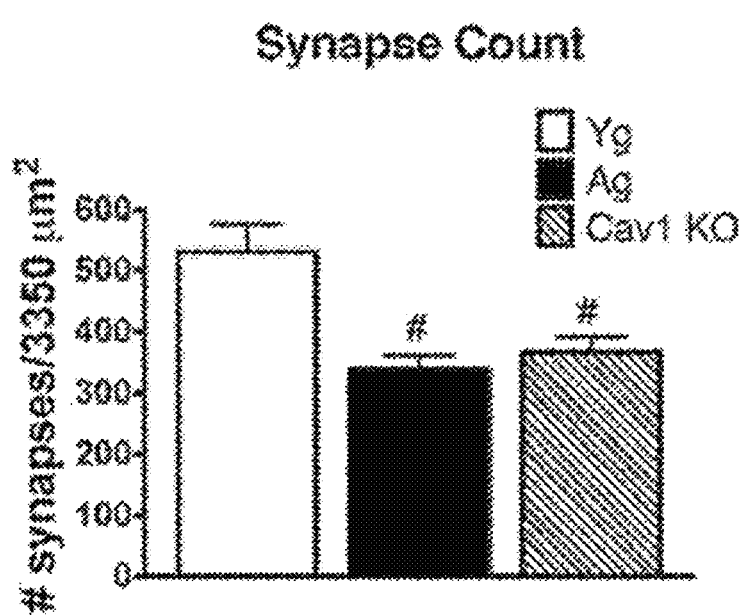

Toludine blue staining of the hippocampus showed a large reduction in neurons within the dentate gyms and CA1 regions of young Cav-1 KO mice (FIG. 5A-i, A-ii) compared to young (FIG. 5C-i, C-ii) and aged (FIG. 5B-i, B-ii) WT mice. In addition, there appeared to be more glia and glial scar formation within the dentate gyms of Cav-1 KO mice as indicated by the darker gray cell bodies intermixed with the neurons (FIG. 5A-i, A-ii). Young Cav-1 KO show increased astrogliosis (GFAP, astrocyte marker—FIG. 5D). Flouro-Jade®B stoning demonstrated little neuronal degeneration and well-organized astrocytes in the CA1 from young WT mice when compared with Cav-1 KO mice, which showed disorganized astrocytes and areas of potential plaque development. Due to their shorter life spine, [40] obtaining older Cav-1 KO mice is difficult. We here show that the CA1 region from 12 month Cav-1 KO mice had large bright, entangled green fluorescence with red fluorescent (Nissl) neurons and severely less organized astrocytes, demonstrating increased neuronal degeneration (FIG. 5E).

There is a reduction in synaptic proteins from hippocampal synaptosomal membranes, we therefore assessed whether Cav-1 KO mice exhibited changes in total hippocampal synapses. Routine electron microscopy (EM) revealed a significant reduction in hippocampal synapses (i.e., post synaptic densities) in both Cav-1 KO (FIG. 6C) and aged (FIG. 6B) mice compared to young (FIG. 6 A). In addition, Cav-1 KO mice displayed unorganized cytoskeletal assemblage (arrow heads) within dendrites (d, asterisks) (FIG. 6F) and elevated astrocyte presence (arrows) compared to brains from aged and young WT mice, the latter displaying normal cytoskeletal organization (arrow heads) within dendrites (d). These data indicate that Cav-1 KO mice develop pathological changes at 3 months of age consistent with aging and AD mouse models.

Re-Expression of Cav-1 in Cav-1 KO Neurons Decreases $A\beta$

Figure 7A:
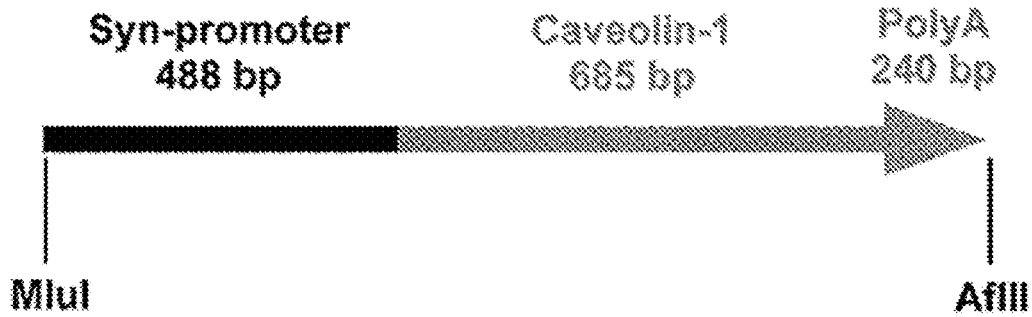
FIG. 7A-C shows Neuron-targeted re-expression of Cav-1 reduces Aβ expression in primary neurons cultured from Cav-1 KO brains. Primary neurons from Cav-1 KO mice were grown in culture for 4 days and transfected with a lentiviral vector containing Cav-1 driven by the synapsin promoter (SynCav1) for 72 hr. SynGFP served as control vector ($2 \times 10^9$ viral particles for both vectors). Schematic of the Syn-promoter-Cav1-PolyA expression cassette unit inserted into the lentiviral vector is shown in (A). DNA fragments that contain the Syn promoter (488 bp: MluI-SalI fragment), Cav-1 coding sequence (~685 bp for ApaI-NotI fragment; 700 bp for SalI-NotI fragment), and SV40 polyadenylation signals (~240 bp; NotI-AflII fragment). A similar expression cassette in which enhanced green fluorescent protein (EGFP) coding sequences of pEGFP-N1 (GenBank Accession No. U55762) is found in place of Cav-1 coding sequence was used to construct SynGFP lentiviral vector, in which synapsin promoter drives the expression of EGFP fluorescent reporter protein. Increasing doses of SynCav1 proportionally decreased Aβ expression (B). Six separate primary cultures of Cav-1 KO neurons were incubated with either SynGFP or SynCav1. SynCav1 significantly decreased Aβ expression after 72 hr (***p<0.0001) as shown in (C).
Figure 7B:
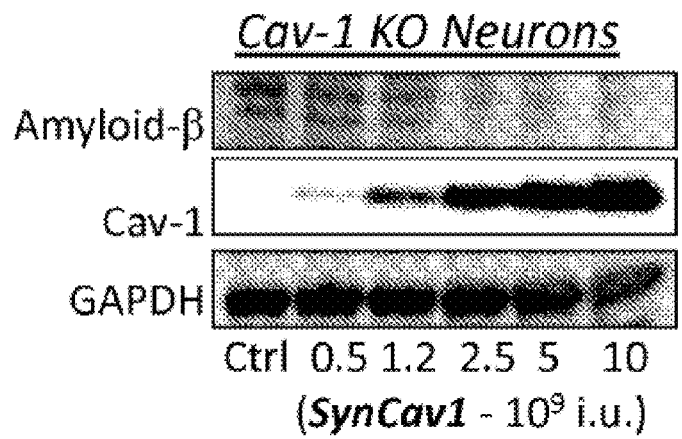
Figure 7C:
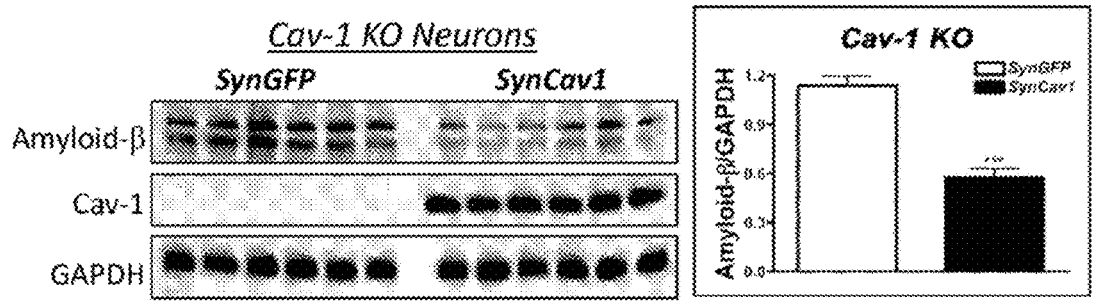

Cav-1 KO mice demonstrate pathology similar to AD such as elevated $A\beta$ production in the hippocampus. We tested whether neuron-targeted re-expression of Cav-1 in primary Cav-1 KO neurons would decrease $A\beta$ expression. We generated a viral vector that contains a neuron-specific synapsin promoter upstream of Cav-1 cDNA (SynCav1) (FIG. 7A). Increasing doses of SynCav1 for 72 hr proportionally increased Cav-1 expression and reduced $A\beta$ (FIG. 7B). Six separate neuronal cultures from Cav-1 KO mouse brains were transfected with SynGFP (control vector) or SynCav1, and SynCav1 significantly reduced $A\beta$ expression after 72 hr (FIG. 7C).

Discussion

The present study is the first to demonstrate that the cholesterol binding and MLR resident protein, Cav-1, complexes with synaptic proteins in the CNS, and that this organization is disrupted with age. Furthermore, this study is the first to demonstrate that loss of Cav-1 in a transgenic mouse model produces neuropathology similar to that exhibited with AD, i.e., $A\beta$ production, elevated astrogliosis, reduced cerebrovasculature and neuronal loss in the hippocampus. Our data suggest that not only are MLR and Cav-1 essential for maintaining and stabilizing proper synaptic signaling [27] and neuroprotection against cerebral ischemia, but they also may serve to slow the amyloidogenic process of APP seen in AD brains. Lastly, Cav-1 KO mice may serve as the first non-mutational model of AD.

It is essential to understand the basic neural mechanisms of synapse formation and stabilization in order to identify potential therapeutic targets for facilitating neuronal regeneration and recovery of neuronal networks in the aged and injured brain. Traditionally synapses and MLR are considered separate subcellular structures, yet they both contain identical physical characteristics that are essential such as cholesterol, glycosphingolipids, sphingomyelin, and other saturated fatty acid containing lipids (GM1 gangliosides, palmitic acid) as well as signaling components. [22,23,24, 25,26,27] Growing evidence supports the role for free cholesterol and MLR in neuronal synaptic formation, signaling and protection. [12,18,27,41,42,43] Because free cholesterol directly affects Cav-1 expression, factors that alter intracellular cholesterol also change Cav-1 expression

[44,45,46]. Specifically, brain derived neurotrophic factor (BDNF), a neurotrophin essential to synaptic function and development [47] which facilitates of long-term potentiation [48,49], elicits cholesterol biosynthesis and increased MLR and Cav expression in cortical and hippocampal neurons. [50] Furthermore, MLR are critical for growth cone expansion, neurite outgrowth, and axonal branching and guidance. [11,51,52] Therapeutic approaches to promote axonal regeneration and synapse formation after spinal cord injury use a MLR marker, cholera toxin B, as a direct indicator of axonal regeneration and de novo synapse formation. [53,54] Moreover, there exists increasing evidence that disruption or alterations of neuronal MLR and intracellular cholesterol can be neurotoxic and even contribute to enhanced neuronal vulnerability to AP [13,14,33], demonstrating the importance of these distinct microdomains for proper pro-survival neuronal signaling, [27,41,55,56,57] When Cav-1 was overexpressed in β-secretase expressing cells, amyloid precursor protein and β-secretase localization to MLR resulted in decreased Aβ production, suggesting a protective role by Cav-1 and MLR against AP toxicity. [30,31,32,58] Interestingly the fatty acid content in MLR (a.k.a. detergent-resistant membranes, or DRMs) isolated from synaptic endings is altered in aged animals. [59] This result is consistent with our findings that membrane fluidity in synaptosomal membranes is increased in aged brains. Age-related physiochemical changes to distinct biological membranes such as MLR could be responsible for changes in Cav-1 expression and loss of synaptosomal pro-survival signaling components with age.

Our results demonstrate that loss of Cav-1 results in accelerated aging. Cav-1 KO mice have a shortened life span. [40] Two pathophysiologies altered with aging are vulnerability to ischemic stress and progression of AD. IPC is a phenomenon whereby brief ischemia, which does not injure neurons, renders the brain less vulnerable to subsequent ischemic injury. [27,60,61,62,63,64] IPC activates endogenous signaling pathways that are neuroprotective, and this neuroprotection is lost in the aged brain. [38,39] The underlying mechanism for the lack of ischemic tolerance in the aged brain is not clear. Signaling pathways in neurons are severely compromised with age. Specifically, post-synaptic molecules such as glutamate receptors, neurotrophin receptors and pro-survival signaling cascades (i.e., kinase activation and cAMP production) decrease significantly with age. [65,66,67,68,69] It is therefore possible that the organization, and thus efficacy of signaling pathways that produce tolerance is severely limited in the aged brain. We show in young Cav-1 KO mice that preconditioning is absent, suggesting a link between the loss of MLR and disrupted organization of pro-survival signaling.

In addition to loss of IPC, Cav-1 KO mice also exhibit characteristics consistent with AD, Cerebrovascular changes and increased astrogliosis [70,71,72,73,74] could also be a contributing factor to the absence of ischemic tolerance [75] as well as the AD phenotype exhibited by young Cav-1 KO mice. Upregulation of endogenous protective signaling in aged neurons through neuron-targeted Cav-1 expression might reduce the vulnerability of the aged brain even in the presence of reduced cerebrovascular volume. Neuron-targeted Cav-1 re-expression/over-expression offers the novel possibility of re-establishing the fidelity of neuroprotective signaling that is lost with advanced age or in other forms of neurodegeneration (i.e., dementia, Alzheimer's disease, depression, Parkinson's disease).

In summary, these findings demonstrate an important role for Cav-1 and MLR in organizing synaptic pro-survival signaling components that are essential for neuroprotection against ischemic injury, neuronal regeneration, and maintaining synapse stabilization and formation. Cav-1 may be a control point for neurological aging. Further understanding of how MLR and Cav-1 serve as a nexus for pro-survival and pro-growth signaling components may not only provide potential therapeutic targets for the preservation of neuronal function, but may also yield tools that could augment the brain's capacity to reorganize its neuronal networks following injury or during late stages of neurodegenerative diseases such as AD and other forms of dementia.

References Cited in the Background and Example 1

1. Hebert L E, Scherr P A, Bienias J L, Bennett D A, Evans D A (2003) Alzheimer disease in the US population: prevalence estimates using the 2000 census. Arch Neurol 60: 1119-1122.
2. Bishop N A, Lu T, Yankner B A (2010) Neural mechanisms of ageing and cognitive decline. Nature 464: 529-535.
3. Yankner B A, Lu T, Loerch P (2008) The aging brain. Annu Rev Pathol 3: 41-66.
4. Norris C M, Halpain S, Foster T C (1998) Reversal of age-related alterations in synaptic plasticity by blockade of L-type Ca2+ channels. J Neurosci 18: 3171-3179.
5. Thibault O, Porter N M, Chen K C, Blalock E M, Kaminker P G, et al. (1998) Calcium dysregulation in neuronal aging and Alzheimer's disease: history and new directions. Cell Calcium 24: 417-433.
6. Toescu E C, Verkhratsky A, Landfield P W (2004) Ca2+ regulation and gene expression in normal brain aging. Trends Neurosci 27: 614-620.
7. Hattiangady B, Rao M S, Shetty G A, Shetty A K (2005) Brain-derived neurotrophic factor, phosphorylated cyclic AMP response element binding protein and neuropeptide Y decline as early as middle age in the dentate gyms and CA1 and CA3 subfields of the hippocampus. Exp Neurol 195: 353-371.
8. Hotulainen P, Hoogenraad C C (2010) Actin in dendritic spines: connecting dynamics to function. J Cell Biol 189: 619-629.
9. Huber A B, Kolodkin A L, Ginty D D, Cloutier J F (2003) Signaling at the growth cone: ligand-receptor complexes and the control of axon growth and guidance. Annu Rev Neurosci 26: 509-563.
10. Calabrese B, Wilson M S, Halpain S (2006) Development and regulation of dendritic spine synapses. Physiology (Bethesda) 21: 38-47.
11. Guirland C, Zheng J Q (2007) Membrane lipid rafts and their role in axon guidance. Adv Exp Med Biol 621: 144-155.
12. Mauch D H, Nagler K, Schumacher S, Goritz C, Muller E C, et al. (2001) CNS synaptogenesis promoted by glia-derived cholesterol. Science 294: 1354-1357. 13. Crameri A, Biondi E, Kuehnle K, Lutjohann D, Thelen K M, et al. (2006) The role of seladin-1/DHCR24 in cholesterol biosynthesis, APP processing and Abeta generation in vivo. Embo J 25: 432-443.
14. Bulloj A, Leal M C, Surace E I, Zhang X, Xu H, et al. (2008) Detergent resistant membrane-associated IDE in brain tissue and cultured cells: Relevance to Abeta and insulin degradation. Mol Neurodegener 3: 22.
15. Cecchi C, Rosati F, Pensalfini A, Formigli L, Nosi D, et al. (2008) Seladin-1/DHCR24 protects neuroblastoma cells against Abeta toxicity by increasing membrane cholesterol content. J Cell Mol Med 12: 1990-2002.

16. Peri A, Serio M (2008) Neuroprotective effects of the Alzheimer's disease-related gene seladin-1. J Mol Endocrinol 41: 251-261.
17. Vanmierlo T, Bloks V W, van Vark-van der Zee L C, Rutten K, Kerksiek A, et al. (2009) Alterations in Brain Cholesterol Metabolism in the APPSLxPS1mut mouse, a Model for Alzheimer's Disease. J Alzheimers Dis.
18. Willmann R, Pun S, Stallmach L, Sadasivam G, Santos A F, et al. (2006) Cholesterol and lipid microdomains stabilize the postsynapse at the neuromuscular junction. Embo J 25: 4050-4060.
19. Smart E J, Graf G A, McNiven M A, Sessa W C, Engelman J A, et al. (1999) Caveolins, liquid-ordered domains, and signal transduction. Mol Cell Biol 19: 7289-7304.
20. Lisanti M P, Scherer P E, Vidugiriene J, Tang Z, Hermanowski-Vosatka A, et al. (1994) Characterization of caveolin-rich membrane domains isolated from an endothelial-rich source: implications for human disease. J Cell Biol 126: 111-126.
21. Lisanti M P, Scherer P E, Tang Z, Sargiacomo M (1994) Caveoiae, caveolin and caveolin-rich membrane domains: a signalling hypothesis. Trends Cell Biol 4: 231-235.
22. Bilderback T R, Gazula V R, Lisanti M P, Dobrowsky R T (1999) Caveolin interacts with Trk A and p75(NTR) and regulates neurotrophin signaling pathways. J Biol Chem 274: 257-263.
23. Suzuki S, Numakawa T, Shimazu K, Koshimizu H, Hara T, et al. (2004) BDNF-induced recruitment of TrkB receptor into neuronal lipid rafts: roles in synaptic modulation. J Cell Biol 167: 1205-1215.
24. Besshoh S, Bawa D, Teves L, Wallace M C, Gurd J W (2005) Increased phosphorylation and redistribution of NMDA receptors between synaptic lipid rafts and post-synaptic densities following transient global ischemia in the rat brain. J Neurochem 93: 186-194.
25. Gaudreault S B, Blain J F, Gratton J P, Poirier J (2005) A role for caveolin-1 in post-injury reactive neuronal plasticity. J Neurochem 92: 831-839.
26. Hibbert A P, Kramer B M, Miller F D, Kaplan D R (2006) The localization, trafficking and retrograde transport of BDNF bound to p75NTR in sympathetic neurons. Mol Cell Neurosci 32: 387-402.
27. Head B P, Patel H H, Tsutsumi Y M, Hu Y, Mejia T, et al. (2008) Caveolin-1 expression is essential for N-methyl-D-aspartate receptor-mediated Src and extracellular signal-regulated kinase ½ activation and protection of primary neurons from ischemic cell death. Faseb J 22: 828-840.
28. Denny J B (2006) Molecular Mechanisms, Biological Actions, and Neuropharmacology of the Growth-Associated Protein GAP-43. Curr Neuropharmacol 4: 293-304.
29. Bertram L, Tanzi R E (2008) Thirty years of Alzheimer's disease genetics: the implications of systematic meta-analyses. Nat Rev Neurosci 9: 768-778.
30. Hattori C, Asai M, Onishi H, Sasagawa N, Hashimoto Y, et al. (2006) BACE1 interacts with lipid raft proteins. J Neurosci Res 84: 912-917.
31. Yoon I S, Chen E, Busse T, Repetto E, Lakshmana M K, et al. (2007) Low-density lipoprotein receptor-related protein promotes amyloid precursor protein trafficking to lipid rafts in the endocytic pathway. Faseb J 21: 2742-2752.
32. Harris B, Pereira I, Parkin E (2009) Targeting AD AM10 to lipid rafts in neuroblastoma SH-SY5Y cells impairs amyloidogenic processing of the amyloid precursor protein. Brain Res 1296: 203-215.
33. Stefani M, Liguri G (2009) Cholesterol in Alzheimer's disease: unresolved questions. Curr Alzheimer Res 6: 15-29.
34. Trushina E, Du Charme J, Parisi J, McMurray C T (2006) Neurological abnormalities in caveolin-1 knock out mice. Behav Brain Res 172: 24-32.
35. Gioiosa L, Raggi C, Ricceri L, Jasmin J F, Frank P G, et al. (2008) Altered emotionality, spatial memory and cholinergic function in caveolin-1 knock-out mice. Behav Brain Res 188: 255-262.
36. Jasmin J F, Malhotra S, Singh Dhallu M, Mercier I, Rosenbaum D M, et al. (2007) Caveolin-1 deficiency increases cerebral ischemic injury. Circ Res 100: 721-729.
37. Lingwood D, Simons K (2010) Lipid rafts as a membrane-organizing principle. Science 327: 46-50.
38. Kerr D S, Razak A, Crawford N (2002) Age-related changes in tolerance to the marine algal excitotoxin domoic acid. Neuropharmacology 43: 357-366.
39. Schaller B J (2007) Influence of age on stroke and preconditioning-induced ischemic tolerance in the brain. Exp Neurol 205: 9-19.
40. Park D S, Cohen A W, Frank P G, Razani B, Lee H, et al. (2003) Caveolin-1 null (−/−) mice show dramatic reductions in life span. Biochemistry 42: 15124-15131.
41. Hering H, Lin C C, Sheng M (2003) Lipid rafts in the maintenance of synapses, dendritic spines, and surface AMPA receptor stability. J Neurosci 23: 3262-3271.
42. Samhan-Arias A K, Garcia-Bereguiain M A, Martin-Romero F J, Gutierrez-Merino C (2009) Clustering of plasma membrane-bound cytochrome b5 reductase within 'lipid raft' microdomains of the neuronal plasma membrane. Mol Cell Neurosci 40: 14-26.
43. Renner M, Choquet D, Triller A (2009) Control of the postsynaptic membrane viscosity. J Neurosci 29: 2926-2937.
44. Bist A, Fielding P E, Fielding C J (1997) Two sterol regulatory element-like sequences mediate up-regulation of caveolin gene transcription in response to low density lipoprotein free cholesterol. Proc Natl Acad Sci USA 94: 10693-10698.
45. Bist A, Fielding C J, Fielding P E (2000) p53 regulates caveolin gene transcription, cell cholesterol, and growth by a novel mechanism. Biochemistry 39: 1966-1972.
46. Francesconi A, Kumari R, Zukin R S (2009) Regulation of group I metabotropic glutamate receptor trafficking and signaling by the caveolar/lipid raft pathway. J Neurosci 29: 3590-3602.
47. Poo M M (2001) Neurotrophins as synaptic modulators. Nat Rev Neurosci 2: 24-32.
48. Figurov A, Pozzo-Miller L D, Olafsson P, Wang T, Lu B (1996) Regulation of synaptic responses to high-frequency stimulation and LTP by neurotrophins in the hippocampus. Nature 381: 706-709.
49. Patterson S L, Abel T, Deuel T A, Martin K C, Rose J C, et al. (1996) Recombinant BDNF rescues deficits in basal synaptic transmission and hippocampal LTP in BDNF knockout mice. Neuron 16: 1137-1145.
50. Suzuki S, Kiyosue K, Hazama S, Ogura A, Kashihara M, et al. (2007) Brain-derived neurotrophic factor regulates cholesterol metabolism for synapse development. J Neurosci 27: 6417-6427.
51. Grider M H, Park D, Spencer D M, Shine H D (2009) Lipid raft-targeted Akt promotes axonal branching and growth cone expansion via mTOR and Racl, respectively. J Neurosci Res.

52. Zhao H, Cao X, Wu G, Loh H H, Law P Y (2009) Neurite Outgrowth is Dependent on the Association of c-Src and Lipid Rafts. Neurochem Res.
53. Alto L T, Havton L A, Conner J M, Hollis Ii E R, Blesch A, et al. (2009) Chemotropic guidance facilitates axonal regeneration and synapse formation after spinal cord injury. Nat Neurosci 12: 1106-1113.
54. Lee H, McKeon R J, Bellamkonda R V (2010) Sustained delivery of thermostabilized chABC enhances axonal sprouting and functional recovery after spinal cord injury. ProcNatl Acad Sci USA 107: 3340-3345.
55. Kumar B, Andreatta C, Koustas W T, Cole W C, Edwards-Prasad J, et al. (2002) Mevastatin induces degeneration and decreases viability of cAMP-induced differentiated neuroblastoma cells in culture by inhibiting proteasome activity, and mevalonic acid lactone prevents these effects. J Neurosci Res 68: 627-635.
56. Cerezo-Guisado M I, Garcia-Roman N, Garcia-Marin L J, Alvarez-Barrientos A, Bragado M J, et al. (2007) Lovastatin inhibits the extracellular-signal-regulated kinase pathway in immortalized rat brain neuroblasts. Biochem J 401: 175-183.
57. Kannan M, Steinert J R, Forsythe I D, Smith A G, Chernova T (2008) Mevastatin accelerates loss of synaptic proteins and neurits degeneration in aging cortical neurons in a heme-independent manner. Neurobiol Aging.
58. Ferrer I (2009) Altered mitochondria, energy metabolism, voltage-dependent anion channel, and lipid rafts converge to exhaust neurons in Alzheimer's disease. J Bioenerg Biomembr.
59. Mateos M V, Salvador G A, Giusto N M (2009) Selective localization of phosphatidylcholine-derived signaling in detergent-resistant membranes from synaptic endings. Biochim Biophys Acta.
60. Murry C E, Jennings R B, Reimer K A (1986) Preconditioning with ischemia: a delay of lethal cell injury in ischemic myocardium. Circulation 74: 1124-1136.
61. Heurteaux C, Lauritzen I, Widmann C, Lazdunski M (1995) Essential role of adenosine, adenosine A1 receptors, and ATP-sensitive K+ channels in cerebral ischemic preconditioning. ProcNatl Acad Sci USA 92: 4666-4670.
62. Gidday J M, Shall A R, Maceren R G, Wang Q, Pelligrino D A, et al. (1999) Nitric oxide mediates cerebral ischemic tolerance in a neonatal rat model of hypoxic preconditioning. J Cereb Blood Flow Metab 19: 331-340.
63. Rubino A, Yellon DM (2000) Ischaemic preconditioning of the vasculature: an overlooked phenomenon for protecting the heart? Trends Pharmacol Sci 21 : 225-230.
64. Nishio S, Yunold M, Chen Z F, Anzivino M J, Lee I C S (2000) Ischemic tolerance in the rat neocortex following hypothermic preconditioning. J Neurosurg 93: 845-851.
65. Gonzales R A, Brown L M, Jones T W, Trent R D, Westbrook S L, et al. (1991) N-methyl-D-aspartate mediated responses decrease with age in Fischer 344 rat brain. Neurobiol Aging 12: 219-225.
66. Tamaru M, Yoneda Y, Ogita K, Shimizu J, Nagata Y (1991) Age-related decreases of the N-methyl-D-aspartate receptor complex in the rat cerebral cortex and hippocampus. Brain Res 542: 83-90.
67. Cai D, Qiu J, Cao Z, McAtee M, Bregman B S, et al. (2001) Neuronal cyclic AMP controls the developmental loss in ability of axons to regenerate. J Neurosci 21: 4731-4739.
68. Magnusson K R, Nelson S E, Young A B (2002) Age-related changes in the protein expression of subunits of the NMD A receptor. Brain Res Mol Brain Res 99: 40-45.
69. Monti B, Virgili M, Contestabile A (2004) Alterations of markers related to synaptic function in aging rat brain, in normal conditions or under conditions of long-term dietary manipulation. Neurochem Int 44: 579-584.
70. Bourasset F, Melissa O, Tremblay C, Mien C, Do T M, et al. (2009) Reduction of the cerebrovascular volume in a transgenic mouse model of Alzheimer's disease. Neuropharmacology 56: 808-813.
71. Zhu M, Gu F, Shi J, Hu J, Hu Y, et al. (2008) Increased oxidative stress and astrogliosis responses in conditional double-knockout mice of Alzheimer-like presenilin-1 and presenilin-2. Free Radic Biol Med 45: 1493-1499.
72. Gama Sosa M A, Gasperi R D, Rocher A B, Wang A C, Janssen W G, et al. (2010) Age-related vascular pathology in transgenic mice expressing presenilin 1-associated familial Alzheimer's disease mutations. Am J Pathol 176: 353-368.
73. Dickstein D L, Walsh J, Brautigam H, Stockton S D, Jr., Gandy S. et al. (2010) Role of vascular risk factors and vascular dysfunction in Alzheimer's disease. Mt Sinai J Med 77: 82-102.
74. Elder G A, Gama Sosa M A, De Gasperi R, Dickstein D L, Hof P R (2010) Presenilin transgenic mice as models of Alzheimer's disease. Brain Struct Funct 214: 127-143.
75. Shapira S, Sapir M, Wengier A, Grauer E, Kadar T (2002) Aging has a complex effect on a rat model of ischemic stroke. Brain Res 925: 148-158.
76. Gabbita S P, Butterfield D A, Hensley K, Shaw W, Carney J M (1997) Aging and caloric restriction affect mitochondrial respiration and lipid membrane status: an electron paramagnetic resonance investigation. Free Radio Biol Med 23: 191-201.
77. Gabbita S P, Subramaniam R, Allouch F, Carney J M, Butterfield D A (1998) Effects of mitochondrial respiratory stimulation on membrane lipids and proteins: an electron paramagnetic resonance investigation. Biochim Biophys Acta 1372: 163-173.
78. Behrens M M, Ali S S, Dao D N, Lucero J, Shekhtman G, et al. (2007) Ketamine-induced loss of phenotype of fast-spiking interneurons is mediated by NADPH-oxidase. Science 318: 1645-1647.
79. Bamji S X, Shimazu K, Kimes N, Huelsken J, Birchmeier W, et al. (2003) Role of beta-catenin in synaptic vesicle localization and presynaptic assembly. Neuron 40: 719-731.
80. Bouwman J, Maia A S, Camoletto P G, Posthuma G, Roubos E W, et al. (2004) Quantification of synapse formation and maintenance in vivo in the absence of synaptic release. Neuroscience 126: 115-126.
81. Elia L P, Yamamoto M, Zang K, Reichardt L F (2006) p120 catenin regulates dendritic spine and synapse development through Rho-family GTPases and cadherins. Neuron 51: 43-56.
82. Head B P, Patel H H, Niesman I R, Drummond J C, Roth D M, et al. (2009) Inhibition of p75 neurotrophin receptor attenuates isoflurane-mediated neuronal apoptosis in the neonatal central nervous system. Anesthesiology 110: 813-825.
83. Yam P Y, Li S, Wu J, Hu J, Zaia J A, et al. (2002) Design of HIV vectors for efficient gene delivery into human hematopoietic cells. Mol Ther 5: 479-484.

Example 2

Chemicals and Antibodies

Antibodies used for immunoblot, immunoprecipitation and immunofluorescence were the following: Cav-1 (Santa Cruz Biotech—Santa Cruz, Calif.; Cell Signaling—San Diego, Calif.; and Abcam—Cambridge, Mass.), PSD-95 (Abcam and Affinity Bioreagents—Rockford, Ill.), NMDAR2A, NMDAR2B, AMPAR (Abcam). TrkBR (Cell Signaling),®3-tubulin (Abcam), phospho-ERK1/2 (Neuromics—Edina, Minn.) and total ERK1/2 (Stressgen, city), phospho and total Src (Cell Signaling), GAPDH (Imgenex, San Diego, Calif.), Aβ/A4 protein (Santa Cruz Biotech and Millipore—Billecira, Mass.), P-Tau (Thermo Scientific—Hanover Park, Ill.), Nissl stain (Molecular Probes/Invitrogen, Carlsbad, Calif.), cholera toxin B (CT-B, Molecular Probes/Invitrogen), GSA (Molecular Probes/Invitrogen), GFAP (Abcam), and Toludine blue (Sigma-Aldrich—St. Louis, Mo.). Flouro-Jade®B was obtained from Millipore. Primary antibodies were visualized using secondary antibodies conjugated to horseradish peroxidase (Santa Cruz Biotech) and ECL reagent (Amersham Pharmacia Biotech, Piscataway, N.J.). All displayed bands were compared to molecular weight standards (Santa Cruz Biotech). The amount of protein per sample was determined using a dye-binding protein assay (Bio-Rad, Hercules, Pa.). For immunoprecipitation protein A- or protein G-agarose were obtained from Pierce (Rockford, Ill.). For immunofluorescence, FITC and Texas Red secondary antibodies were obtained from Molecular Probes (Carlsbad, Calif.).

Immunofluorescence Confocal Microscopy

Tissue and cells were fixed with 4% paraformaldehyde in phosphate-buffered saline (PBS) for 10 min at room temperature, incubated with 100 mM glycine (pH. 7.4) for 10 min to quench aldehyde groups, permeabilized in buffered Triton X-100 (0.1%) for 10 min, blocked with 1% BSA/PBS/Tween (0.05%) for 20 min and then incubated with primary antibodies (1:100) in 1% BSA/PBS/Tween (0.05%) for 24-48 h at 4° C. Excess antibody were removed by incubation with PBS/Tween (0.1%) for 15 min and incubated with FITC or Alexa-conjugated secondary antibody (1:250) for 1 h. To remove excess secondary antibody, cells were washed 6× at 5 min intervals with PBS/Tween (0.1%) and incubated for 20 min with the nuclear stain Dapi (1:5000) diluted in PBS. Cells were washed for 10 min with PBS and mounted in gelvatol for microscopic imaging. Confocal images were obtained and captured with a confocal microscope (Olympus FV1000, Zeiss LSM 510 META) at 20, 40, or 60× magnification and digitized stacks of 1-μm-thick optical sections. Exposure times were set such that the camera response is in the linear range for each fluorophore. The data sets were analyzed using SoftWorx software (Applied Precision, Inc) on a Silicon Graphics Octane workstation. Image analysis were performed with Data Inspector program in SoftWorx. Maximal projection volume views or single optical sections are shown as indicated. Colocalization of pixels was assessed quantitatively by CoLocalizer Pro 1.0 software (http://www.homepage.mac.com/colocalizerpro/). Overlap coefficient according to Manders was used to determine the degree of colocalization on whole cells or membrane regions of interest after subtracting background through normalized threshold values. The values were defined as 0 to 1 with 1, implying that 100% of both components overlap with the other part of the image. Statistical analysis will be performed using Prism.

Histological Preparation

For tissue fixation, under deep pentobarbital anesthesia, a midline thoracotomy was performed and the descending thoracic aorta was occluded. A 20 gauge needle was inserted into the left ventricle and the animal was perfused transcardially with 20 ml of heparinized saline followed by 20 ml of 4% buffered formalin. The right atrium was incised to permit free flow of perfusion fluid. The brain was removed and post-fixed for 24-48 h in fixative. The brain was sectioned into 4 mm blocks, placed in tissue holders and dehydrated in graded concentrations of ethanol in a tissue processor (Autotechnicon, Technicon Instruments, Tarrytown, N.Y.). The tissue holders were then transferred into a paraffin bath in an oven at 37° C. under vacuum suction. The paraffin blocks were separated from tissue holders and mounted in a Histostat 820 S microtome (Reichert Scientific Instruments, Depew, N.Y.). 5-10 μm sections were then cut, placed on glass slides and incubated overnight at 37° C. The tissue sections were then prepared for immunohistochemistry. For cerebrovascular volume histological analysis, cryostat sections (50 μm) of mouse hippocampus were stained with lectin GSA (*Griffonia simplicafolia*) to label blood vessels. 8-10 low magnification images were taken on Zeiss Axiophot taking matched images. Vessels were traced with Photoshop and area of fluorescence was determined using Colocalizer Pro software.

Immunoprecipitation and Immunoblot Analysis

Immunoprecipitations (IPs) were performed using either protein A- or protein G-agarose (Pierce). Antibodies used for IPs were caveolin-1 (Cell Signaling) and PSD95 (Affinity Bioreagents or Abcam). Lysates were incubated with primary antibody for 1-3 h at 4° C., immunoprecipitated with protein-agarose overnight at 4° C. and then centrifuged at 13,000 g for 5 min. Protein-agarose pellets were washed once in lysis buffer (50 mM Tris-HCl, pH 7.5, 500 mM NaCl, 1% Igepal CA-630, 1% deoxycholic acid, 0.2% sodium dodecyl sulfate) followed by subsequent washes in wash buffer 2 (50 mM Tris-HCl, pH 7.5, 500 mM NaCl, 0.2% Igepal CA-630) and wash buffer 3 (10 mM Tris-HCl, pH 7.5, 0.2% Igepal CA-630). Proteins in fractions, immunoprecipitates, and cell lysates were separated by SDS-polyacrylamide gel electrophoresis using 10% or 4-12% acrylamide gels (Invitrogen) and transferred to polyvinylidene difluoride membranes (Millipore) by electroelution. Membranes were blocked in 20 mM PBS Tween (1%) containing 3% bovine serum albumin (BSA) and incubated with primary antibodies overnight at 4° C. Primary antibodies were visualized using secondary antibodies conjugated to horseradish peroxidase (Santa Cruz Biotech) and ECL reagent (Amersham Pharmacia Biotech, Piscataway, N.J.). All displayed bands were compared to molecular weight standards (Santa Cruz Biotech). The amount of protein per fraction were determined using a dye-binding protein assay (Bio-Rad, Hercules, Pa.).

Production of Lentivirus Vectors

Lentivirus vectors were produced by transient co-transfection of HEK293T cells maintained in Dulbecco's modified Eagle's medium (DMEM) with 10% FCS. HEK293T cells in 150 mm dishes were co-transfected by the Polyethylenimine (PEI) method with each HIV1 vector plasmid, pLP1 (pGag-Pol), pLP2 (pRev) (Invitrogen), and pCMV-G. Conditioned medium at day 1, 2, and 3 post transfection was collected, filtered through a 0.45 μm filter, and concentrated by centrifugation at 7000 rpm for 16 hrs at 4° C. with a Sorvall GS-3 rotor. The resulting pellets were re-suspended with buffer containing 10 mM Tris HCl, pH 7.8, 1 mM MgCl2 and 3% sucrose.

Titering of HIV1 Vectors by Real-Time Q-PCR

HIV1-CMV-GFP vector ($1\times10^9$ iu/ml) was used as the standard. HEK293 cells in a 6-well plate were infected with different amounts of viruses in the presence of polybrene (4 ug/ml). Infected cells were passaged once every 4 days and cell DNAs were prepared at day 14 post infection by the DNeasy Blood & Tissue kit (Qiagen Science, MD). Real-time Q-PCR was performed using a primer set selected from the WPRE sequence contained in the HIV1 vector backbone.

References Cited in Example 2

1. Zinchuk, O., Fukushima, A. & Hangstefer, E. Dynamics of PAF-induced conjunctivitis reveals differential expression of PAF receptor by macrophages and eosinophils in the rat. Cell Tissue Res 317, 265-277 (2004),
2. Yee, J. K., Friedmann, T. & Burns, J. C. Generation of high-titer pseudotyped retroviral vectors with very broad host range. Methods Cell Biol 43 Pt A, 99-112 (1994).
3. Yee, J. K., et al. A general method for the generation of high-titer, pantropic retroviral vectors: highly efficient infection of primary hepatocytes. Proc Natl Acad Sci USA 91, 9564-9568 (1994).

Example 3

Materials and Methods

All studies performed on animals were approved by Veteran Affairs San Diego Institutional Animal Care and Use Committee and conform to relevant National Institutes of Health guidelines.

Chemicals and Antibodies—

Antibodies used for immunoblot, immunoprecipitation and immunofluorescence were the following: caveolin-1 (Santa Cruz Biotech—Santa Cruz, Calif.; Cell Signaling—San Diego, Calif.; and Abcam—Cambridge, Mass.), post-synaptic density 95 (PSD95, Abcam and Affinity Bioreagents—Rockford, Ill.), N-methyl-D-aspartate receptors (NMDAR2A and NMDAR2B, Abcam), α-amino-3-hydroxy-5-methyl-4-isoxazolepropionic acid receptor (AMPAR, Abcam), neurotrophic tyrosine kinase, receptor, type 2 (TrkBR, Cell Signaling), b3-tubulin (Abcam) and microtubule-associated protein 2 (MAP2, Abcam), phospho-ERK1/2 (Neuromics—Edina, Minn.) and total ERK1/2 (Stressgen, city), phospho and total Src (Cell Signaling), Ca2+/calmodulin-dependent protein kinases II (P-CaMKII, Cell Signaling), GAPDH (Imgenex, San Diego, Calif.), cholera toxin B (CT-B, Molecular Probes/Invitrogen). Primary antibodies were visualized using secondary antibodies conjugated to horseradish peroxidase (Santa Cruz Biotech) and ECL reagent (Amersham Pharmacia Biotech, Piscataway, N.J.). All displayed bands were compared to molecular weight standards (Santa Cruz Biotech). The amount of protein per sample was determined using a dye-binding protein assay (Bio-Rad, Hercules, Pa.). For immunofluorescence, FITC and Texas Red secondary antibodies were obtained from Molecular Probes (Carlsbad, Calif.). All agonists were purchased commercially: brain derived neurotrophic factor (BDNF, 50 ng/ml, Invitrogen), NMD A (10 µM, Calbiochem), dopamine 1 receptor agonist (10 µM, SKF 81297 hydrobromide, Tocris), 5-hydroxytryptophan receptor 6 (10 µM, EMD 386088 hydrobromide, Tocris), forskolin (10 µM, F6886, Sigma-Aldrich), methyl-P-cyclodextrin (MβCD, 3 mM, C4555, Sigma-Aldrich), cholesterol (50 µg/ml, C4951, Sigma-Aldrich). The phosphodiesterase 4 (PDE4) inhibitor rolipram was purchased from Sigma-Aldrich (10 µM, R6520).

Isolation and Culture of Primary Neurons—

Primary neurons were isolated from the brains (cortex and hippocampus) of postnatal day 1-3 C57BL/6J wild type and Cav-1-/- mice using the papain dissociation system from Worthington Biochemical (Lakewood, N.J.) as previously described (9,27). Neurons were cultured in Neuobasal A media supplemented with B27 (2%), 250 mM GLUTMax1, and penicillin/streptomycin (1%) and grown on poly-D-lysine/laminin (2 µg/cm2) coated plates at 37° C. in 5% CO2 for days as indicated. Anti-mitotic agents (cytosine arabinoside or FUDR) was added for the first 3 days following isolation to prevent non-neuronal cells from proliferating. Assessment with neuronal markers revealed that >90% of the cells are neurons. After 3 days, the antimitotic agents were removed to reduce neuronal toxicity associated with these agents. Because neuronal cell death occurs during culture, we added basic fibroblast growth factor (bFGF) or platelet-derived growth factor, (PDGF for mice) to maintain neuronal viability and plasticity.

Adenovirus Expressing Short Hairpin Small Interference RNA for Caveolin-1 (AdvshRNACav1)—

The expression of caveolin-1 in primary neurons was suppressed by using an adenoviral vector encoding a short hairpin loop for small interfering RNA to Cav-1. The sequences of caveolin-1 siRNA that are generated intracellularly are as follows, sense: GGAAAUUGAUCUGGU-CAACtt (SEQ ID NO:3), antisense: GUUGACCAGAU-CAAUUUCCtt (SEQ ID NO:4). Cells were treated with varying doses of the vector ($6 \times 10^7$ pfu/µl) for 72 hr. Functional knockdown of protein expression was assessed by immunoblot and immunofluorescence microscopy.

cAMP Radioimmunoassay (RIA)—

We assayed cAMP accumulation by incubating cells for 30 min with the PDE4 inhibitor rolipram (10 µM) followed by GPCR agonists for 15 min. To terminate the reaction, assay medium was aspirated, and 250 µl of ice-cold trichloroacetic acid (TCA 7.5%, w/v) was added. cAMP content in TCA extracts was determined by radioimmunoassay (28, 29). Production of cAMP was normalized to the amount of protein (determined using a dye-binding protein assay [Bio-Rad, Hercules, Pa.] per sample.

Biochemical Characterization of Membrane/Lipid Rafts—

Sucrose density fractionation was performed on primary neurons as previously described (9). Neurons were lysed in 500 mM Na2CO3, pH 11.0, to extract peripheral membrane proteins. Cells were homogenized using three 10-s bursts of a tissue grinder and then sonicated with 3 cycles of 20-s bursts of sonication and a 1-min incubation on ice. Approximately 1 ml of homogenate (2 mg for both SynGFP and SynCav1 samples) were mixed with 1 ml of 90% sucrose in 25 mM MES, 150 mM NaCl (MBS, pH 6.5) to form 45% sucrose and loaded at the bottom of an ultracentrifuge tube. A discontinuous sucrose gradient was generated by layering 6 ml of 35% sucrose prepared in MBS (250 mM Na2CO3) followed by 4 ml of 5% sucrose (in MBS/Na2CO3). Gradients were centrifuged at 280,000×g using a SW41Ti rotor (Beckman) for 4 h at 4° C. Samples were removed in 1-ml aliquots to form 12 fractions.

Because membrane/lipid rafts are concentrated at the 5/35% interface (fractions 4 & 5), only fractions 4-12 were prepared for cholesterol analysis and immunoblot. Quantification of cholesterol was performed using Amplex® Red Cholesterol Assay (Invitrogen cat. A 12216). Approximately 50 µl of normalized samples, in triplicate, were placed in 96 well TC clear flat bottom plates (Corning #3997), where 50 µl of working solution containing Amplex Red was added as per directions. Plates were incubated at 37° C. and were protected from light. Plates were then placed into Infinite m200 PRO (Tecan) plate reader and were read at 571 nm and 585 nm for absorption and fluorescence emission, respectively. Data were placed on a standard curve using known amounts of cholesterol controls for analysis.

Immunoblot Analysis—

Samples were separated by SDS-polyacrylamide gel electrophoresis using 10% or 4-12% acrylamide gels (Invitrogen) and transferred to polyvinylidene difluoride membranes (Millipore) by electroelution. Membranes were blocked in 20 mM PBS Tween (1%) containing 3% bovine serum albumin (BSA) and incubated with primary antibodies overnight at 4° C. Primary antibodies were visualized using secondary antibodies conjugated to horseradish peroxidase (Santa Cruz Biotech) and ECL reagent (Amersham Pharmacia Biotech, Piscataway, N.J.). Bands were compared to molecular weight standards (Santa Cruz Biotech). The amount of protein per fraction were determined using a dye-binding protein assay (Bio-Rad).

Generation of SynCav1 Construct—

To link the neuron-specific synapsin (Syn) promoter with the Cav-1 cDNA, an XbaI-SalI DNA fragment containing the Syn promoter was inserted into the NheI-SalI sites of pEGFP-N1 (Clontech); the resulting plasmid was designated pSyn-EGFP. A 685 bp Cav-1 cDNA was isolated from the pCRII-TOPO vector (Invitrogen) by digestion with PmeI-NotI and inserted into the SmaI-NotI site of the pSyn-EGFP to generate pSyn-Cav-1, in which the EGFP gene was replaced with Cav-1 cDNA. The Syn-promoter-Cav-1 cassette was isolated from p Syn-Cav-1 and inserted into the BamHI site of the HIV1 vector backbone plasmid pHIV7 (30); the resulting plasmid was designated pHIV1-Syn-Cav-1. Lentivirus vectors were produced by transient co-transfection of HEK293T cells maintained in Dulbecco's modified Eagle's medium (DMEM) with 10% FCS. HEK293T cells in 150 mm dishes were co-transfected by the Polyethylenimine (PEI) method with each HIV1 vector plasmid, pLP1 (pGag-Pol), pLP2 (pRev) (Invitrogen), and pCMV-G (31). Conditioned medium was collected at days 1, 2, and 3 post transfection, filtered through a 0.45 μm filter, and concentrated by centrifugation at 7000 rpm for 16 hr at 4° C. in a Sorvall GS-3 rotor. The resulting pellets were re-suspended in buffer containing 10 mM Tris HCl, pH 7.8, 1 mM MgCl2 and 3% sucrose. HIV1-CMV-GFP vector ($1\times10^9$ iu/ml) was used as the standard. HEK293 cells in a 6-well plate were incubated with different titers of viruses in the presence of polybrene (4 μg/ml). Infected cells were passaged every 4 d and their DNA was prepared at day 14 post-infection using the DNeasy Blood & Tissue kit (Qiagen Science, MD). Real-time Q-PCR was performed using a primer set selected from the WPRE sequence contained in the HIV1 vector backbone.

Immunofluorescence Confocal Microscopy—

Primary neurons were fixed with 4% paraformaldehyde in phosphate-buffered saline (PBS) for 10 min at room temperature, incubated with 100 mM glycine (pH. 7.4) for 10 min to quench aldehyde groups, permeabilized in buffered Triton X-100 (0.1%) for 10 min, blocked with 1% BSA/PBS/Tween (0.05%) for 20 min and then incubated with primary antibodies in 1% BSA/PBS/Tween (0.05%) for 24-48 h at 4° C. Excess antibody was removed by washing with PBS/Tween (0.1%) for 15 min followed by incubation with FITC or Alexa-conjugated secondary antibody (1:250) for 1 h. To remove excess secondary antibody, tissue or cells were washed 6× at 5 min intervals with PBS/Tween (0.1%) and incubated for 20 min with the nuclear stain Dapi (1:5000) diluted in PBS. Cells were washed for 10 min with PBS and mounted in gelvatol for microscopic imaging, Confocal images were captured with an Olympus confocal microscope system (Applied Precision, Inc., Issaquah, Wash.) that included a Photometries CCD mounted on a Nikon TE-200 inverted epi-fluorescence microscope. Between 30 and 80 optical sections spaced by ~0.1-0.3 μm were captured. Exposure times were set such that the camera response was in the linear range for each fluorophore. Data sets were analyzed using FluoroView. Quantitation of dendritic branching, length, area, and volume was performed using Autoneuron, which measures 3D image volume stacks (MBF Bioscience). Statistical analysis was performed using Prism. All parametric data were analyzed by unpaired t-tests or ANOVA Bonferroni's Multiple Comparison as appropriate; post-hoc comparisons were made by Student Neuman Keuls tests. Significance was set at $p<0.05$. Statistical analysis was performed using Prism 4 (GraphPad Software, Inc., La Jolla, Calif.).

Results

Neuron-Targeted Over-Expression of Cav-J Enhances Expression of Pro-Survival Signaling Components and Augments Signaling in Primary Neurons.

Figure 11A:
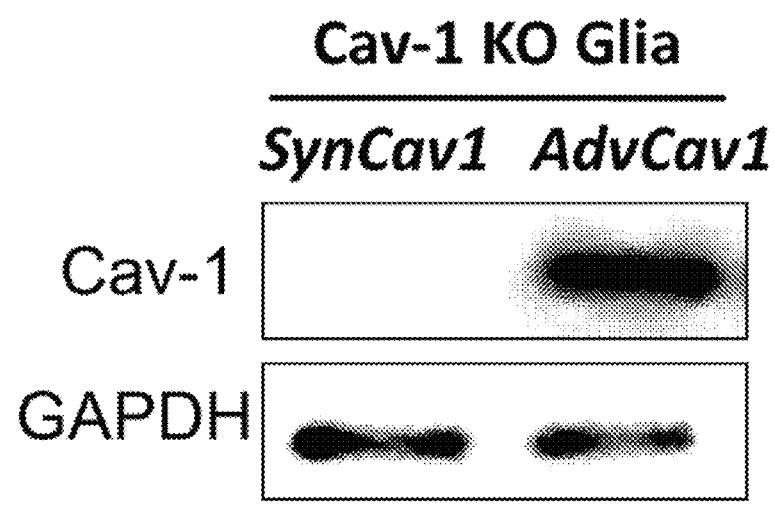
Figure 11B:
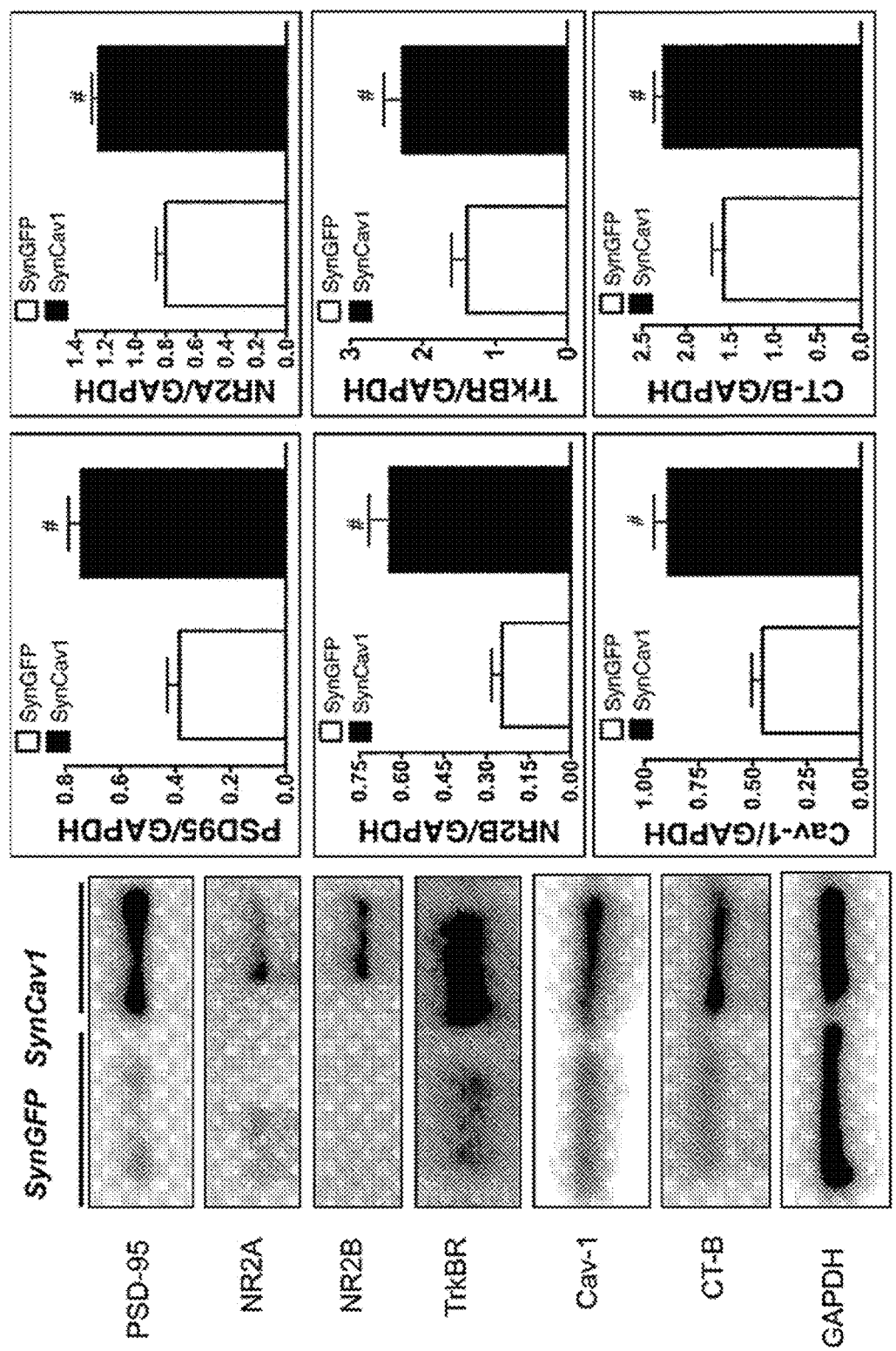
Figure 11C:
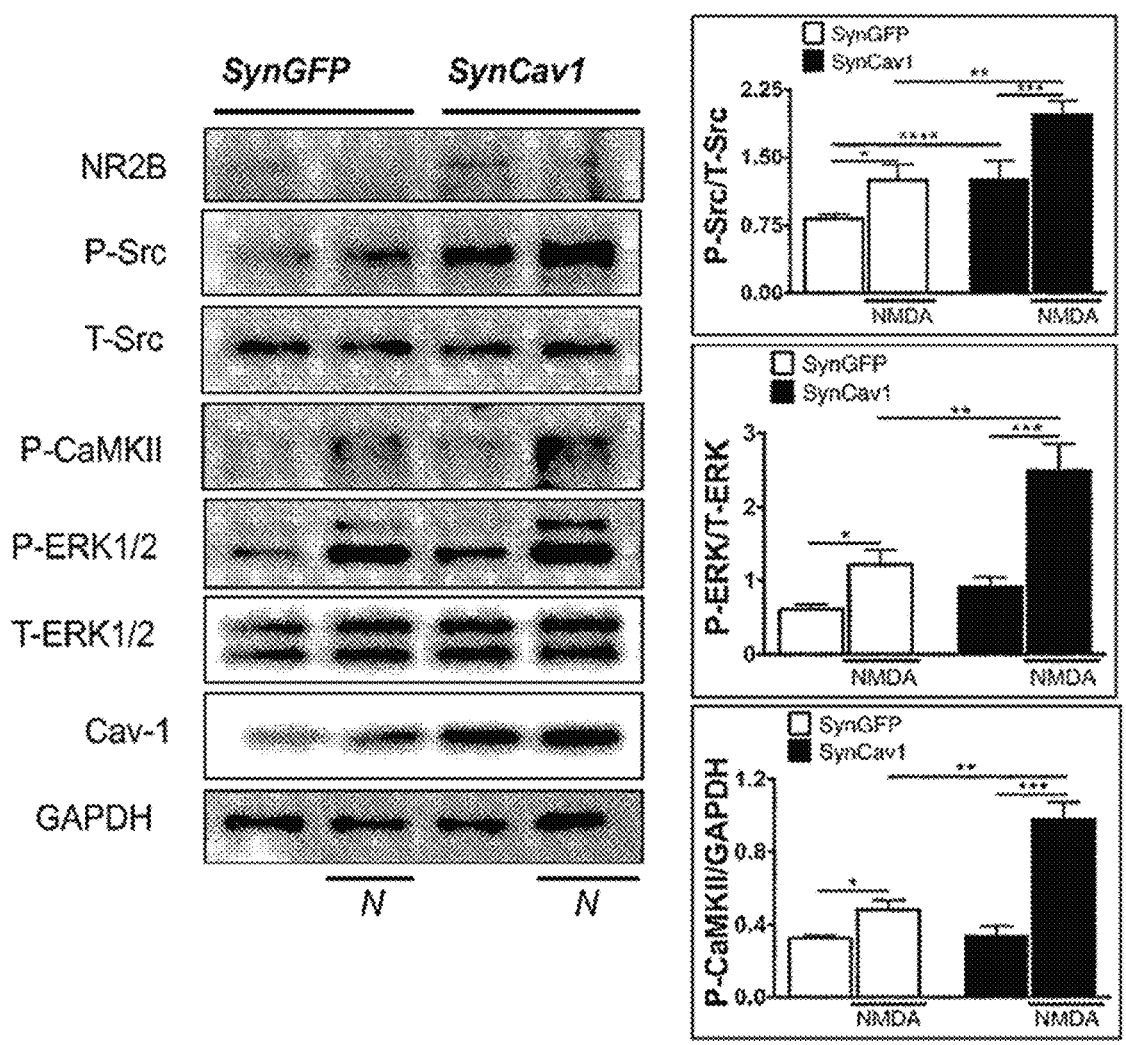
Figure 11D:
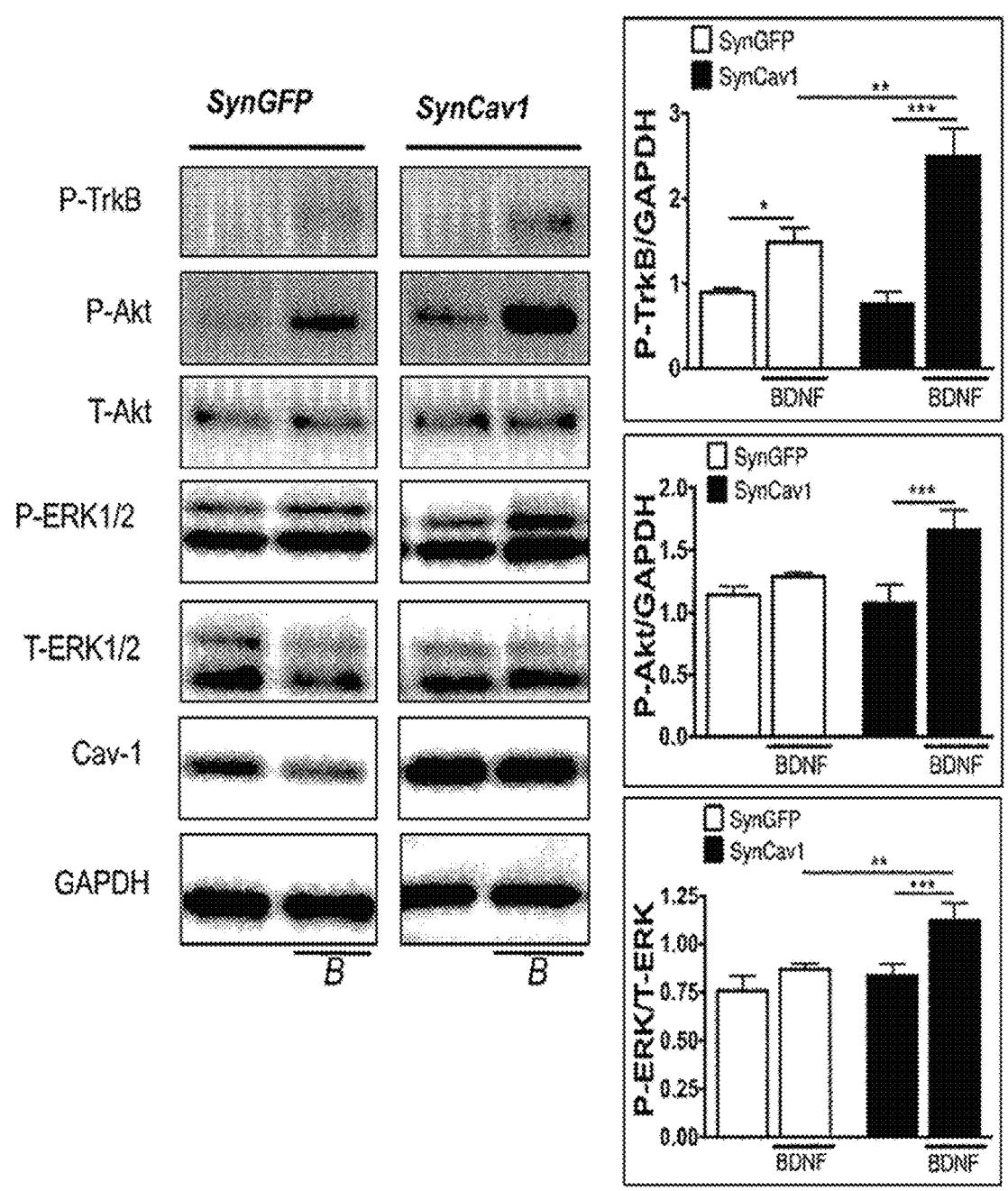
Figure 11E:
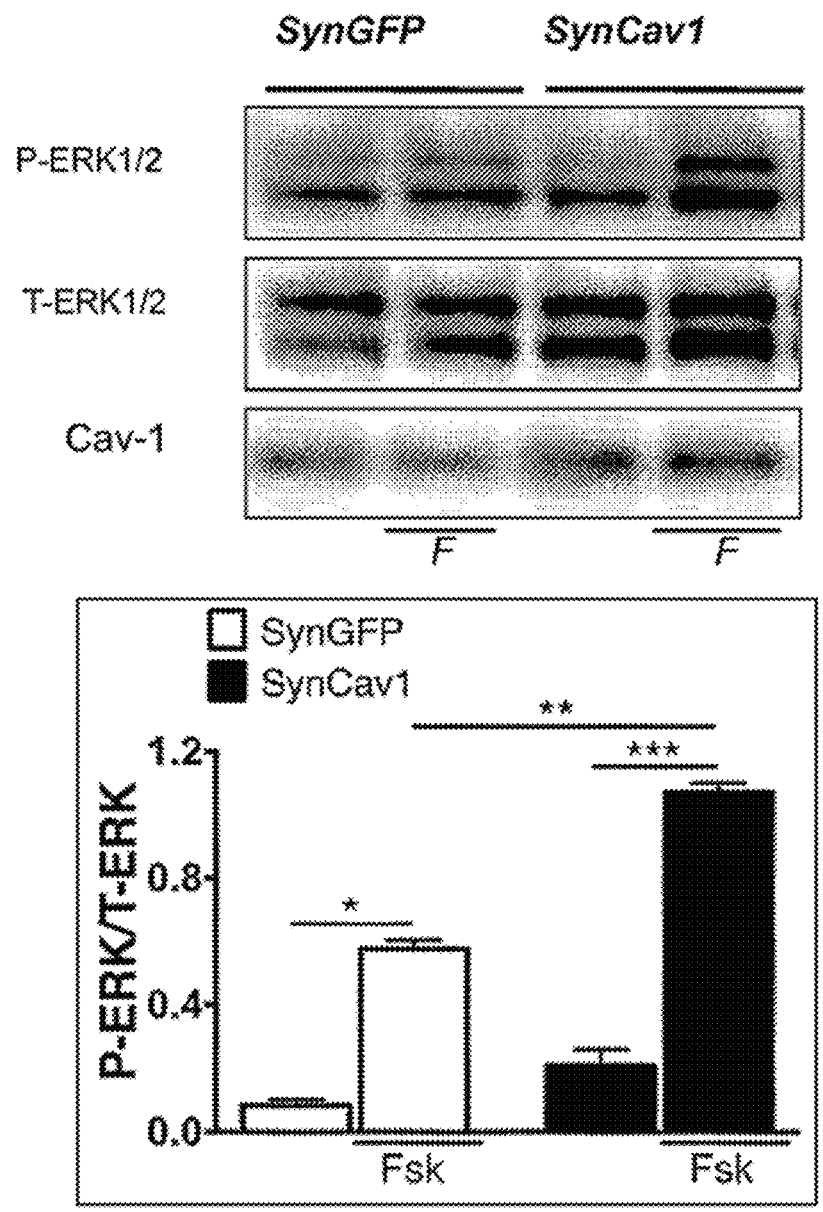
Figure 11F:
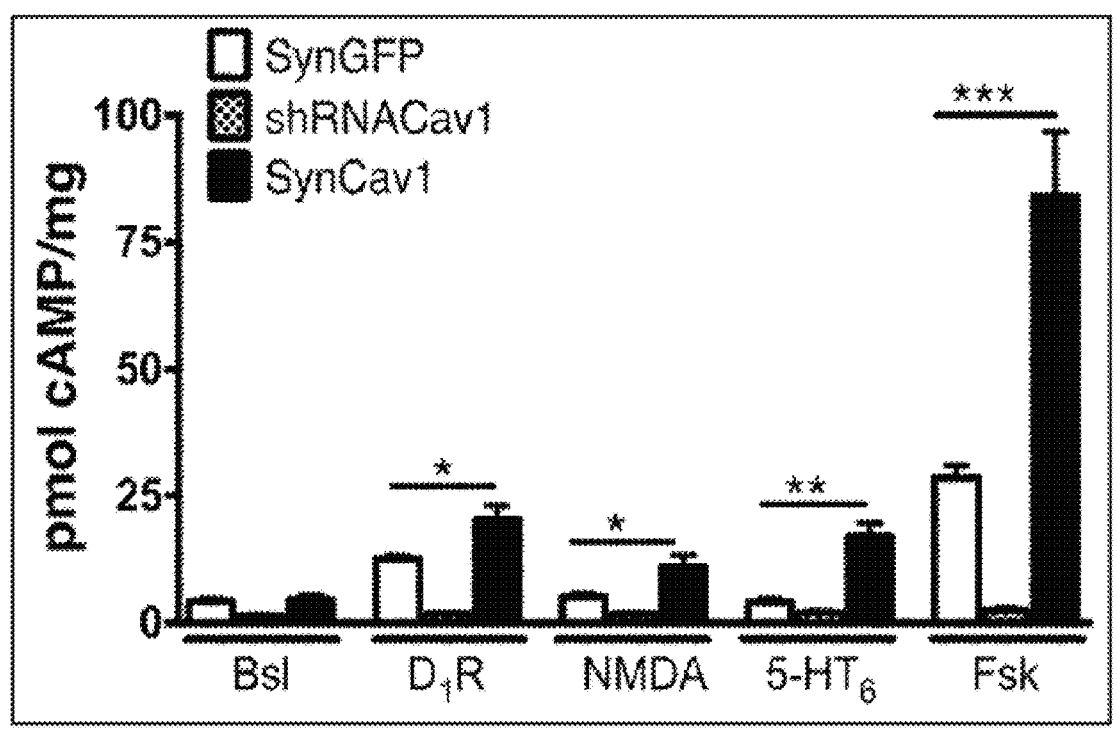

We previously have shown that siKNA mediated knockdown of Cav-1 disrupts NMDA-mediated signaling and blunts neuroprotection following oxygen glucose deprivation (9). Moreover, Cav-1 KO mice exhibit reduced synaptic signaling and scaffolding proteins in hippocampal synaptosomes and this is associated with an inability to be preconditioned against lethal ischemia (32). We therefore tested if neuron-targeted Cav-1 expression would enhance membrane/lipid rafts formation and expression of synaptic receptors and in addition, would promote pro-survival signaling. SynCav1, a vector that contains the synapsin promoter upstream of Cav specifically targets Cav-1 expression to neurons (32) (FIG. 11). To show that this vector specifically expresses Cav-1 in neurons, we isolated glia from Cav-1 KO mice that had been incubated with SynCav1 for 72 hrs. As a positive control, we incubated glia from Cav-1 mice with a non-tissue specific adenoviral vector containing the Cav-1 gene. Glia from Cav-1 KO mice expressed Cav-1 if incubated with the non-specific AdvCav1 vector but not if isolated from the SynCav1, indicating the neuronal specificity of SynCav1 (FIG. 11A). Treatment of primary neurons from wild type (WT) mice with SynCav-1-containing-lentivirus significantly enhanced expression of membrane/lipid rafts (as assessed by CT-B), PSD-95, NR2A, NR2B, TrkB, and AMPAR, compared to control virus (SynGFP) (from n=6 experiments, $p<0.05$, unpaired t test) (FIG. 11B). To confirm that SynCav1-induced increase in expression of pro-survival proteins (e.g., NR2A, NR2B, TrkB) results in functional signaling, we wanted to confirm that this increase results in functional pro-survival signaling at synaptic rather than extra-synaptic sites (33). We thus transfected neurons with SynCav1 for 72 hr and then stimulated them with NMDA (N, 10 μM), BDNF (B, 50 ng/ml), or Fsk (F, 10 μM) for 10 min. In SynCav1-incubated neurons, stimulation with NMDA enhanced activation of pro-survival kinases P-Src, P-CaMKII, and P-ERK1/2 compared to NMDA-treatment of SynGFP incubated neurons (n=4 experiments, $p<0.05$, unpaired t test) (FIG. 11C). BDNF enhanced P-TrkB, P-Akt and P-ERK1/2 in SynCav1-incubated neurons (n=4 experiments, $p<0.05$, unpaired t test) (FIG. 11D). Forskolin enhanced P-ERK1/2 in neurons incubated with SynCav1 (n=4 experiments, $p<0.05$, unpaired t test) (FIG. 11E). Incubation with SynCav1 significantly increased cAMP formation in response to agonism of the dopamine 1 receptor (DtR), NMDAR, serotonin receptor (5-HT6), or with stimulation of adenylyl cyclase with forskolin (Fsk, n=4 experiments, $p<0.05$, unpaired t test); AdvshRNACav1-incubated neurons showed a loss of D1R-, NMDAR-, 5-HT6, Fsk-stimulated cAMP formation (FIG. 11F). These results thus demonstrate that neuron-targeted Cav-1 over-expression in primary neurons enhances expression of pro-survival receptors and membrane/lipid rafts and in addition, enhances activity of pro-growth signaling molecules (e.g., activation of pro-survival kinases and cAMP synthesis).

Neuron-Targeted Over-Expression of Cav-1 Enhances Dendrite Number and Length and Expression of Membrane/Lipid Rafts.

Since pro-growth signaling components were elevated with in SynCav1-transfected neurons, we tested whether such neurons have enhanced growth and arborization of their dendrites. We found that primary neurons treated with SynCav1 for 21 days have enhanced membrane/lipid rafts expression (as indicated by CT-B), and a 3- to 4-fold increase in dendritic length (n=4 experiments, p<0.05, unpaired t test) (FIG. 12A). This treatment also enhanced branching, length, area, and volume of dendrites of Syn-Cav1-incubated neurons compared to such features in Syn-GEP-incubated neurons (from n=4 experiments, p<0.05, unpaired t test), as quantitated using Autoneuron (MBF Bioscience) (FIG. 12B). Analysis using scanning electron microscopy (SEM) revealed that SynCav1-incubated (FIG. 13B,b) neurons display enhanced dendritic arborization compared to SynGFP-incubated (FIG. 13A,a). Thus, neuron-targeted Cav-1 enhances pro-survival receptor expression and signaling molecules that promote dendritic growth in primary neurons.

Neuron-Targeted Re-Expression of Cav-1 in Cav-1 KO Neurons Restores Pro-Survival Signaling and Enhances Dendritic and Axonal Growth.

To assess the ability of Cav-1 to restore pro-survival signaling and function in Cav-1 KO neurons, we incubated neurons from Cav-1 KO mice with lentiviruses that contained SynCav1 or SynGFP. SynCav1-containing lentivirus restored Cav-1 expression, significantly enhanced NMDA-mediated P-Src and P-ERK1/2, BDNF-mediated P-Akt, P-Src, and P-ERK1/2, and Fsk-mediated P-ERK1/2 within 72 hr after incubation with the lentivirus (n=3-4 experiments, p<0.05, unpaired t test) (FIG. 14A). Immunofluorescence confocal microscopy showed that the incubation with the SynCav1 lentivirus enhanced dendritic branching, length, area, and volume, as assessed by quantification of MAP2 and by the use of Autoneuron (n=6 experiments, p<0.05, unpaired t test) (FIG. 14B). These data thus show that re-expression of Cav-1 in neurons that are deficient in Cav-1 restores pro-survival and pro-growth signaling in association with enhanced growth and arborization of dendrites.

SynCav1 Promotes Dendritic Arborization in the Presence of Neuronal Growth Inhibitors.

A major limitation to neuronal growth and repair in vivo is the presence of growth inhibitors, such as inflammatory cytokines (34) and myelin-associated glycoproteins, in the region surrounding the core of an injury (26). After injury (stroke or trauma), substantial activation of astrocytes and microglia occurs that is associated with the elaboration of inflammatory cytokines such as TNFα and IL-1β. In addition, myelin-associated glycoproteins, MAG and Nogo, which are present in the injured brain, act as growth inhibitors and limit neuronal sprouting and growth. We thus assessed whether expression of SynCav1 could promote growth in the presence of these inhibitors. WT and Cav-1 KO primary neurons (DIV3) were pre-treated with TNFα, IL-1β or MAG plus Nogo for four days. The neurons were then incubated with SynCav1 lentivirus and cultured for an additional 21 days. We found that even in the presence of the growth inhibitors, addition of the SynCav1 lentivirus increased neuronal brandling, length, and area compared to control neurons incubated with SynGFP lentivirus (n=4-7 experiments, p<0.001, One-way ANOVA Bonferroni's Multiple Comparison Test) (FIG. 15A) or to neurons from Cav-1 KO mice (n=4-7 experiments, p<0.001, One-way ANOVA Bonferroni's Multiple Comparison Test) (FIG. 15B). Notably, we found that addition of the SynCav1 lentivirus 4 days after cytokine and MAG/Nogo exposure was able to augment neuronal growth.

SynCav1 Increases Membrane Cholesterol.

To confirm the effect from SynCav1 on membrane/lipid rafts, we performed sucrose density fractionation on neurons incubated with either SynCav1 or SynGFP followed by cholesterol measurements and immunoblot analysis. Syn-Cav1 significantly increased cholesterol in buoyant membrane fractions 4 (6 fold) and 5 (~20%) (n=3 experiments, p<0.001, One-way ANOVA Bonferroni's Multiple Comparison Test) (FIG. 16A). Immunoblot analysis detected an increase in PSD-95 and Cav-1 in the buoyant membrane fractions of SynCav1-incubated neurons compared to Syn-GFP (FIG. 16B). To assess the role of cholesterol and membrane/lipid rafts on SynCav1-mediated pro-survival signaling, we pre-treated neurons with the cholesterol removing agent M(3CD (30 min, 3 mlvl) or cholesterol-M (3CD control (1:6 ration, 50 µg/ml) as previously described (35). Pre-treatment with M(3CD blunted NMDA (N), BDNF (B), and Fsk (F)-mediated activation of P-ERK1/2 in Syn-Cav1 incubated neurons, while the cholesterol loaded control SynCav1 neurons still exhibited an increase in NMDA, BDNF, and Fsk-mediated P-ERK1/2 compared to SynGFP (FIG. 16C).

Discussion

In this study, we tested the effect of neuron-targeted Cav-1 expression (SynCav1) on pro-survival and pro-growth signaling in primary neurons in vitro. As far as we are aware, this is the first study to show that a single intervention (i.e., SynCav1) can enhance neuronal membrane/lipid raft formation, increase expression of neurotransmitter and neurotrophin receptors, elevate multiple neuronal pathways that converge to augment cAMP formation (i.e., glutamatergic, dopaminergic, serotonergic, neurotrophin-mediated), and promote neuronal growth and arborization. Furthermore, we show that genetic knockdown of Cav-1, which blunts neurotransmitter and neurotrophin-mediated signaling, can be ablated by re-expression of Cav-1. Although Cav-1 is generally considered to be a "negative" regulator of cellular signaling (36), in neuronal systems Cav-1 can have both negative and positive effects (10). The current findings extend the notion that Cav-1 can be a positive regulator of neuronal growth-promoting pathways. Our results show that, Cav-1-targeted expression in neurons increases the expression of receptors and post-receptor signaling components that promote neuronal growth and survival in addition to spatially organizing and scaffolding such molecules. One thereby achieves enhanced growth-promoting signal transduction along with increased efficacy of endogenous agonists and growth factors and of exogenous interventions that can facilitate recovery following neuronal injury or degeneration.

Lipid Rafts Promote Neuronal Growth.

Growing evidence implicates membrane/lipid rafts as an essential component for promoting growth cone expansion, neurite outgrowth, axonal brandling, and axonal guidance (6,37,38). Synapses and membrane/lipid rafts are traditionally considered distinct subcellular regions of the plasma membrane, even though they share certain characteristics that are essential to their function (e.g., enrichment in cholesterol, glycosphingolipids, sphingomyelin, and other saturated fatty acid containing lipids [GM1 gangliosides, palmitic acid]) (39). Other evidence supports a role for free cholesterol and membrane/lipid rafts in formation of neuronal synapses and in the signaling and protection of neurons (7,9,12,40,41). Moreover, as an essential component of rafts, cholesterol and changes in the cellular content of cholesterol can affect Cav expression (42,43). For example, brain-derived neurotrophic factor (BDNF), which is essential for synaptic function and development, stimulates cholesterol biosynthesis and increases membrane/lipid rafts and Cav expression in cortical and hippocampal neurons (44).

Our results show that neurons engineered to express SynCav1 have increased expression of the membrane/lipid rafts marker CT-B and significantly enhances membrane cholesterol. Several previous studies that have investigated therapeutic approaches to promote axonal regeneration and synapse formation following brain or spinal cord injury have used CT-B as an indicator of axonal regeneration and de novo synapse formation (45-47). CT-B binds to GM1-gangliosides, sialic acid-containing glycosphingolipids essential for brain development, plasticity, and neurite outgrowth (48-50). Other data have shown that exogenous GM1-ganglioside evokes the release of BDNF and promotes neuronal survival (38) and that the lack of gangliosides inhibits nerve regeneration and induces axonal damage (51,52). The latter results could help explain the loss of synaptic signaling components, signaling, and neuronal processes following siRNA-mediated knockdown of Cav-1.

SynCav1 Attenuates Elevated Basal P-ERK1/2 in Cav-1 KO Neurons.

Our group has previously shown that re-expression of Cav-1 in Cav-1 KO neurons attenuates elevated basal levels of P-ERK and restores NMDA-mediated activation of P-Src and P-ERK1/2 (9). In addition to our group, other laboratories have demonstrated that elevated basal P-ERK1/2 occurs in a variety of tissue ranging from myocardium to lung to the vasculature (9,53-56). Although mechanistically not completely understood, Cav-1 KO mice exhibit hypertrophy, neoplasia, increased cyclin D levels, elevated metalloproteinase secretion and Smad-2 hyperactivation. The present paper again demonstrates high basal P-ERK in Cav-1 KO neurons, and that this again is attenuated with re-expression of Cav-1 (e.g., SynCav1).

Cav-1 Scaffolds Pro-Survival and Pro-Growth Neuronal Signaling Components.

Cav-1 and membrane/lipid rafts have previously been shown to localize neuronal signaling components that contribute to neurotransmission (9,10,14-16,57). Cav-1 and membrane/lipid rafts can regulate estrogen receptor signaling (58), glutamate receptor neurotransmission (9,43,59), and neurotrophin receptor signaling (TrkB and p75) (14,57). Although NMDAR subtypes are critical for neuroprotection against ischemic injury and for neurotransmission, their localization to extra-synaptic regions can facilitate neuronal cell death (33). Therefore, the subcellular localization of these signaling pathways helps determine neuronal cell fate. NMDAR-mediated activation of pro-survival kinases, which include CaMKII, Src, and ERK1/2, predominantly occurs in synaptic regions (33). A key finding in the present study is that SynCav1-mediated enhanced expression of NMDAR subtypes promotes a pro-survival pathway, which is dependent upon membrane cholesterol.

These results extend those that have shown the loss of Cav-1, either through siRNA or transgenic models, can blunt neuroprotection (9), metabotropic glutamate receptor-mediated long term depression (43,59) and accelerate a neurodegenerative phenotype (32,60,61). Our findings obtained with siRNA-mediated Cav-1 knockdown extend the role of Cav-1 in neuronal signaling to a variety of receptors in addition to glutamate. Interestingly, many of these receptors signal via regulating the formation of cAMP, a second messenger that regulates neuronal survival as well as growth of dendrites and axons (17,19,21). A more recent finding demonstrates that recruitment of TrkB receptors to neuronal lipid rafts, via adenosine A2A receptor activation, was required for BDNF-induced hippocampal long-term potentiation of CA1 synapses (35). This recruitment to lipid rafts by A2A receptor activation also enhanced P-TrkB, an effect that was mimicked by forskolin and blocked by PKA or Src inhibition. These findings are akin to our data which show that transfection with SynCav1 enhances expression of the lipid raft marker CT-B, enhances membrane cholesterol, augments BDNF-mediated P-TrkB, and forskolin-stimulated cAMP production (FIGS. 11 & 12). Although cAMP and cGMP promote, respectively, the growth of axons and dendrites (21), the precise role of Cav-1 in cGMP-mediated dendritic growth remains to be determined. Nevertheless, our data has implications for neuronal repair and emphasize the potentially beneficial effects of neuron-targeted Cav-1 in the enhancement of multiple signaling pathways that converge upon cAMP formation.

Loss of Cav-1 May Contribute to Neurodegeneration.

Cav-1 KO mice have CNS pathology similar to that exhibited in neurodegenerative diseases; such features include altered glutamate receptor signaling (9,43,59), motor and behavioral abnormalities, increased ischemic cerebral injury, impaired spatial memory, and cholinergic function (60-62). Other recent evidence has demonstrated that the localization of synaptic signaling components in neuronal membrane/lipid rafts and synaptosomes is reduced in brains from aged WT and young Cav-1 KO mice, and that Cav-1 KO mice develop a neuropathological phenotype similar to that of Alzheimer's disease (32).

In summary, data in this study show that not only do membrane/lipid rafts and Cav-1 provide a key nexus for pro-survival and pro-growth signaling components but also that an increase in expression of Cav-1 in neurons may be a novel means to preserve, restore and enhance neuronal function following injury. Application of these results and this concept, in particular to augment the capacity of the brain to undergo repair in settings such as stroke and traumatic brain injury or during late stages of neurodegenerative diseases may have important therapeutic implications.

References Cited in Example 3

1. Toescu, E. C., Verkhratsky, A., and Landfield, P. W. (2004) Trends Neurosci 27, 614-620
2. Hattiangady, B., Rao, M. S., Shetty, G. A., and Shetty, A. K. (2005) Exp Neurol 195, 353-371
3. Hotulainen, P., and Hoogenraad, C. C. (2010) J Cell Biol 189, 619-629
4. Huber, A. B., Kolodkin, A. L., Ginty, D. D., and Cloutier, J. F. (2003) Annu Rev Neurosci 26, 509-563
5. Calabrese, B., Wilson, M. S., and Halpain, S. (2006) Physiology (Bethesda) 21, 38-47
6. Guirland, C., and Zheng, J. Q. (2007) Adv Exp Med Biol 621, 144-155
7. Mauch, D. H., Nagler, K., Schumacher, S., Goritz, C., Muller, E. C., Otto, A., and Pfrieger, F. W. (2001) Science 294, 1354-1357
8. Allen, J. A., Halverson-Tamboli, R. A., and Rasenick, M. M. (2007) Nat Rev Neurosci 8, 128-140

9. Head, B. P., Patel, H. H., Tsutsumi, Y. M., Hu, Y., Mejia, T., Mora, R. C., Insel, P. A., Roth, D. M., Drummond, J. C., and Patel, P. M. (2008) Faseb J22, 828-840
10. Stern, C. M., and Mermelstein, P. G. (2010) Cell Mol Life Sci 67, 3785-3795
11. Oshikawa, J., Toya, Y., Fujita, T., Egawa, M., Kawabe, J., Umemura, S., and Ishikawa, Y. (2003) Am J Physiol Cell Physiol 285, C567-574
12. Willmann, R., Pun, S., Stallmach, L., Sadasivam, G., Santos, A. F., Caroni, P., and Fuhrer, C. (2006) Embo J 25, 4050-4060
13. Smart, E. J., Graf, G. A., McNiven, M. A., Sessa, W. C., Engelman, J. A., Scherer, P. E., Okamoto, T., and Lisanti, M. P. (1999) Mol Cell Biol 19, 7289-7304
14. Bilderback, T. R., Gazula, V. R., Lisanti, M. P., and Dobrowsky, R. T. (1999) J Biol Chem 274, 257-263
15. Hibbert, A. P., Kramer, B. M., Miller, F. D., and Kaplan, D. R. (2006) Mol Cell Neurosci 32, 387-402
16. Bjork, K., Sjogren, B., and Svenningsson, P. (2010) Exp Cell Res 316, 1351-1356
17. Neumann, S., Bradke, F., Tessier-Lavigne, M., and Basbaum, A. I. (2002) Neuron 34, 885-893
18. Wayman, G. A., Impey, S., Marks, D., Saneyoshi, T., Grant, W. F., Derkach, V., and Soderling, T. R. (2006) Neuron 50, 897-909
19. MacDonald, E., Van der Lee, H., Pocock, D., Cole, C., Thomas, N., VandenBerg, P. M., Bourtchouladze, R., and Kleim, J. A. (2007) Neurorehabil Neural Repair 21, 486-496
20. Saneyoshi, T., Wayman, G., Fortin, D., Davare, M., Hoshi, N., Nozaki, N., Natsume, T., and Soderling, T. R. (2008) Neuron 57, 94-107
21. Murray, A. J., Tucker, S. J., and Shewan, D. A. (2009) J Neurosci 29, 15434-15444
22. Atkins, C. M., Oliva, A. A., Jr., Alonso, O. F., Pearse, D. D., Bramlett, H. M., and Dietrich, W. D. (2007) Exp Neurol 208, 145-158
23. Hicks, R. R, Zhang, L., Dhillon, H. S., Prasad, M. R., and Seroogy, K. B. (1998) Brain Res Mol Brain Res 59, 264-268
24. Biegon, A., Fry, P. A., Paden, C. M., Alexandrovich, A., Tsenter, J., and Shohami, E. (2004) Proc Natl Acad Sci USA 101, 5117-5122
25. Atkins, C. M., Falo, M. C., Alonso, O. F., Bramlett, H. M., and Dietrich, W. D. (2009) Neurosci Lett 459, 52-56
26. Carmichael, S. T. (2008) Stroke 39, 1380-1388
27. Lemkuil, B. P., Head, B. P., Pearn, M. L., Patel, H. H., Drummond, J. C., and Patel, P. M. (2011) Anesthesiology 114, 49-57
28. Head, B. P., Patel, H. H., Roth, D. M., Lai, N. C., Niesman, I. R., Farquhar, M. G., and Insel, P. A. (2005) J Biol Chem 280, 31036-31044
29. Head, B. P., Patel, H. H., Roth, D. M., Murray, F., Swaney, J. S., Niesman, I. R., Farquhar, M. G., and Insel, P. A. (2006) J Biol Chem 281, 26391-26399
30. Yam, P. Y., Li, S., Wu, J., Hu, J., Zaia, J. A., and Yee, J. K. (2002) Mol Ther 5, 479-484
31. Yee, J. K., Friedmann, T., and Burns, J. C. (1994) Methods Cell Biol 43 Pt A, 99-112
32. Head, B. P., Peart, J. N., Panneerselvam, M., Yokoyama, T., Pearn, M. L., Niesman, I, R., Bonds, J. A., Schilling, J. M., Miyanohara, A., Headrick, J., Ali, S. S., Roth, D. M., Patel, P. M., and Patel, H. H. (2010) P LoS One 5, el 5697
33. Hardingham, G. R, and Bading, H. (2003) Trends Neurosci 26, 81-89
34. Suzumura, A., Takeuchi, H., Zhang, G., Kuno, R., and Mizuno, T. (2006) Ann N Y Acad Sci 1088, 219-229
35. Assaife-Lopes, N., Sousa, V. C., Pereira, D. B., Ribeiro, J. A., Chao, M. V., and Sebastiao, A. M. (2010) J Neurosci 30, 8468-8480
36. Lisanti, M. P., Scherer, P. E., Tang, Z., and Sargiacomo, M, (1994) Trends Cell Biol 4, 231-235
37. Grider, M. H., Park, D., Spencer, D. M., and Shine, H. D. (2009) J Neurosci Res
38. Lim, S. T., Esfahani, K., Avdoshina, V., and Mocchetti, I. (2010) Neuropharmacology
39. Pike, L. J. (2009) J Lipid Res 50 Suppl, S323-328
40. Hering, H., Lin, C. C., and Sheng, M. (2003) J Neurosci 23, 3262-3271
41. Renner, M., Choquet, D., and Triller, A. (2009) J Neurosci 29, 2926-2937
42. Bist, A., Fielding, C. J., and Fielding, P. E. (2000) Biochemistry 39, 1966-1972
43. Francesconi, A., Kumari, R., and Zukin, R. S. (2009) J Neurosci 29, 3590-3602
44. Suzuki, S., Kiyosue, K., Hazama, S., Ogura, A., Kashihara, M., Hara, T., Koshimizu, H., and Kojima, M. (2007) J Neurosci 27, 6417-6427
45. Alto, L. T., Havton, L. A., Conner, J. M., Hollis Ii, E. R., Blesch, A., and Tuszynski, M. H. (2009) Nat Neurosci 12, 1106-1113
46. Lee, H., McKeon, R. J., and Bellamkonda, R. V. (2010) Proc Natl Acad Sci USA 107, 3340-3345
47. Li, S., Overman, J. J., Katsman, D., Kozlov, S. V., Donnelly, C. J., Twiss, J. L., Giger, R. J., Coppola, G., Geschwind, D. H., and Carmichael, S. T. (2010) Nat Neurosci 13, 1496-1504
48. Svennerholm, L. (1956) Nature 177, 524-525
49. Suzuki, K. (1965) J Neurochem 12, 629-638
50. Deny, D. M., and Wolfe, L. S. (1967) Science 158, 1450-1452
51. Sparrow, J. R., McGuinness, C., Schwartz, M., and Grafstein, B. (1984) J Neurosci Res 12, 233-243

What is claimed:

1. A method of transferring the caveolin-1 gene into a neural stem cell or neuronal cell comprising introducing an expression system into the neural stem cell or neuronal cell, thereby transferring the caveolin-1 gene into a neural stem cell or neuronal cell, respectively; wherein the expression system for producing Caveolin-1 in neuronal cells or neural stem cells comprises:
   (a) a neuron-specific regulatory element; and
   (b) a nucleic acid sequence encoding Caveolin-1,
wherein the neuron-specific regulatory element of (a) is a promoter and located upstream of the nucleic acid sequence encoding Caveolin-1 of (b) and directs the expression of Caveolin-1 in the neural stem cell or neuronal cell.

2. The method of claim 1, wherein the nucleic acid sequence encoding Caveolin-1 is set forth in SEQ ID NO:1 beginning at position 568 and ending at position 1104.

3. The method of claim 1, wherein the nucleic acid sequence encoding Caveolin-1 is set forth in SEQ ID NO:5 beginning at position 1 and ending at position 537.

4. The method of claim 1, wherein the nucleic acid sequence encoding Caveolin-1 is set forth in SEQ ID NO:7 beginning at position 1 and ending at position 537.

5. The method of claim 1, wherein the neuron-specific regulatory element is the synapsin promoter as set forth in FIG. 8 (SEQ ID NO:1) beginning at position 21 and ending at position 489.

6. A method for promoting neural cell growth comprising transforming an expression system comprising (a) a neuron-specific regulatory element; and (b) a nucleic acid sequence encoding Caveolin-1 into a neuronal cells, wherein the neuron-specific regulatory element of (a) is a promoter and located upstream of the nucleic acid sequence encoding Caveolin-1 of (b) and directs the expression of Caveolin 1 in the neural cells in a sufficient amount so as to promote neural cell growth.

7. A method of increasing synapse formation and improving synaptic function in neurodegenerative diseases by promoting neural cell growth in a subject by the method of claim 6, thereby increasing synapse formation and improving synaptic function.

8. The method of claim 7, wherein the neurodegenerative disease is Alzheimer's Disease.

* * * * *

SEQUENCE LISTING

```
<160> NUMBER OF SEQ ID NOS: 14

<210> SEQ ID NO 1
<211> LENGTH: 1199
<212> TYPE: DNA
<213> ORGANISM: Artificial Sequence
<220> FEATURE:
<223> OTHER INFORMATION: Syn promoter-Cav1
<220> FEATURE:
<221> NAME/KEY: misc_feature
<222> LOCATION: (1)..(1199)
<223> OTHER INFORMATION: Human Synapsin I (Syn1) promoter-mouse
```

```
      caveolin-1 (Cav1) protein coding sequence cassette
<220> FEATURE:
<221> NAME/KEY: misc_feature
<222> LOCATION: (1)..(26)
<223> OTHER INFORMATION: Multiple cloning sequence
<220> FEATURE:
<221> NAME/KEY: misc_feature
<222> LOCATION: (1)..(6)
<223> OTHER INFORMATION: MluI/AflIII  restriction enzyme recognition
      sequence
<220> FEATURE:
<221> NAME/KEY: misc_feature
<222> LOCATION: (7)..(12)
<223> OTHER INFORMATION: ClaI/BspDI/BanIII/Bsa29I/BseCI/BshVI/BsiXI/
      Bsp106I/BspXI/Bsu15I/BsuTUI/ZhoI  restriction enzyme recognition
      sequence
<220> FEATURE:
<221> NAME/KEY: misc_feature
<222> LOCATION: (13)..(18)
<223> OTHER INFORMATION: KasI/NarI/SfoI/BbeI/DinI/EgeI/EheI/Mly113I
      restriction enzyme recognition sequence
<220> FEATURE:
<221> NAME/KEY: misc_feature
<222> LOCATION: (18)..(23)
<223> OTHER INFORMATION: PvuII restriction enzyme recognition sequence
<220> FEATURE:
<221> NAME/KEY: misc_feature
<222> LOCATION: (21)..(26)
<223> OTHER INFORMATION: PstI/BspMAI restriction enzyme recognition
      sequence
<220> FEATURE:
<221> NAME/KEY: misc_feature
<222> LOCATION: (21)..(489)
<223> OTHER INFORMATION: Homo sapiens synapsin I (Syn1) promoter
      sequence corresponding to nucleotide position 1889-2357 of GenBank
      Accession No. M55301
<220> FEATURE:
<221> NAME/KEY: misc_feature
<222> LOCATION: (229)..(241)
<223> OTHER INFORMATION: Conserved sequence element, CSTTYGCCYCYGC,
      shared with other neuron-specifically transcribed genes or
      promoters, including those for human and rat synapsin I,
      neurofilament, and nerve growth factor receptor, where S = C or G
      and Y = C or T
<220> FEATURE:
<221> NAME/KEY: misc_feature
<222> LOCATION: (279)..(287)
<223> OTHER INFORMATION: Conserved sequence element, CGSTGACGTCNC,
      shared with other neuron-specifically transcribed genes or
      promoters, including those for human and rat synapsin I,
      neurofilament, and nerve growth factor receptor, where S = C or G
      and N = A, G, C or T
<220> FEATURE:
<221> NAME/KEY: misc_feature
<222> LOCATION: (284)..(291)
<223> OTHER INFORMATION: cAMP-responsive element, TGACGTCA
<220> FEATURE:
<221> NAME/KEY: misc_feature
<222> LOCATION: (442)..(442)
<223> OTHER INFORMATION: Start site of transcription from synapsin I
      promoter
<220> FEATURE:
<221> NAME/KEY: misc_feature
<222> LOCATION: (489)..(508)
<223> OTHER INFORMATION: Multiple cloning sequence
<220> FEATURE:
<221> NAME/KEY: misc_feature
<222> LOCATION: (489)..(494)
<223> OTHER INFORMATION: SalI restriction enzyme recognition sequence
<220> FEATURE:
<221> NAME/KEY: misc_feature
<222> LOCATION: (495)..(500)
<223> OTHER INFORMATION: Acc65I/KpnI/Asp718I restriction enzyme
      recognition sequence
<220> FEATURE:
<221> NAME/KEY: misc_feature
<222> LOCATION: (503)..(508)
<223> OTHER INFORMATION: ApaI/PspOMI/Bsp120I restriction enzyme
      recognition sequence
```

```
<220> FEATURE:
<221> NAME/KEY: misc_feature
<222> LOCATION: (506)..(512)
<223> OTHER INFORMATION: Sequence, CCCAAAC, obtained after replacing
      SmaI-NotI EGFP-containing fragment of pSyn-EGFP DNA with 685 bp
      PmeI-NotI Cav1-coding sequence fragment to obtain pSyn-Cav1 DNA;
      sequence is from joining SmaI end (CCC) to PmeI end (AAAC)
<220> FEATURE:
<221> NAME/KEY: misc_feature
<222> LOCATION: (509)..(530)
<223> OTHER INFORMATION: Homology to nucleotide position 7437-7417 of
      GenBank Accession No. AB617819
<220> FEATURE:
<221> NAME/KEY: misc_feature
<222> LOCATION: (525)..(1179)
<223> OTHER INFORMATION: Mus musculus caveolin 1 (Cav1) sequences
      corresponding to nucleotide position 73-727 of NCBI Reference
      Sequence Accession No. NM_007616
<220> FEATURE:
<221> NAME/KEY: CDS
<222> LOCATION: (568)..(1104)
<223> OTHER INFORMATION: Sequences coding for caveolin 1 protein,
      corresponding to nucleotide position 116-652 of NCBI Reference
      Sequence Accession No. NM_007616 or nucleotide position 24-560
      of GenBank Accession No. BC038280
<220> FEATURE:
<221> NAME/KEY: misc_feature
<222> LOCATION: (568)..(570)
<223> OTHER INFORMATION: Translational initiation codon, ATG, within
      caveolin 1 coding sequence
<220> FEATURE:
<221> NAME/KEY: misc_feature
<222> LOCATION: (1102)..(1104)
<223> OTHER INFORMATION: Translational termination codon, TGA, within
      caveolin 1 coding sequence
<220> FEATURE:
<221> NAME/KEY: misc_feature
<222> LOCATION: (1186)..(1191)
<223> OTHER INFORMATION: EcoRI/FunII restriction enzyme recognition
      sequence
<220> FEATURE:
<221> NAME/KEY: misc_feature
<222> LOCATION: (1192)..(1199)
<223> OTHER INFORMATION: NotI/CciNI restriction enzyme recognition
      sequence
<300> PUBLICATION INFORMATION:
<301> AUTHORS: Sauerwald A, Hoesche C, Oschwald R, Kilimann MW
<302> TITLE: The 5'-flanking region of the synapsin I gene. A G+C-rich,
      TATA- and CAAT-less, phylogenetically conserved sequence with cell
      type-specific promoter function
<303> JOURNAL: Journal of Biological Chemistry
<304> VOLUME: 265
<306> PAGES: 14932-14937
<307> DATE: 1990-09-05
<313> RELEVANT RESIDUES IN SEQ ID NO: (229)..(241)
<300> PUBLICATION INFORMATION:
<301> AUTHORS: Sauerwald A, Hoesche C, Oschwald R, Kilimann MW
<302> TITLE: The 5'-flanking region of the synapsin I gene. A G+C-rich,
      TATA- and CAAT-less, phylogenetically conserved sequence with cell
      type-specific promoter function
<303> JOURNAL: Journal of Biological Chemistry
<304> VOLUME: 265
<306> PAGES: 14932-14937
<307> DATE: 1990-09-05
<313> RELEVANT RESIDUES IN SEQ ID NO: (279)..(287)
<300> PUBLICATION INFORMATION:
<301> AUTHORS: Sauerwald A, Hoesche C, Oschwald R, Kilimann MW
<302> TITLE: The 5'-flanking region of the synapsin I gene. A G+C-rich,
      TATA- and CAAT-less, phylogenetically conserved sequence with cell
      type-specific promoter function
<303> JOURNAL: Journal of Biological Chemistry
<304> VOLUME: 265
<306> PAGES: 14932-14937
<307> DATE: 1990-09-05
<313> RELEVANT RESIDUES IN SEQ ID NO: (284)..(291)
<300> PUBLICATION INFORMATION:
<301> AUTHORS: Sauerwald A, Hoesche C, Oschwald R, Kilimann MW
<302> TITLE: The 5'-flanking region of the synapsin I gene. A G+C-rich,
      TATA- and CAAT-less, phylogenetically conserved sequence with cell
``` type-specific promoter function
<303> JOURNAL: Journal of Biological Chemistry
<304> VOLUME: 265
<306> PAGES: 14932-14937
<307> DATE: 1990-09-05
<313> RELEVANT RESIDUES IN SEQ ID NO: (442)..(442)

<400> SEQUENCE: 1

| | |
|---|---:|
| acgcgtatcg atggcgccag ctgcagaggg ccctgcgtat gagtgcaagt gggttttagg | 60 |
| accaggatga ggcggggtgg gggtgcctac ctgacgaccg accccgaccc actgacaag | 120 |
| cacccaaccc ccattcccca aattgcgcat ccctatcag agaggggag gggaaacagg | 180 |
| atgcggcgag gcgcgtgcgc actgccagct tcagcaccgc ggacagtgcc ttcgcccccg | 240 |
| cctggcggcg cgcgccaccg ccgcctcagc actgaaggcg cgctgacgtc actcgccggt | 300 |
| cccccgcaaa ctcccctcc cggccaccctt ggtcgcgtcc gcgccgccgc cggcccagcc | 360 |
| ggaccgcacc acgcgaggcg cgagataggg gggcacgggc gcgaccatct gcgctgcggc | 420 |
| gccggcgact cagcgctgcc tcagtctgcg gtgggcagcg gaggagtcgt gtcgtgcctg | 480 |
| agagcgcagt cgacggtacc gcgggcccaa acgaattcgc ccttccaggg aaacctcctc | 540 |
| agagcctgca gccagccacg cgccagc atg tct ggg ggc aaa tac gta gac tcc | 594 |
|                                                  Met Ser Gly Gly Lys Tyr Val Asp Ser<br>                                                  1               5 | |
| gag gga cat ctc tac act gtt ccc atc cgg gaa cag ggc aac atc tac<br>Glu Gly His Leu Tyr Thr Val Pro Ile Arg Glu Gln Gly Asn Ile Tyr<br>10               15                 20               25 | 642 |
| aag ccc aac aac aag gcc atg gca gac gag gtg act gag aag caa gtg<br>Lys Pro Asn Asn Lys Ala Met Ala Asp Glu Val Thr Glu Lys Gln Val<br>              30                 35               40 | 690 |
| tat gac gcg cac acc aag gag att gac ctg gtc aac cgc gac ccc aag<br>Tyr Asp Ala His Thr Lys Glu Ile Asp Leu Val Asn Arg Asp Pro Lys<br>         45                 50               55 | 738 |
| cat ctc aac gac gac gtg gtc aag att gac ttt gaa gat gtg att gca<br>His Leu Asn Asp Asp Val Val Lys Ile Asp Phe Glu Asp Val Ile Ala<br>        60                65               70 | 786 |
| gaa cca gaa ggg aca cac agt ttc gac ggc atc tgg aag gcc agc ttc<br>Glu Pro Glu Gly Thr His Ser Phe Asp Gly Ile Trp Lys Ala Ser Phe<br>75               80                 85 | 834 |
| acc acc ttc act gtg aca aaa tat tgg ttt tac cgc ttg ttg tct acg<br>Thr Thr Phe Thr Val Thr Lys Tyr Trp Phe Tyr Arg Leu Leu Ser Thr<br>90               95                 100             105 | 882 |
| atc ttc ggc atc cca atg gca ctc atc tgg ggc att tac ttt gcc att<br>Ile Phe Gly Ile Pro Met Ala Leu Ile Trp Gly Ile Tyr Phe Ala Ile<br>              110                115               120 | 930 |
| ctc tcc ttc ctg cac atc tgg gcg gtt gta ccg tgc atc aag agc ttc<br>Leu Ser Phe Leu His Ile Trp Ala Val Val Pro Cys Ile Lys Ser Phe<br>          125                130               135 | 978 |
| ctg att gag att cag tgc atc agc cgc gtc tac tcc atc tac gtc cat<br>Leu Ile Glu Ile Gln Cys Ile Ser Arg Val Tyr Ser Ile Tyr Val His<br>140             145                150 | 1026 |
| acc ttc tgc gat cca ctc ttt gaa gct att ggc aag ata ttc agc aac<br>Thr Phe Cys Asp Pro Leu Phe Glu Ala Ile Gly Lys Ile Phe Ser Asn<br>155             160                165 | 1074 |
| atc cgc atc agc acg cag aaa gag ata tga gggacattta aaggatgaaa<br>Ile Arg Ile Ser Thr Gln Lys Glu Ile<br>170             175 | 1124 |
| ggttttttc cccccttact atttccttgg tgccaattcc aagttgctct cgcagaaggg | 1184 |
| cgaattcgcg gccgc | 1199 |

<210> SEQ ID NO 2
<211> LENGTH: 178
<212> TYPE: PRT
<213> ORGANISM: Artificial Sequence
<220> FEATURE:
<223> OTHER INFORMATION: Synthetic Construct

<400> SEQUENCE: 2

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Val Thr Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Glu Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Thr Ile Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Phe Cys Asp Pro Leu Phe
145                 150                 155                 160

Glu Ala Ile Gly Lys Ile Phe Ser Asn Ile Arg Ile Ser Thr Gln Lys
                165                 170                 175

Glu Ile

<210> SEQ ID NO 3
<211> LENGTH: 21
<212> TYPE: DNA
<213> ORGANISM: Artificial Sequence
<220> FEATURE:
<223> OTHER INFORMATION: sense sequence of caveolin-1 siRNA

<400> SEQUENCE: 3
ggaaauugau cuggucaact t                                           21

<210> SEQ ID NO 4
<211> LENGTH: 21
<212> TYPE: DNA
<213> ORGANISM: Artificial Sequence
<220> FEATURE:
<223> OTHER INFORMATION: antisense sequence of caveolin-1 siRNA

<400> SEQUENCE: 4
guugaccaga ucaauuucct t                                           21

<210> SEQ ID NO 5
<211> LENGTH: 537
<212> TYPE: DNA
<213> ORGANISM: Homo sapiens
<220> FEATURE:
<221> NAME/KEY: CDS
<222> LOCATION: (1)..(537)

<400> SEQUENCE: 5

```
atg tct ggg ggc aaa tac gta gac tcg gag gga cat ctc tac acc gtt    48
Met Ser Gly Gly Lys Tyr Val Asp Ser Glu Gly His Leu Tyr Thr Val
1               5                   10                  15 ccc atc cgg gaa cag ggc aac atc tac aag ccc aac aac aag gcc atg    96
Pro Ile Arg Glu Gln Gly Asn Ile Tyr Lys Pro Asn Asn Lys Ala Met
                20                  25                  30 gca gac gag ctg agc gag aag caa gtg tac gac gcg cac acc aag gag   144
Ala Asp Glu Leu Ser Glu Lys Gln Val Tyr Asp Ala His Thr Lys Glu
            35                  40                  45 atc gac ctg gtc aac cgc gac cct aaa cac ctc aac gat gac gtg gtc   192
Ile Asp Leu Val Asn Arg Asp Pro Lys His Leu Asn Asp Asp Val Val
        50                  55                  60 aag att gac ttt gaa gat gtg att gca gaa cca gaa ggg aca cac agt   240
Lys Ile Asp Phe Glu Asp Val Ile Ala Glu Pro Glu Gly Thr His Ser
65                  70                  75                  80 ttt gac ggc att tgg aag gcc agc ttc acc acc ttc act gtg acg aaa   288
Phe Asp Gly Ile Trp Lys Ala Ser Phe Thr Thr Phe Thr Val Thr Lys
                85                  90                  95 tac tgg ttt tac cgc ttg ctg tct gcc ctc ttt ggc atc ccg atg gca   336
Tyr Trp Phe Tyr Arg Leu Leu Ser Ala Leu Phe Gly Ile Pro Met Ala
                100                 105                 110 ctc atc tgg ggc att tac ttc gcc att ctc tct ttc ctg cac atc tgg   384
Leu Ile Trp Gly Ile Tyr Phe Ala Ile Leu Ser Phe Leu His Ile Trp
            115                 120                 125 gca gtt gta cca tgc att aag agc ttc ctg att gag att cag tgc atc   432
Ala Val Val Pro Cys Ile Lys Ser Phe Leu Ile Glu Ile Gln Cys Ile
        130                 135                 140 agc cgt gtc tat tcc atc tac gtc cac acc gtc tgt gac cca ctc ttt   480
Ser Arg Val Tyr Ser Ile Tyr Val His Thr Val Cys Asp Pro Leu Phe
145                 150                 155                 160 gaa gct gtt ggg aaa ata ttc agc aat gtc cgc atc aac ttg cag aaa   528
Glu Ala Val Gly Lys Ile Phe Ser Asn Val Arg Ile Asn Leu Gln Lys
                165                 170                 175 gaa ata taa                                                        537
Glu Ile

<210> SEQ ID NO 6
<211> LENGTH: 178
<212> TYPE: PRT
<213> ORGANISM: Homo sapiens

<400> SEQUENCE: 6

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
                20                  25                  30

Ala Asp Glu Leu Ser Glu Lys Gln Val Tyr Asp Ala His Thr Lys Glu
            35                  40                  45

Ile Asp Leu Val Asn Arg Asp Pro Lys His Leu Asn Asp Asp Val Val
        50                  55                  60

Lys Ile Asp Phe Glu Asp Val Ile Ala Glu Pro Glu Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
                100                 105                 110

Leu Ile Trp Gly Ile Tyr Phe Ala Ile Leu Ser Phe Leu His Ile Trp
            115                 120                 125
```

```
Ala Val Val Pro Cys Ile Lys Ser Phe Leu Ile Glu Ile Gln Cys Ile
        130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 7
<211> LENGTH: 537
<212> TYPE: DNA
<213> ORGANISM: Canis lupus
<220> FEATURE:
<221> NAME/KEY: CDS
<222> LOCATION: (1)..(537)

<400> SEQUENCE: 7 atg tct ggg ggc aaa tac gta gac tcc gag ggg cac ctc tac acc gtt        48
Met Ser Gly Gly Lys Tyr Val Asp Ser Glu Gly His Leu Tyr Thr Val
1               5                   10                  15 ccc atc cgg gag cag ggc aac atc tac aag ccc aac aac aag gcc atg        96
Pro Ile Arg Glu Gln Gly Asn Ile Tyr Lys Pro Asn Asn Lys Ala Met
            20                  25                  30 gcg gag gag atg agc gag aag cag gtg tac gac gcg cac acc aag gaa       144
Ala Glu Glu Met Ser Glu Lys Gln Val Tyr Asp Ala His Thr Lys Glu
        35                  40                  45 atc gac ctg gtc aac cgc gac ccc aag cat ctc aac gac gac gtg gtc       192
Ile Asp Leu Val Asn Arg Asp Pro Lys His Leu Asn Asp Asp Val Val
    50                  55                  60 aag att gat ttt gaa gat gtg att gca gaa cca gaa gga aca cac agt       240
Lys Ile Asp Phe Glu Asp Val Ile Ala Glu Pro Glu Gly Thr His Ser
65                  70                  75                  80 ttt gat ggc atc tgg aag gcc agc ttc acc acc ttc act gtg aca aaa       288
Phe Asp Gly Ile Trp Lys Ala Ser Phe Thr Thr Phe Thr Val Thr Lys
                85                  90                  95 tac tgg ttt tac cgc ttg ctg tct gcc ctc ttt ggc atc cca atg gca       336
Tyr Trp Phe Tyr Arg Leu Leu Ser Ala Leu Phe Gly Ile Pro Met Ala
            100                 105                 110 ctc ata tgg ggc att tac ttt gcc att ctt tct ttc ctg cac atc tgg       384
Leu Ile Trp Gly Ile Tyr Phe Ala Ile Leu Ser Phe Leu His Ile Trp
        115                 120                 125 gca gtt gtg ccg tgc att aag agt ttc ctg att gag att cag tgc atc       432
Ala Val Val Pro Cys Ile Lys Ser Phe Leu Ile Glu Ile Gln Cys Ile
    130                 135                 140 agc cgt gtc tat tcc atc tac gtc cac acc ttc tgt gac ccg ttc ttt       480
Ser Arg Val Tyr Ser Ile Tyr Val His Thr Phe Cys Asp Pro Phe Phe
145                 150                 155                 160 gag gct gtt ggc aaa ata ttc agc aat atc cgc atc aac atg cag aaa       528
Glu Ala Val Gly Lys Ile Phe Ser Asn Ile Arg Ile Asn Met Gln Lys
                165                 170                 175 gaa aca taa                                                            537
Glu Thr <210> SEQ ID NO 8
<211> LENGTH: 178
<212> TYPE: PRT
<213> ORGANISM: Canis lupus

<400> SEQUENCE: 8

Met Ser Gly Gly Lys Tyr Val Asp Ser Glu Gly His Leu Tyr Thr Val
```

```
                1               5                      10                      15
            Pro Ile Arg Glu Gln Gly Asn Ile Tyr Lys Pro Asn Asn Lys Ala Met
                           20                      25                      30

Ala Glu Glu Met Ser Glu Lys Gln Val Tyr Asp Ala His Thr Lys Glu
                           35                      40                      45

Ile Asp Leu Val Asn Arg Asp Pro Lys His Leu Asn Asp Asp Val Val
                50                      55                      60

Lys Ile Asp Phe Glu Asp Val Ile Ala Glu Pro Glu Gly Thr His Ser
             65                      70                      75                      80

Phe Asp Gly Ile Trp Lys Ala Ser Phe Thr Thr Phe Thr Val Thr Lys
                           85                      90                      95

Tyr Trp Phe Tyr Arg Leu Leu Ser Ala Leu Phe Gly Ile Pro Met Ala
                          100                     105                     110

Leu Ile Trp Gly Ile Tyr Phe Ala Ile Leu Ser Phe Leu His Ile Trp
                          115                     120                     125

Ala Val Val Pro Cys Ile Lys Ser Phe Leu Ile Glu Ile Gln Cys Ile
                130                     135                     140

Ser Arg Val Tyr Ser Ile Tyr Val His Thr Phe Cys Asp Pro Phe Phe
            145                     150                     155                     160

Glu Ala Val Gly Lys Ile Phe Ser Asn Ile Arg Ile Asn Met Gln Lys
                          165                     170                     175

Glu Thr

<210> SEQ ID NO 9
<211> LENGTH: 568
<212> TYPE: DNA
<213> ORGANISM: Bos taurus
<220> FEATURE:
<221> NAME/KEY: CDS
<222> LOCATION: (1)..(537)

<400> SEQUENCE: 9 atg tct ggg ggc aaa tac gta gac tca gag gga cat ctc tac act gtt        48
Met Ser Gly Gly Lys Tyr Val Asp Ser Glu Gly His Leu Tyr Thr Val
 1               5                      10                      15 ccc atc cgg gaa cag ggc aac atc tac aag ccc aac aac aag gct atg        96
Pro Ile Arg Glu Gln Gly Asn Ile Tyr Lys Pro Asn Asn Lys Ala Met
                    20                      25                      30 gca gag gaa atg aac gag aag caa gtg tac gac gcg cac acc aag gag       144
Ala Glu Glu Met Asn Glu Lys Gln Val Tyr Asp Ala His Thr Lys Glu
                35                      40                      45 ata gat ctg gtc aac cgc gac ccc aag cat ctc aac gac gac gtg gtc       192
Ile Asp Leu Val Asn Arg Asp Pro Lys His Leu Asn Asp Asp Val Val
         50                      55                      60 aag att gat ttt gaa gat gtg att gca gaa cca gaa gga aca cac agt       240
Lys Ile Asp Phe Glu Asp Val Ile Ala Glu Pro Glu Gly Thr His Ser
 65                      70                      75                      80 ttc gat ggc atc tgg aag gcc agc ttc acc acc ttc act gtg aca aaa       288
Phe Asp Gly Ile Trp Lys Ala Ser Phe Thr Thr Phe Thr Val Thr Lys
                    85                      90                      95 tac tgg ttt tac cgc ttg ctg tct gcc ctc ttt ggc atc cca atg gca       336
Tyr Trp Phe Tyr Arg Leu Leu Ser Ala Leu Phe Gly Ile Pro Met Ala
                   100                     105                     110 ctc atc tgg ggc att tac ttt gcc att ctc tct ttc ctg cac atc tgg       384
Leu Ile Trp Gly Ile Tyr Phe Ala Ile Leu Ser Phe Leu His Ile Trp
               115                     120                     125 gca gtt gta cca tgc att aag agt ttc ctg att gag att cag tgc atc       432
Ala Val Val Pro Cys Ile Lys Ser Phe Leu Ile Glu Ile Gln Cys Ile
```

```
                130                 135                 140
agc cgt gtc tat tcc atc tac gtc cac acc ttc tgt gac ccg ctg ttt    480
Ser Arg Val Tyr Ser Ile Tyr Val His Thr Phe Cys Asp Pro Leu Phe
145                 150                 155                 160 gag gct att ggc aaa ata ttc agc aat atc cgc atc aac acg cag aaa    528
Glu Ala Ile Gly Lys Ile Phe Ser Asn Ile Arg Ile Asn Thr Gln Lys
                165                 170                 175 gaa ata taa atgacatttc aaggaaaaaa aaaaaaaaaa a                     568
Glu Ile
```

<210> SEQ ID NO 10
<211> LENGTH: 178
<212> TYPE: PRT
<213> ORGANISM: Bos taurus

<400> SEQUENCE: 10

```
Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Glu Met Asn Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Phe Cys Asp Pro Leu Phe
145                 150                 155                 160

Glu Ala Ile Gly Lys Ile Phe Ser Asn Ile Arg Ile Asn Thr Gln Lys
                165                 170                 175

Glu Ile
```

<210> SEQ ID NO 11
<211> LENGTH: 2702
<212> TYPE: DNA
<213> ORGANISM: Equus caballus
<220> FEATURE:
<221> NAME/KEY: CDS
<222> LOCATION: (268)..(804)

<400> SEQUENCE: 11

```
gagcgaaacg ctttctcact gctctttgct ccccgccctc tgctgccaga accttgggga     60
tgtgcctaga ctcggcgcag cgcacgtcct ggccaaccgc gagcgagaaca aacccttggc    120 cttcggccag gaggctccct cccagccacc gccccccgcc agcgcctttt ttttttccccc   180 atacaatacaa agatcttcct tcctcagttc ccttaaatca cggcccaggg aaatctcctc   240
aaagccttca tccagccacg ggccagc atg tct ggg ggc aaa tac gtg gac tcc    294
                               Met Ser Gly Gly Lys Tyr Val Asp Ser
                                 1               5
```

```
gag gga cat ctc tat acg gtt ccc atc cgg gaa cag ggc aac atc tac      342
Glu Gly His Leu Tyr Thr Val Pro Ile Arg Glu Gln Gly Asn Ile Tyr
 10              15                  20                  25 aag ccc aac aac aag gcc atg gca gac gag atg aac gag aag caa gtg      390
Lys Pro Asn Asn Lys Ala Met Ala Asp Glu Met Asn Glu Lys Gln Val
             30                  35                  40 tac gac gcg cac acc aag gag atc gac ctg gtc aac cgc gac ccc aag      438
Tyr Asp Ala His Thr Lys Glu Ile Asp Leu Val Asn Arg Asp Pro Lys
                 45                  50                  55 cat ctc aac gac gat gtg gtc aag att gat ttt gaa gat gtg att gca      486
His Leu Asn Asp Asp Val Val Lys Ile Asp Phe Glu Asp Val Ile Ala
                     60                  65                  70 gaa cca gaa gga aca cac agt ttc gac ggc atc tgg aag gcc agc ttc      534
Glu Pro Glu Gly Thr His Ser Phe Asp Gly Ile Trp Lys Ala Ser Phe
         75                  80                  85 acc acc ttc act gtg aca aag tac tgg ttt tac cgc ttg ctg tct gcc      582
Thr Thr Phe Thr Val Thr Lys Tyr Trp Phe Tyr Arg Leu Leu Ser Ala
 90              95                 100                 105 ctc ttt ggc atc cca atg gcg ctc atc tgg ggc att tac ttt gcc att      630
Leu Phe Gly Ile Pro Met Ala Leu Ile Trp Gly Ile Tyr Phe Ala Ile
             110                 115                 120 ctc tct ttc ctg cac atc tgg gca gtt gta ccg tgc att aag agt ttc      678
Leu Ser Phe Leu His Ile Trp Ala Val Val Pro Cys Ile Lys Ser Phe
                 125                 130                 135 ctg att gag att cag tgc atc agc cgt gtc tat tcc atc tac gtc cac      726
Leu Ile Glu Ile Gln Cys Ile Ser Arg Val Tyr Ser Ile Tyr Val His
                     140                 145                 150 acc ttc tgt gac cca ctc ttt gag gct att ggc aaa ata ttc agc aat      774
Thr Phe Cys Asp Pro Leu Phe Glu Ala Ile Gly Lys Ile Phe Ser Asn
         155                 160                 165 gtc cgc atc aac ctg cag aaa gaa ata taa atgacatttc gaggatagaa        824
Val Arg Ile Asn Leu Gln Lys Glu Ile
170                 175 gtatacctga ttctattttt ttccttttaa ttttcttggt gccaatttca agtttcaagt    884
tgctagtaca gcaacaatat atgaatgaat tttcttggtt cagaacaaag aaatcactct    944
ctcagtcttc ataactgtta tttgtctctt ctgagttatt tcatctattt tttttgatg    1004 gtctgaattt tttaaaccca ttcaaaattt ttttcgcaca ttttatttg catgtggatc    1064 cttgtgttat tggcagagat gtgaacctat tgttgaaaga taatttgaga gaaatatgga   1124
gaactgagga ggaaagaaaa gaaccaacaa cctcaactgc ctattctaaa acgttgatca   1184
ttttatggta agggaagaat tccaggccat ggccattaag tgtacaggta tgtgggcagg   1244
ttttaagcaa actctttccc caccatctga agcgttagtg gactgctgct attcacttta   1304
ataattcaat gggctccaat ggtctttctc atgttagaaa acataacctg cattcacatg   1364
gtccgactaa tgccttaccc ttcttgaaat tttaacctgt gatactttct gtgcctacat   1424
atttgttata tagataatga acccaagtg ccttcctgtt cttcacattt tcgttttcaa    1484 ataggtcca acttaactgt caactttcat taggtcaaca gcctccctga agaccaaaat    1544
tagaaaattc attaactagt tctctatgct ggtttctgac tctgcgatcc agagtcagat   1604
gaagtccagg tctgcactcg atcacacagc atctttgtcc atgttgagta tggttcacat   1664 cagcccatg aaacaaatta aggtggacga acggggttga gccctctctg agctggcagg    1724
agtggaagcc aactttccct gccactcacg agctgcacga ggtcagcatg tctattcagc   1784
ttcgttgatt ttcaagaata atcacgcttt cctgactcca aactaatcca tcacccgggt   1844
ggtttagtgg ctgaacattg tgttcccctt tcagctgatc agtgggcctc tggggaaggg   1904
```

```
ctcataaaat ggaggccatt gtatgagtct atcagagttg ttgcaaatgt gaccccttca    1964
aagtaaagca cttgcaaccg tctgttatgc tgtgacacac agcccctccc cctgccagga    2024
gcttgggtct aatacaagca tcactttgct cacagagaag atggggagga ggcagtcata    2084
aaagattgag gtaattttgc tggaataagt tcaaattctt ttgaactcaa actgaggaat    2144
ttttacctgt aaacctgagt catacagaaa gctgcctggt acatccaaaa gcttttcatt    2204
cttgttcaaa ttaagattct gcccttgggg attttatttt taaccttcag ttatgctttt    2264
atttttattt tcatacacct attggaactc tgcttgattt tttttttcct gcctcttcca    2324
gttttcctga cacttcagtt atcaacctgt tccctacttt gattttttgc atttaaaaca    2384
gacactggca tggacatagt tttactttta aactgtgtac ataactgaaa atgtactata    2444
ctgcgtactt tttaagtgta aagatatttt tatctttata tgaggaaaat cacttaggga    2504
aatgctttgt gattcaatct gtaaactgtg tatcccaaga catgtctgtt ctacatagat    2564
gcttagtccc tcgcgcaaat gaagcgctgg tccaggagac tgctaaaatt ttatatgctt    2624
actgatatat tttacacttt tttatcctgc atgtcctgta aaggtgacaa gtctgcacaa    2684
taaaaatgtt taacagtt                                                 2702
```

<210> SEQ ID NO 12
<211> LENGTH: 178
<212> TYPE: PRT
<213> ORGANISM: Equus caballus

<400> SEQUENCE: 12

```
Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Met Asn Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Glu Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Phe Cys Asp Pro Leu Phe
145                 150                 155                 160

Glu Ala Ile Gly Lys Ile Phe Ser Asn Val Arg Ile Asn Leu Gln Lys
                165                 170                 175

Glu Ile
```

<210> SEQ ID NO 13
<211> LENGTH: 13
<212> TYPE: DNA
<213> ORGANISM: Artificial Sequence
<220> FEATURE:
<223> OTHER INFORMATION: Conserved sequence element

```
<220> FEATURE:
<221> NAME/KEY: misc_feature
<222> LOCATION: (2)..(2)
<223> OTHER INFORMATION: S = C or G
<220> FEATURE:
<221> NAME/KEY: misc_feature
<222> LOCATION: (5)..(5)
<223> OTHER INFORMATION: Y = C or T
<220> FEATURE:
<221> NAME/KEY: misc_feature
<222> LOCATION: (9)..(9)
<223> OTHER INFORMATION: Y = C or T
<220> FEATURE:
<221> NAME/KEY: misc_feature
<222> LOCATION: (11)..(11)
<223> OTHER INFORMATION: Y = C or T

<400> SEQUENCE: 13
csttygccyc ygc                                                     13

<210> SEQ ID NO 14
<211> LENGTH: 12
<212> TYPE: DNA
<213> ORGANISM: Artificial Sequence
<220> FEATURE:
<223> OTHER INFORMATION: Conserved sequence element
<220> FEATURE:
<221> NAME/KEY: misc_feature
<222> LOCATION: (3)..(3)
<223> OTHER INFORMATION: S = C or G
<220> FEATURE:
<221> NAME/KEY: misc_feature
<222> LOCATION: (11)..(11)
<223> OTHER INFORMATION: N = A, G, C or T

<400> SEQUENCE: 14
cgstgacgtc nc                                                      12
```